(12) United States Patent
Unger et al.

(10) Patent No.: US 11,235,070 B2
(45) Date of Patent: Feb. 1, 2022

(54) NANOPARTICLES COMPRISING PROTEIN-POLYNUCLEOTIDE COMPLEXES AND FOR DELIVERING PROTEIN BASED COMPLEXES

(71) Applicant: ASKLEPIOS BIOPHARMACEUTICAL, INC., Research Triangle Park, NC (US)

(72) Inventors: Gretchen M. Unger, Chaska, MN (US); Vicci Korman, Minneapolis, MN (US)

(73) Assignee: Asklepios Biopharmaceutical, Inc., Research Triangle Park, NC (US)

( * ) Notice: Subject to any disclaimer, the term of this patent is extended or adjusted under 35 U.S.C. 154(b) by 0 days.

(21) Appl. No.: 16/350,840

(22) Filed: Jan. 22, 2019

(65) Prior Publication Data

US 2019/0270989 A1    Sep. 5, 2019

Related U.S. Application Data

(63) Continuation of application No. PCT/US2019/014390, filed on Jan. 20, 2019, which is a continuation of application No. 16/252,354, filed on Jan. 18, 2019, now abandoned.

(60) Provisional application No. 62/624,100, filed on Jan. 30, 2018, provisional application No. 62/619,881, filed on Jan. 21, 2018, provisional application No. 62/619,882, filed on Jan. 21, 2018, provisional application No. 62/619,883, filed on Jan. 21, 2018, provisional application No. 62/619,885, filed on Jan. 21, 2018.

(51) Int. Cl.
| | | |
|---|---|---|
| *C07H 21/04* | (2006.01) | |
| *A61K 48/00* | (2006.01) | |
| *C12N 9/22* | (2006.01) | |
| *C12N 15/11* | (2006.01) | |
| *A61K 47/69* | (2017.01) | |
| *A61P 1/16* | (2006.01) | |
| *A61P 11/00* | (2006.01) | |
| *A61K 9/51* | (2006.01) | |

(52) U.S. Cl.
CPC ............ *A61K 48/0008* (2013.01); *A61K 9/51* (2013.01); *A61K 47/6907* (2017.08); *A61K 48/0058* (2013.01); *A61K 48/0066* (2013.01); *A61K 48/0091* (2013.01); *A61P 1/16* (2018.01); *A61P 11/00* (2018.01); *C12N 9/22* (2013.01); *C12N 15/11* (2013.01); *C12N 15/111* (2013.01); *C12N 2310/14* (2013.01); *C12N 2310/20* (2017.05); *C12N 2320/32* (2013.01)

(58) Field of Classification Search
None
See application file for complete search history.

(56) References Cited

U.S. PATENT DOCUMENTS

| | | | |
|---|---|---|---|
| 6,632,671 B2 * | 10/2003 | Unger | ................. A61K 9/1075 |
| | | | 264/4.1 |
| 7,927,613 B2 | 4/2011 | Almarsson | |
| 9,132,148 B2 | 9/2015 | Unger | |
| 2010/0173001 A1 | 7/2010 | Unger | |
| 2012/0007673 A1 | 3/2012 | Peyman | |
| 2014/0155733 A1 | 6/2014 | Unger | |
| 2015/0232881 A1 | 8/2015 | Glucksman | |
| 2016/0058706 A1 | 3/2016 | Unger | |
| 2017/0247253 A1 | 8/2017 | Unger | |
| 2018/0008687 A1 | 11/2018 | Ghoroghchian | |

FOREIGN PATENT DOCUMENTS

| | | |
|---|---|---|
| WO | WO 2008/095192 | 8/2008 |
| WO | WO 2009/049089 | 4/2009 |
| WO | WO 2017/185054 A1 | 10/2017 |

OTHER PUBLICATIONS

Ahmed, K. et al., "CK2 targeted RNAi therapeutic delivered via malignant cell-directed tenfiber nanocapsule: dose and molecular mechanisms of response in xenograft prostate tumors," Oncotarget, 7(38):61789-61805, Aug. 20, 2016.
International Search Report and Written Opinion in International Application No. PCT/US2019/014390, dated Jul. 23, 2019 (10 pages).
International Preliminary Report on Patentability in International Application No. PCT/US2019/014390, dated Jul. 21, 2020 (7 pages).
Almarsson, Ö. et al., "The A to Z of pharmaceutical cocrystals: a decade of fast-moving new science and patents," Pharm Part Analyst 1(3):313-327 (2012).
Braga, D. et al., "The growing world of crystal forms," Chem Commun 46:6232-6242 (2010).
Brooker, M. H., "Raman and Infrared Studies of Lithium and Cesium Carbonates," Spectrochimica Acta 48a(7):999-1008 (1992).

(Continued)

*Primary Examiner* — Kimberly Chong
(74) *Attorney, Agent, or Firm* — Nixon Peabody LLP

(57) ABSTRACT

This invention provides nanoparticles containing protein-polynucleotide complexes and methods of manufacture and methods of their use. These particles, when administered to a subject in need, are capable of delivering these complexes to target cells and target intracellular locations where they can perform a therapeutic function. In some embodiments, this therapeutic function includes gene editing, induction of gene skipping, and regulation of gene expression. The instant nanoparticles are generally formed by designing and synthesizing the polynucleotide to according to its intended function, combining it with a protein selected for its substrate specificity and enzymatic function in a manner to form a polynucleotide-protein complex, encapsulating the complexes by dispersion into a water-insoluble surfactant system, optionally adding a targeting ligand, and stabilizing the nanoparticles by crystallization of the ligand to the surface of the nanoparticles.

20 Claims, 40 Drawing Sheets

(56) References Cited

OTHER PUBLICATIONS

Brown, M. et al., "CK2 Modulation of NF-κB, TP53, and the Malignant Phenotype in Head and Neck Cancer by Anti-CK2 Oligonucleotides In vitro or In vivo via Sub-50-nm Nanocapsules," Clin Can Res 16(8):2295-2307 (2010).

Ding, F. et al., "Dendrite-Free Lithium Deposition via Self-Healing Electrostatic Shield Mechanism," J Am Chem Soc 135:4450-4456 (2013).

Ding, F. et al., "Effects of Cesium Cations in Lithium Deposition via Self-Healing Electrostatic Shield Mechanism," J Phys Chem 118:4043-4049 (2014).

Ma, X., "Effect of alkali metal cations on adsorption of guar gum onto quartz," Thesis, Vancouver: University of British Columbia Library, pp. 1-82 (2009).

Matsuta, S. et al., "Vibrational Assignments of Lithium Alkyl Carbonate and Lithium Alkoxide in the Infrared Specctra An *Ab Initio* MO Study," Journal of Electrochemical Society 147(5):1695-1702 (2000).

Ong, T. T., "Crystal Engineering of Molecular and Ionic Cocrystals," Dissertation, University of South Florida, pp. 1-193 (2011).

Ong, T. T., "2:1 Cocrystals of Homochiral and Achiral Amino Acid Zwitterions with Li+ Salts: Water-Stable Zeolitic and Diamondoid Metal-Organic Materials," J Am chem Soc 133:9224-9227 (2011).

Smith, A. et al., "Improving Lithium Therapeutics by Crystal Engineering of Novel Ionic Cocrystals," Mol Pharmaceutics 10:4728-2738 (2013).

Trask, A., "An Overview of Pharmaceutical Cocrystals as Intellectual Property," Mol Pharmaceutics 4(13):301-309 (2013).

Trembley, J. et al., "Tenfibgren Ligand Nanoencapsulation Delivers Bi-Functional Anti-CK2 RNAi Oligomer to Key Sites for Prostate Cancer Targeting Using Human Xenograft Tumors in Mice," PLOS One 9(10)e109970:1-12 (2014).

Unger, G. et al., "Mechanism and Efficacy of Sub-50-nm Tenfibgren Nanocapsules for Cancer Cell-Directed Delivery of Anti-CK2 RNAi to Primary and Metastatic Squamous Cell Carcinoma," Mol Cancer Ther 13(8):2018-2029 (2014).

\* cited by examiner

TEM MICROGRAPH FOR FORMULA HA, ASOR RNP muF7-310C

4-10. TIF
4
PRINT MAG: 271000x @ 7.0 in
2:04:59 PM 6/14/2016
MICROSCOPIST: RICHARD AN 100 nm
DIRECT MAG. 80000x
AMT CAMERA SYSTEM

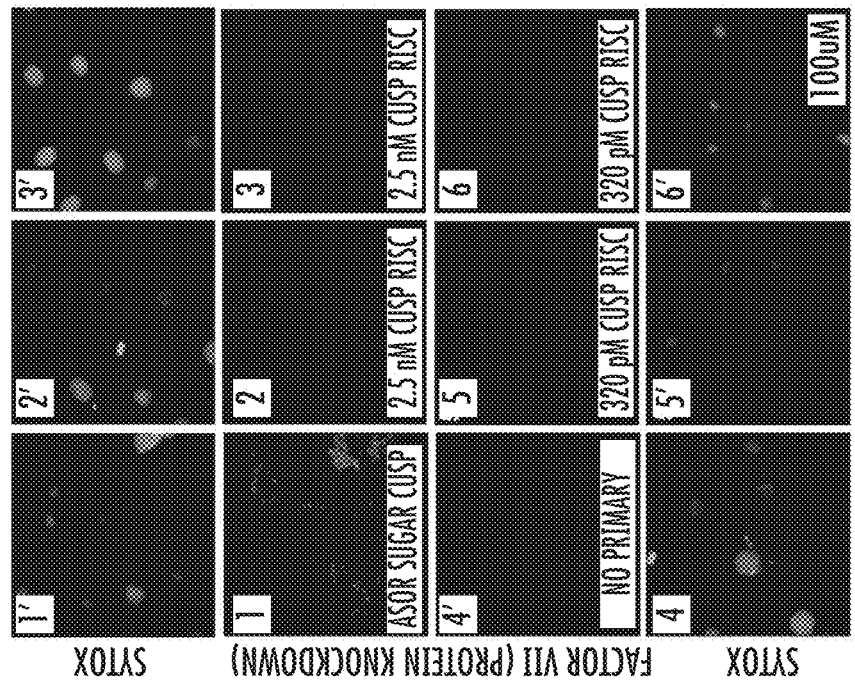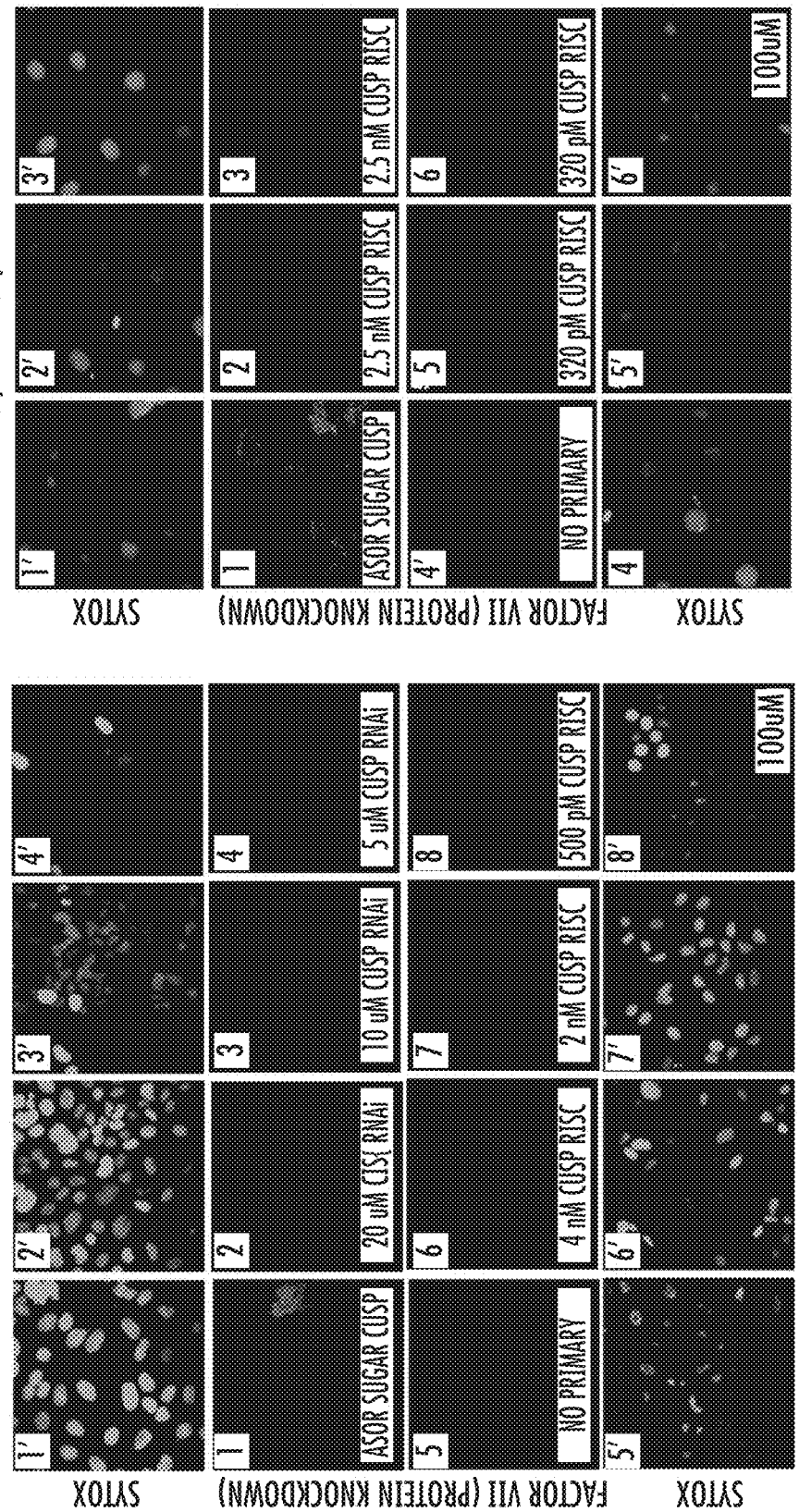
FIG. 3

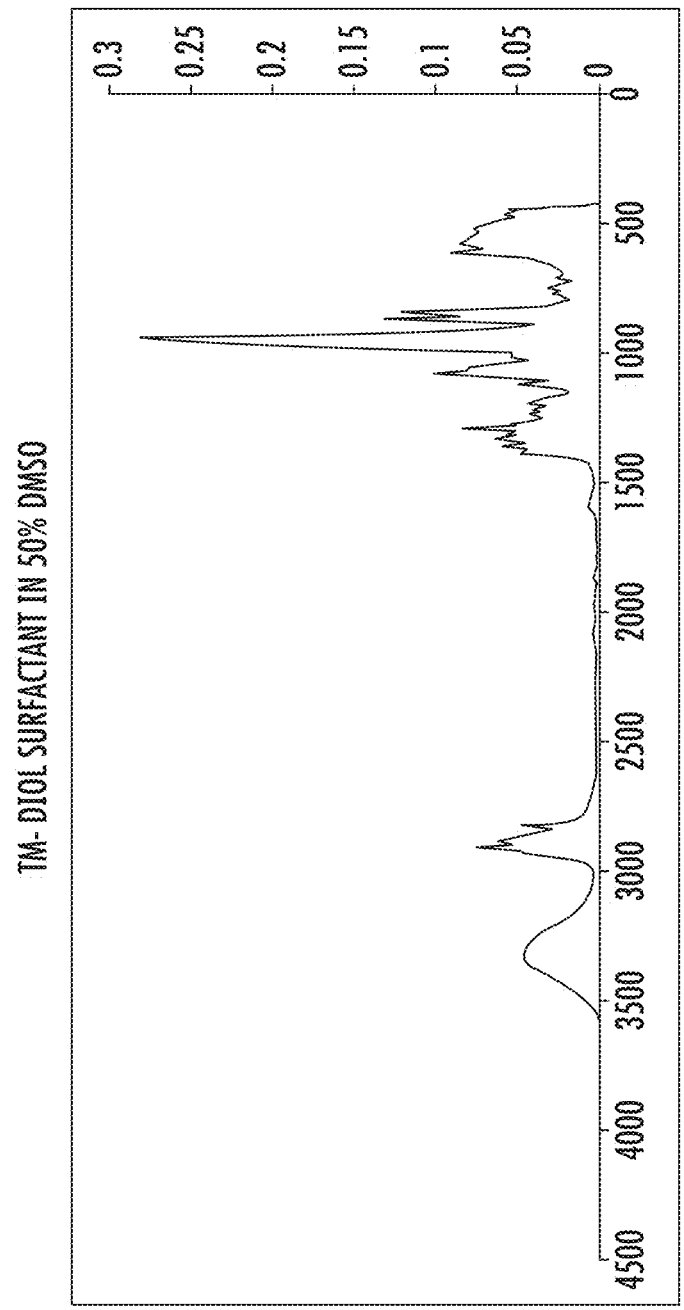
FIG. 11.5

NANOPARTICLES COMPRISING PROTEIN-POLYNUCLEOTIDE COMPLEXES AND FOR DELIVERING PROTEIN BASED COMPLEXES

I. CROSS-REFERENCES TO RELATED APPLICATIONS

This application claims priority to and the benefit of PCT Application No. PCT/US 19/14390, filed on 20 Jan. 2019 which claims priority to U.S. application Ser. No. 16/252,354, filed on 18 Jan. 2019, which claims priority to U.S. Provisional Application No. 62/619,881, filed on 21 Jan. 2018, U.S. Provisional Application No. 62/619,882, filed on 21 Jan. 2018, U.S. Provisional Application No. 62/619,883, filed on 21 Jan. 2018, U.S. Provisional Application No. 62/619,885, filed on 21 Jan. 2018 and U.S. Provisional Application No. 62/624,100, filed 30 Jan. 2018, each of which are hereby incorporated by reference in their entireties as if fully set forth herein.

II. FIELD OF THE INVENTION

The instant invention relates generally to the field of therapy using nanoparticles to deliver biologic agents. More specifically, the present invention relates to nanoparticles, methods of their manufacture, and methods of use for delivering biologic agents.

III. BACKGROUND

Genome editing technologies have shown much potential in their ability to change the genetic code of cells. These technologies could enable novel insights in drug discovery and lead to the development of next generation gene therapies.

One such genome editing technology is the so-called "CRISPR technology, in which a targeting RNA (sgRNA) complexes with one or more CRISPR associated proteins such as Cas9 and directs the complex to the target where the nuclease activity of the Cas protein cuts the DNA.

RNA interference (RNAi) is also a powerful tool to silence or reduce the expression of a target gene and is mediated by small single- or double-stranded RNA molecules. These molecules, such as siRNAs, miRNAs and shRNAs, are important intermediaries in the RNAi pathway that lead to degradation of specific mRNAs through the RNA-induced silencing complex (RISC). During assembly of RISC, a single strand of the RNA molecules binds to the protein Argonaute 2 (Ago2), a key component of RISC. This strand then guides RISC to its complementary target mRNA, which is finally cleaved by the RNase activity located in the Ago2 protein, triggering its destruction.

Other gene editing complexes such as structure-guided endonuclease gene editing technology and triplex-forming peptide nucleic acid oligomers are being developed with promising therapeutic utility.

However, the utility of these methods for human therapy is fraught with challenges. There is a need for developing or improving methods of delivering sufficient levels of these tools to the proper target cells and to the proper intracellular localization. While ongoing efforts seem to focus on delivering the polynucleotide component(s), assembly in situ with the endogenous protein components is often limiting. Thus there remains a need at several levels for developing these tools for effecting gene therapy.

Furthermore, despite significant research over a period of more than 30 years, the development of proteins as therapeutic agents has been hindered by problems in effective and efficient delivery. Proteins induce inflammatory reactions in the blood and are subject to significant enzymatic degradation both in vitro and in vivo. Solutions to protect protein therapies are often thwarted by the fragile nature of the protein and the challenges of stabilizing while also preserving functionality.

Encapsulation of proteins is one of numerous protective strategies to improve delivery. However, protein encapsulation yields are often low, necessitating efforts to chemically stabilize the protein but which can also significantly denature the protein. Further, protein encapsulation approaches often must be evaluated on an empirical, case-by-case basis, as the protective effects of solutes are variable.

There is also therefore, a need for improved delivery of protein therapeutics with high encapsulation yields and low toxicity levels, in a modular system.

IV. SUMMARY OF THE INVENTION

Provided here are nanoparticles, methods of their manufacture, and methods of use for delivering biologic agent. In one embodiment, the instant invention is a composition of nanoparticles comprising a polynucleotide component, a protein component, a surfactant having an HLB value of less than 6.0 units, optionally a hydrophilic polymer, optionally a ligand, and optionally Li+ and Cs+, wherein:
i) the protein component and the polynucleotide component function as a complex in concert as a biologic agent;
ii) the protein component and the polynucleotide component form a complex;
iii) the complex and the surfactant form a surfactant micelle core;
iv) the optional hydrophilic polymer forms a shell around the micelle core;
v) the nanoparticles have an average diameter of less than about 50 nanometers; and
vi) the biologic agent is optionally a therapeutic agent.

In another embodiment, the instant invention comprises a method of making a nanoparticle of the present invention.

In another embodiment, the instant invention comprises a method of using the instant invention for example to treat a subject in need comprising administering a nanoparticle of the present invention to the subject where the protein component and polynucleotide component are designed to alter gene expression of a disease-relevant gene.

V. BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figures, and Examples, which illustrate embodiments, wherein:

FIG. 3 shows immunomicroscopy from RISC nanoparticles in 3D hepatocyte cultures;

Figure 2:
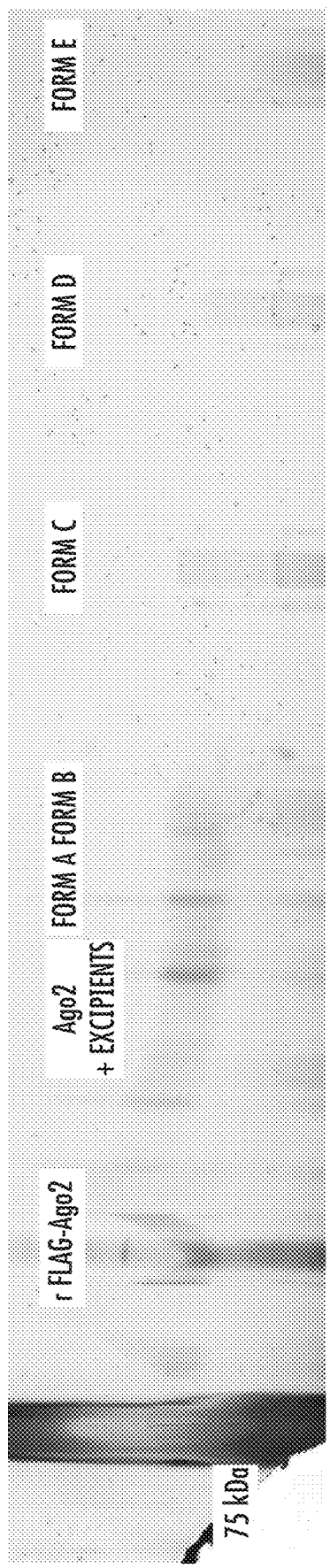
FIG. 2 is Silver-stained gel of supernatants from reaction mixtures.
Figure 11:
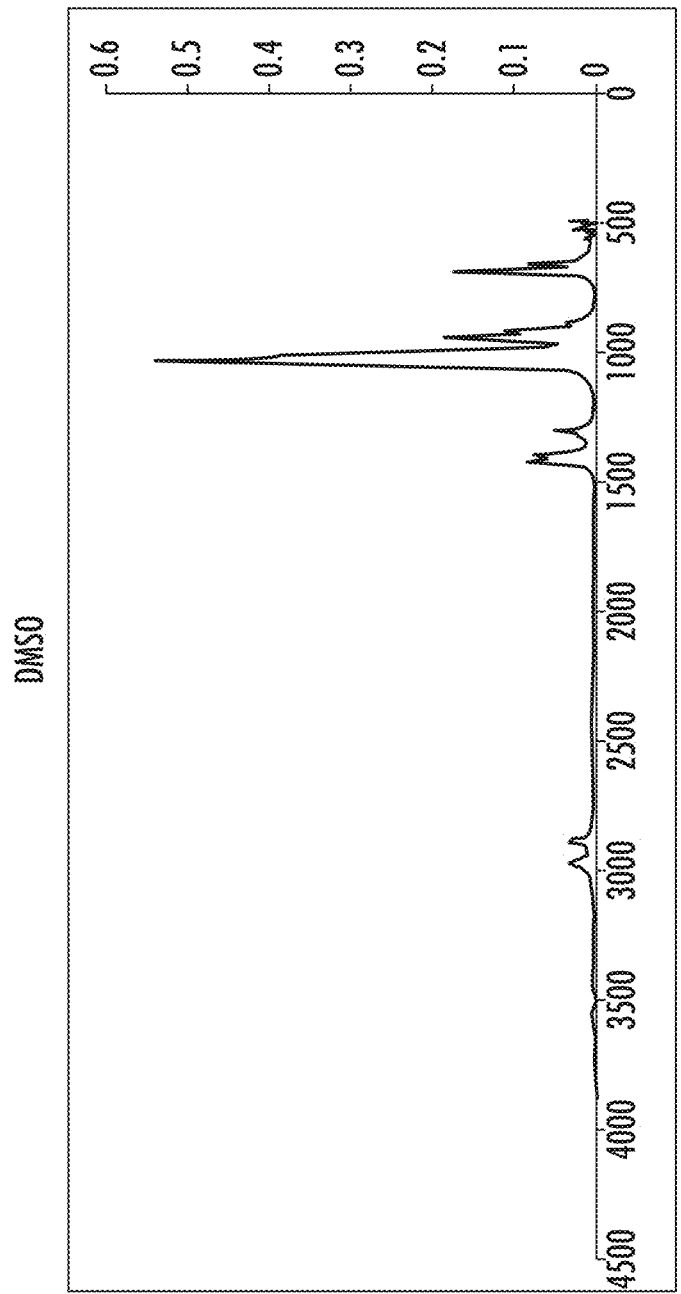
FIG. 11 shows FT-IR Scan for DMSO.
Figure 12:
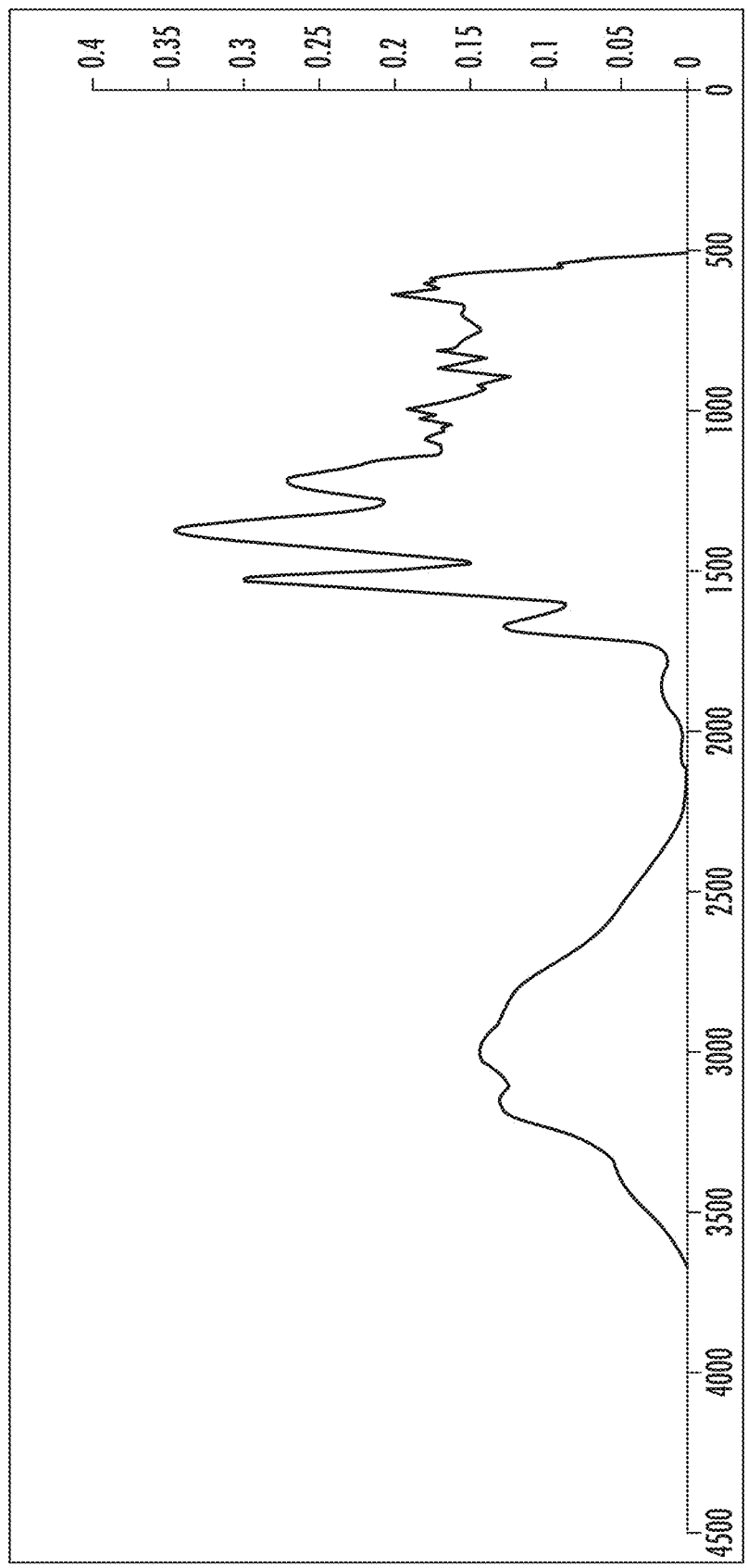
Figure 13:
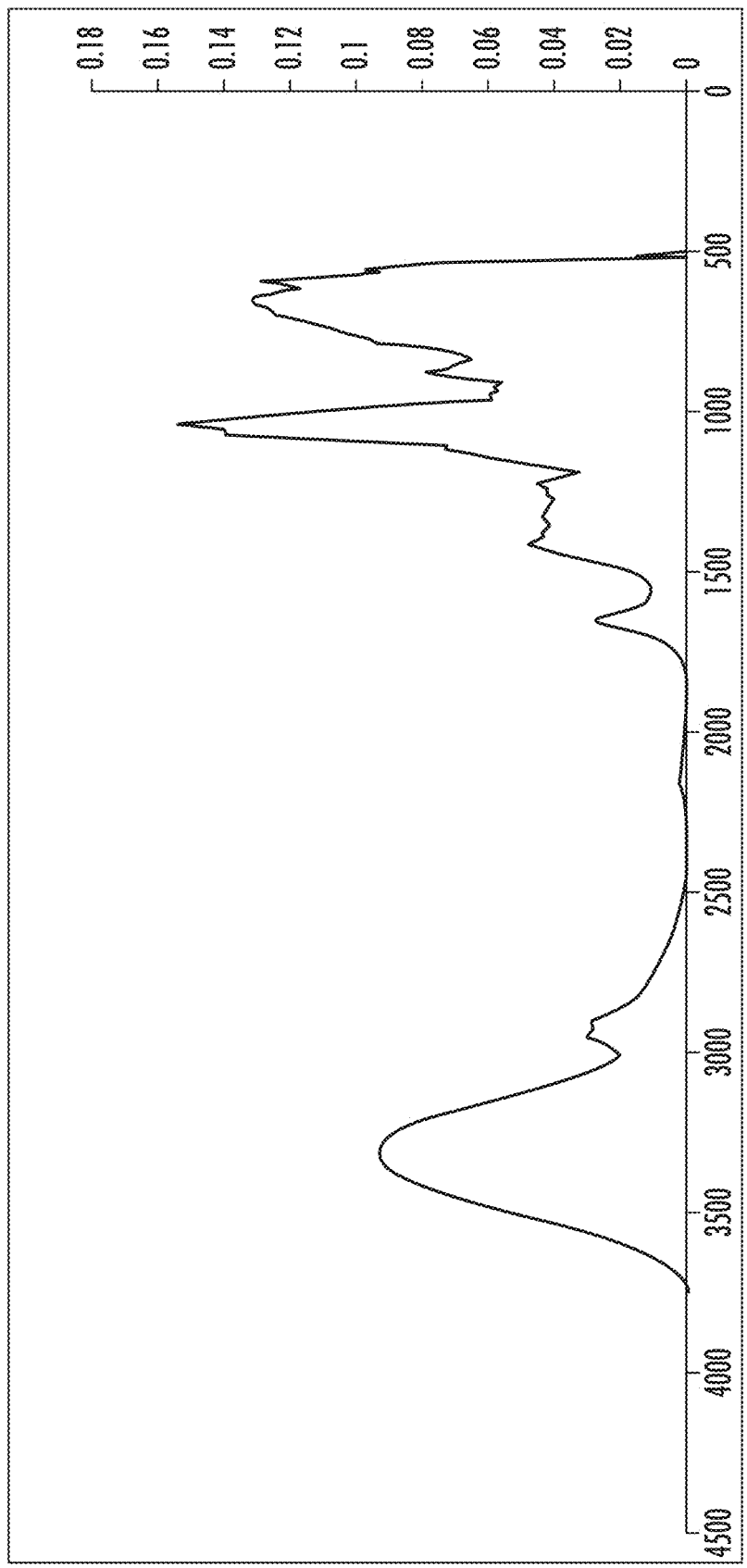
Figures 2, 13:
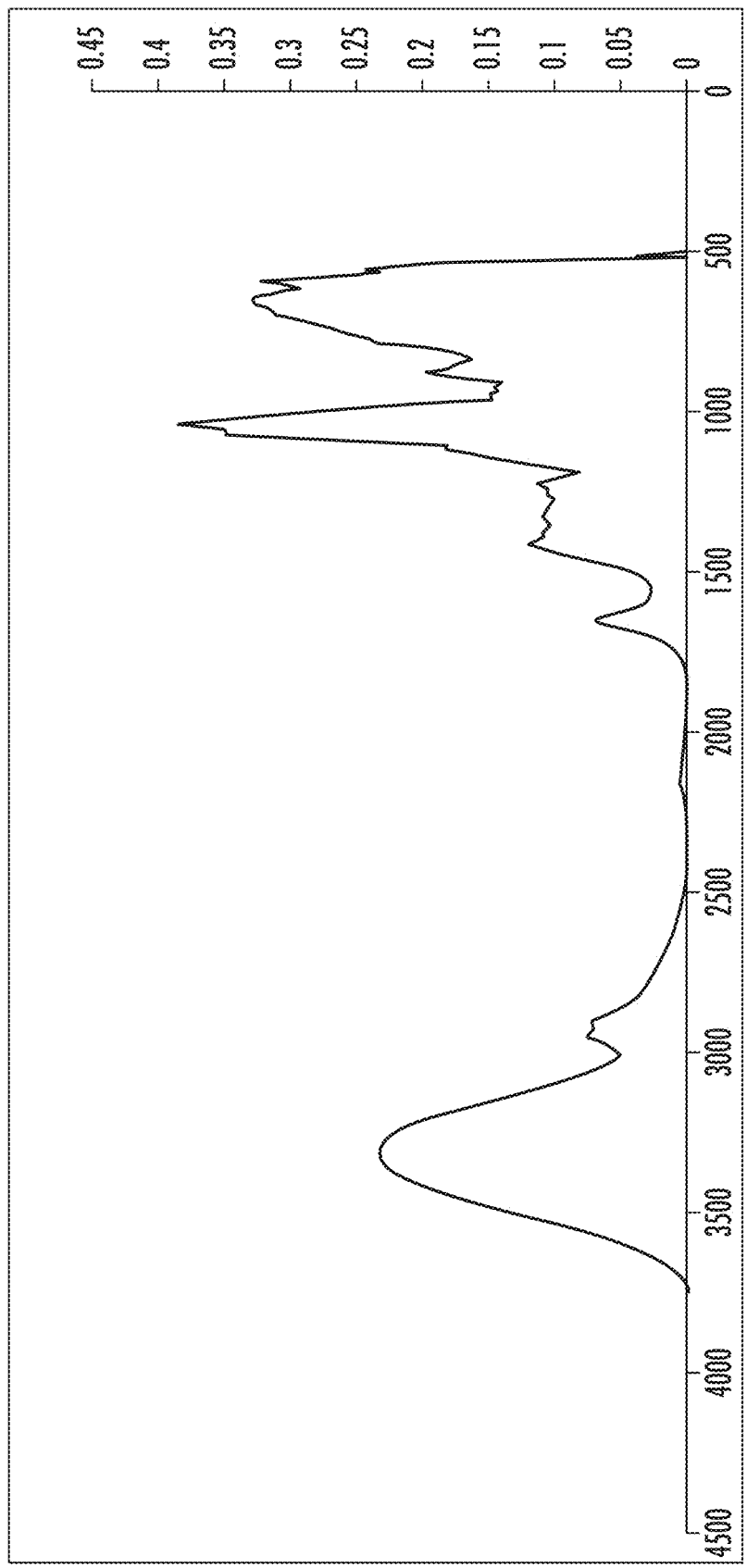
Figure 14:
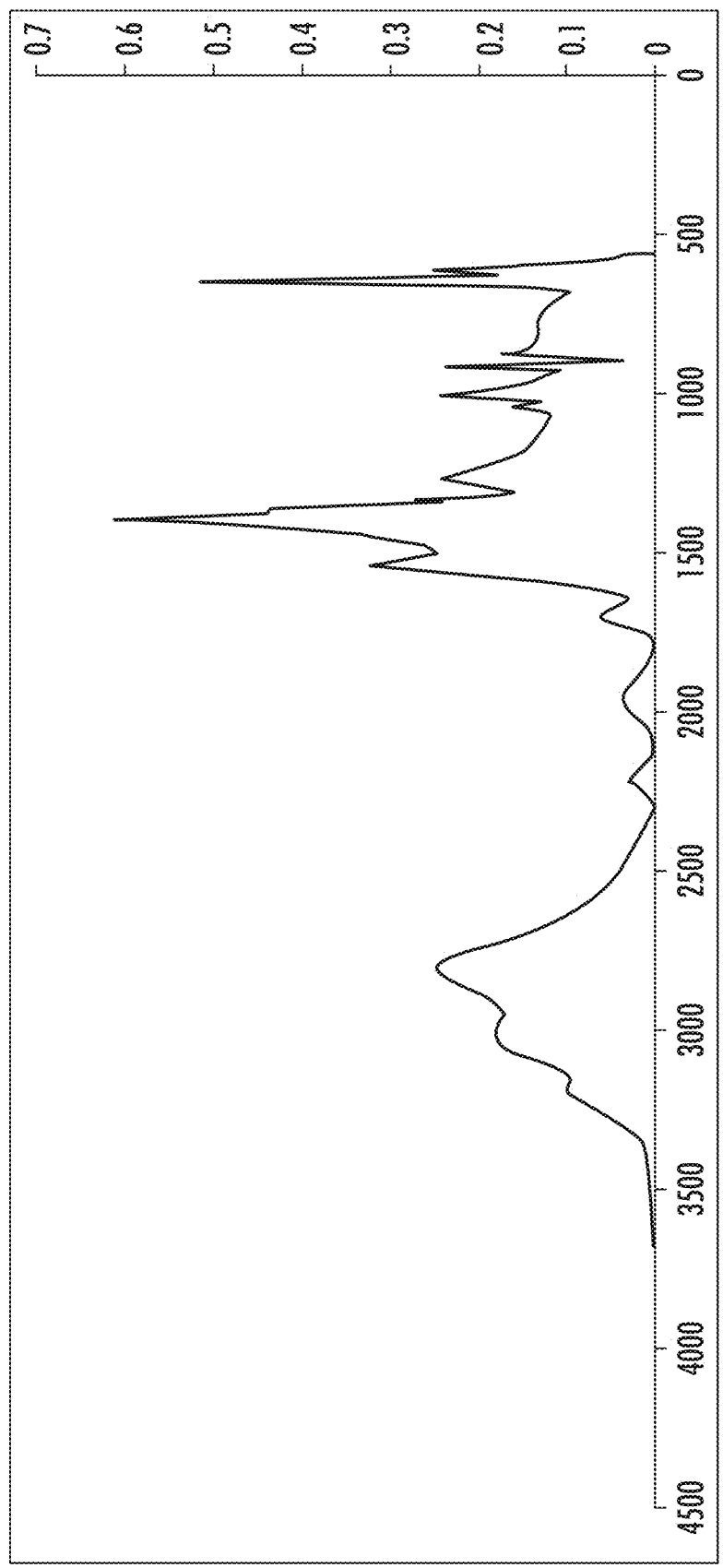
Figure 15:
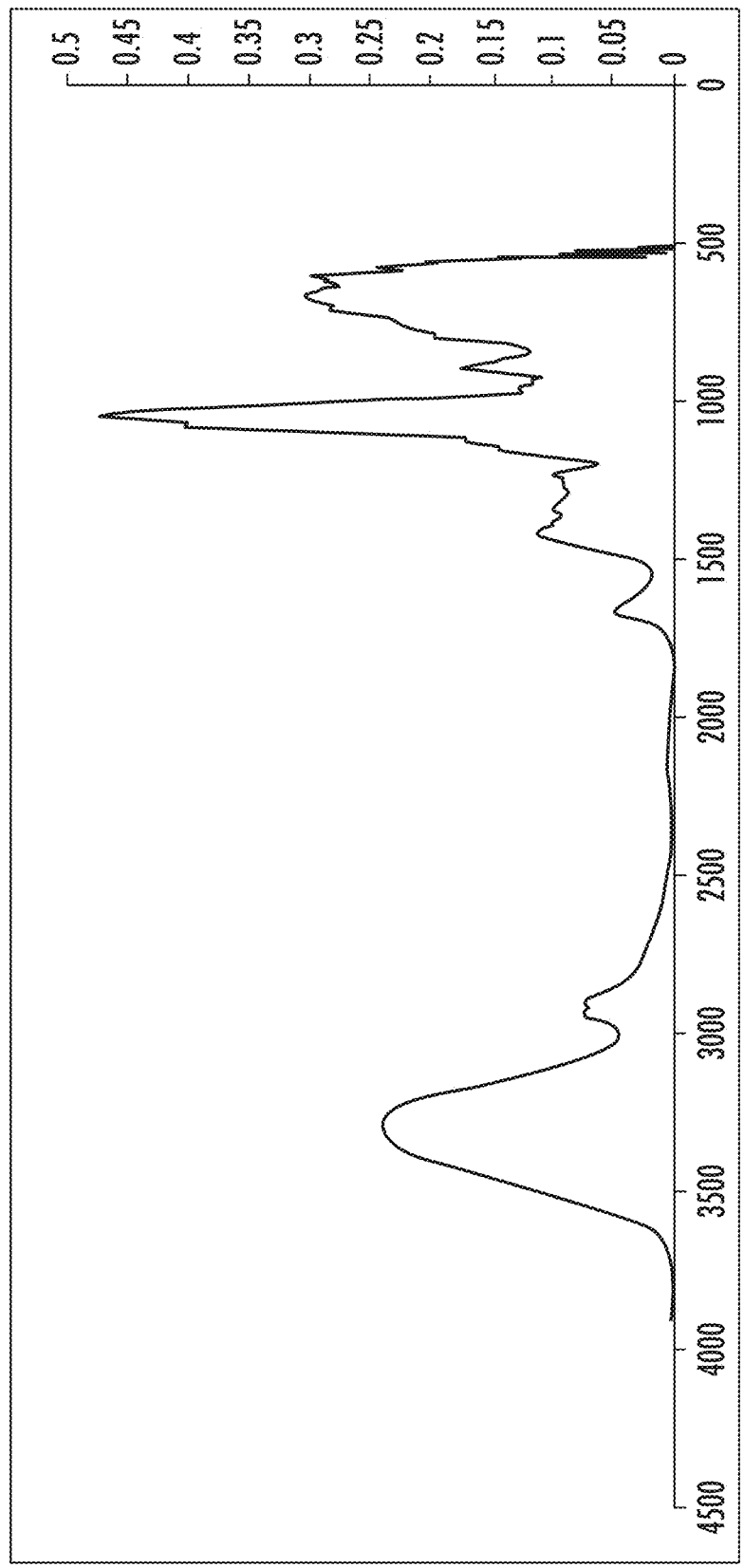
Figure 16:
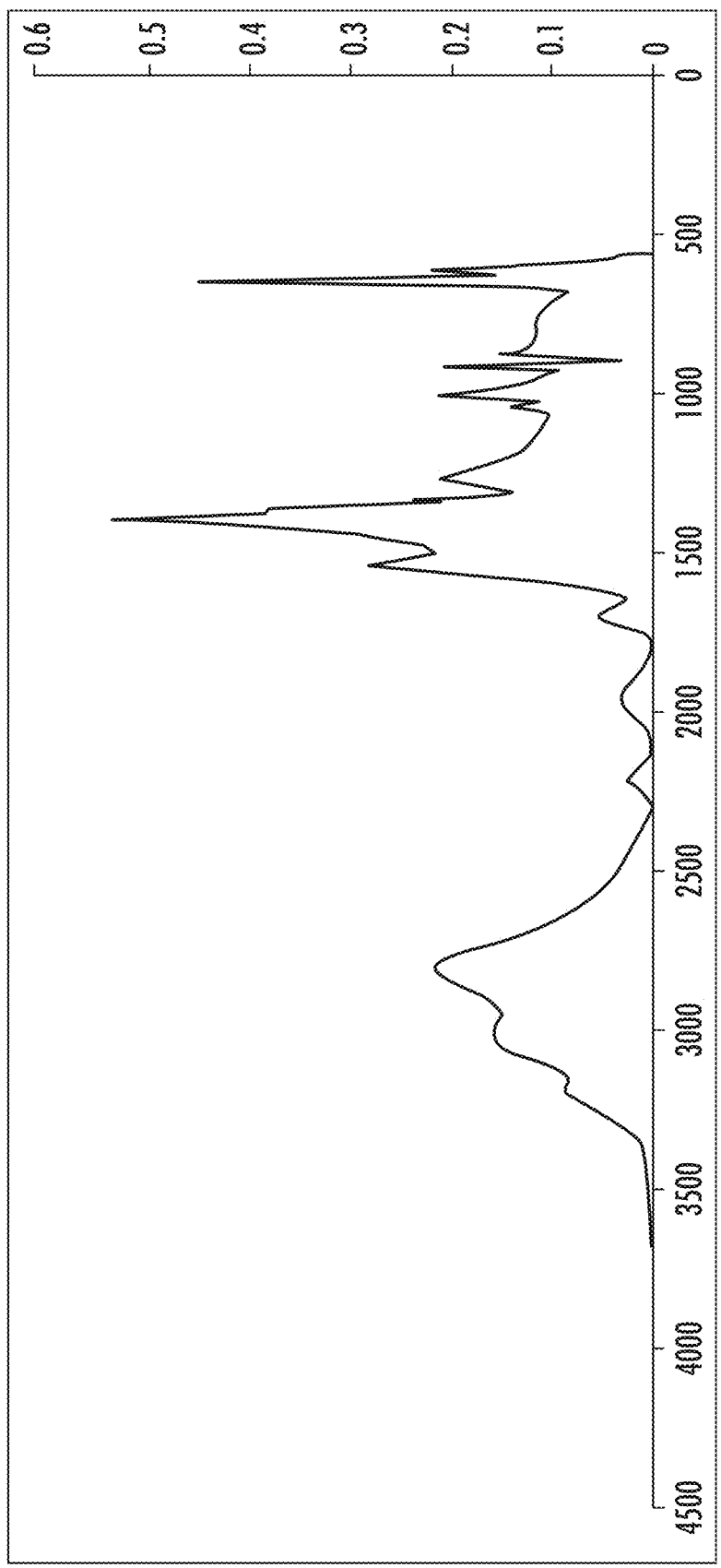
Figure 17:
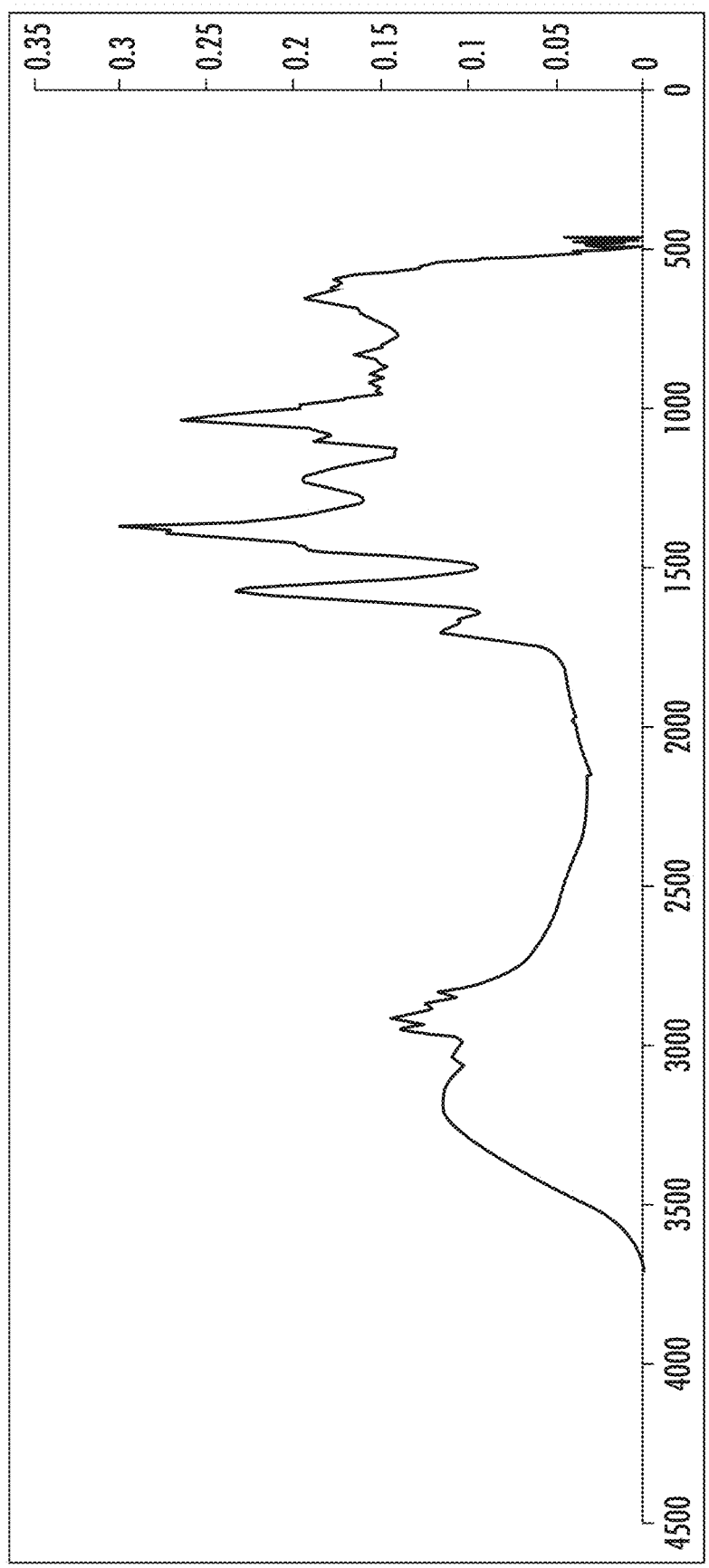
Figure 18:
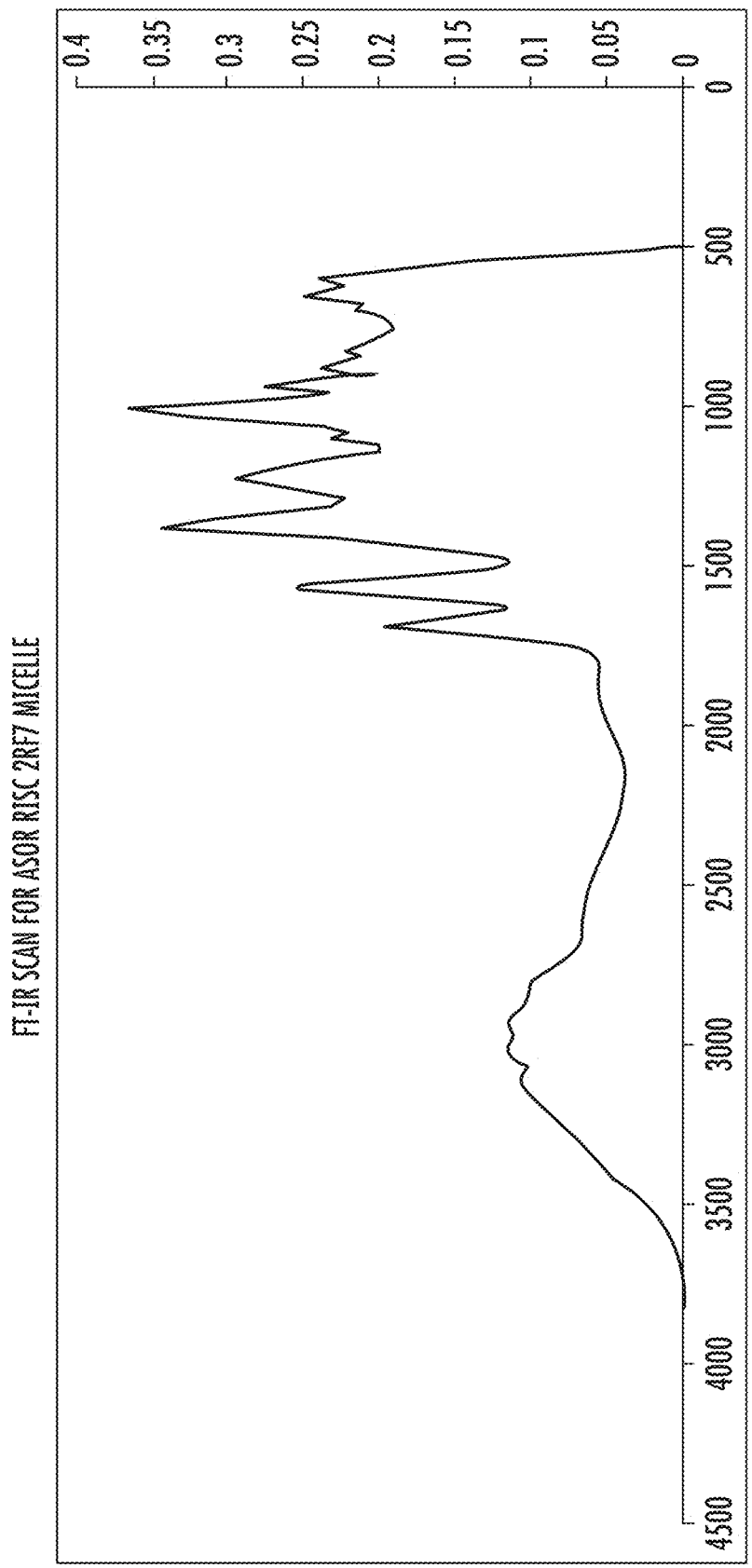
Figure 19:
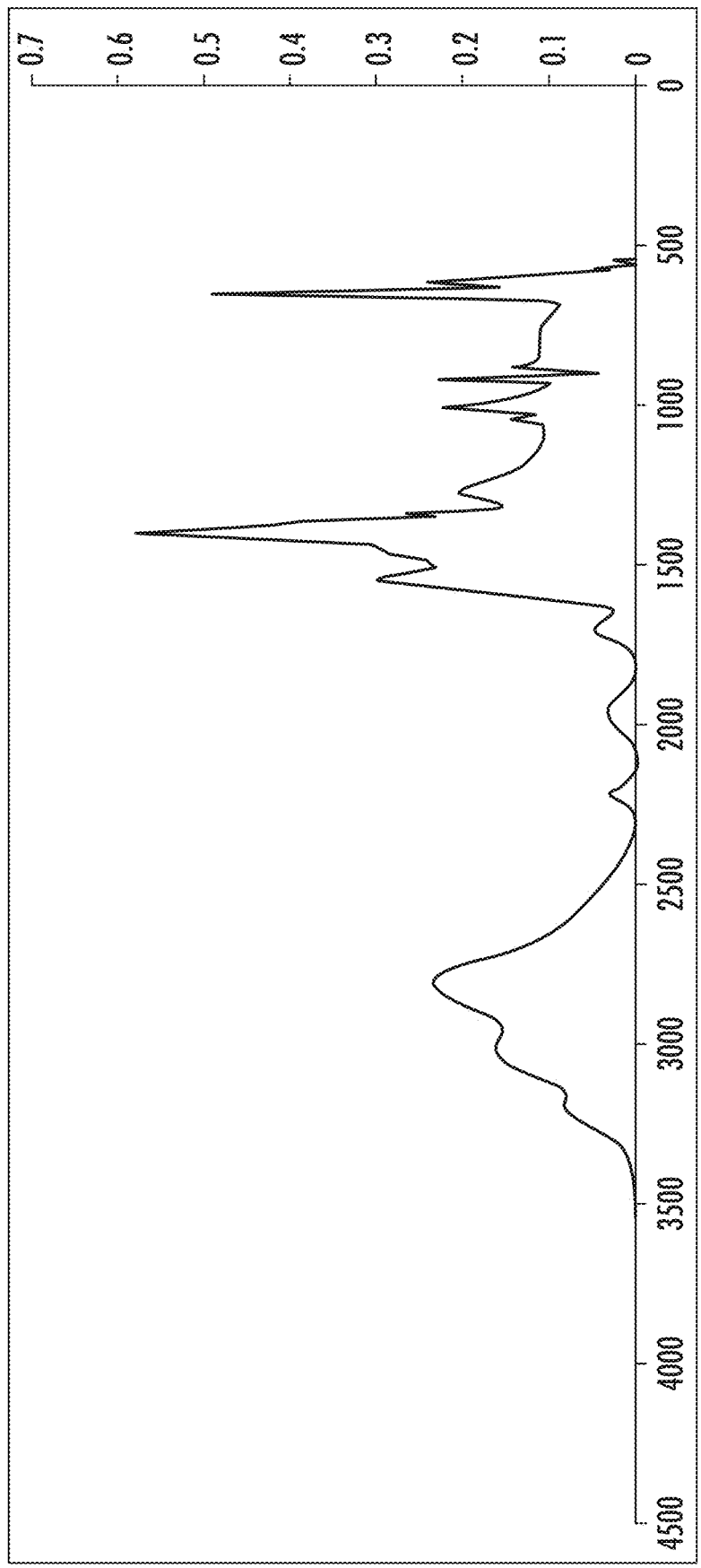
Figure 20:
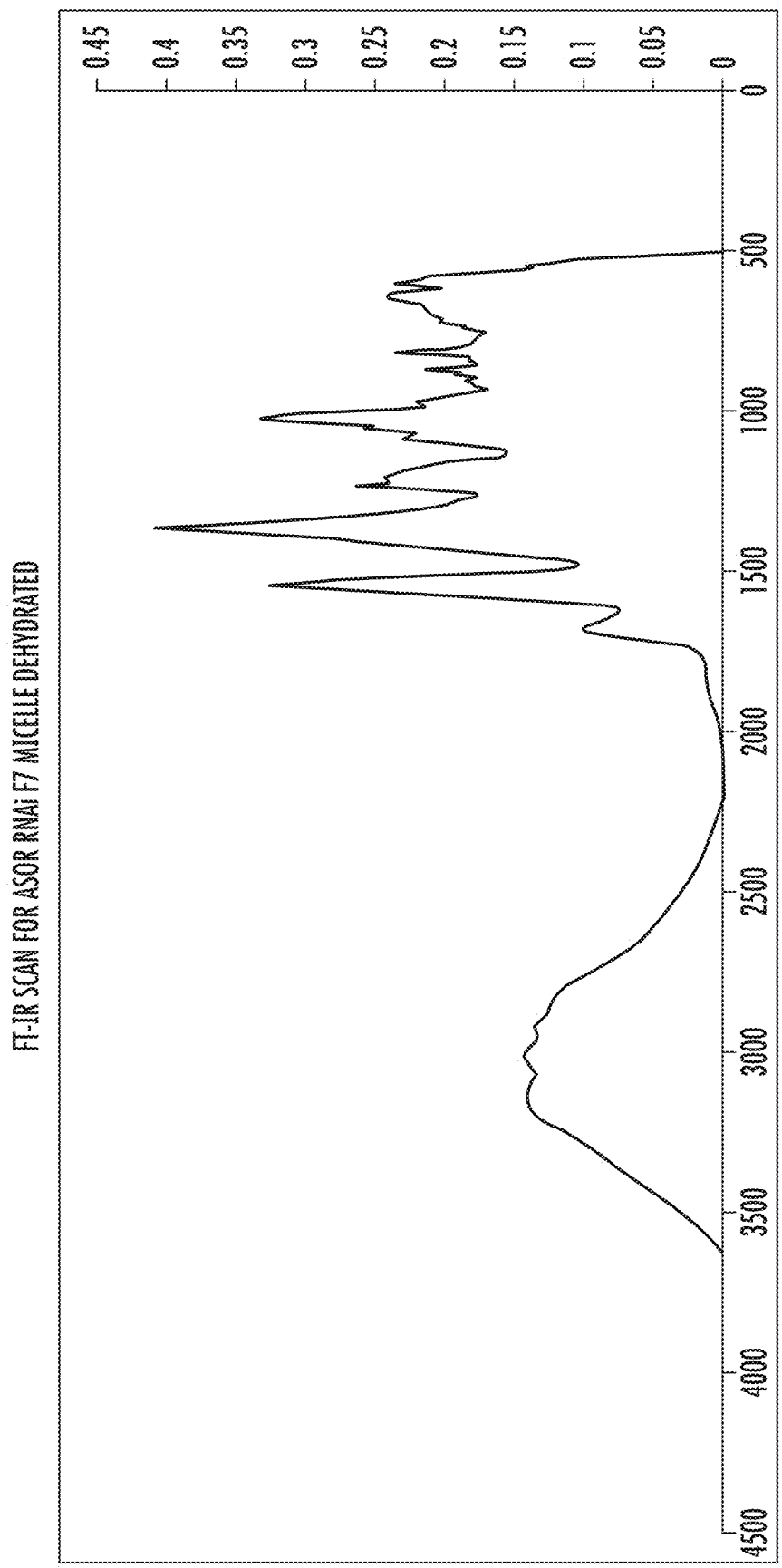
Figure 21:
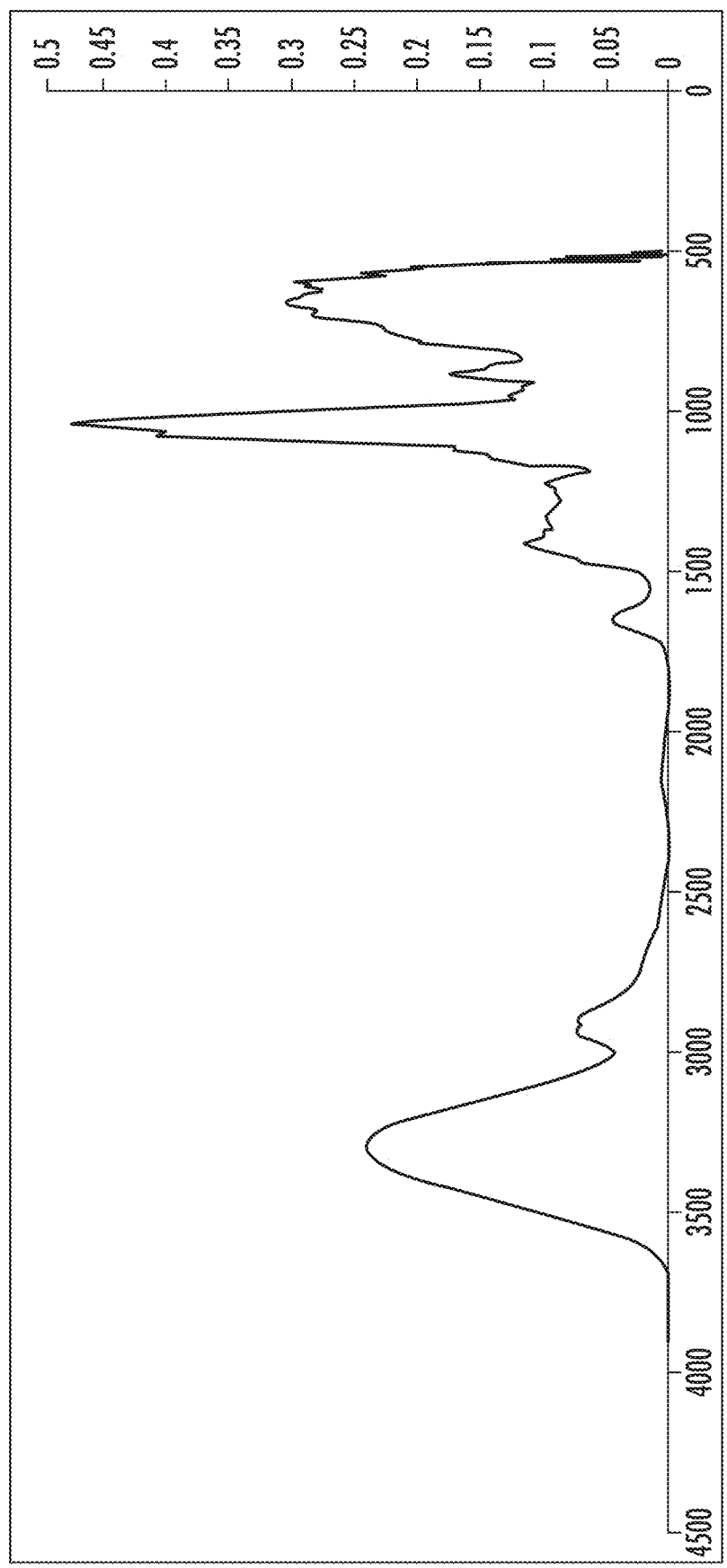
Figure 22:
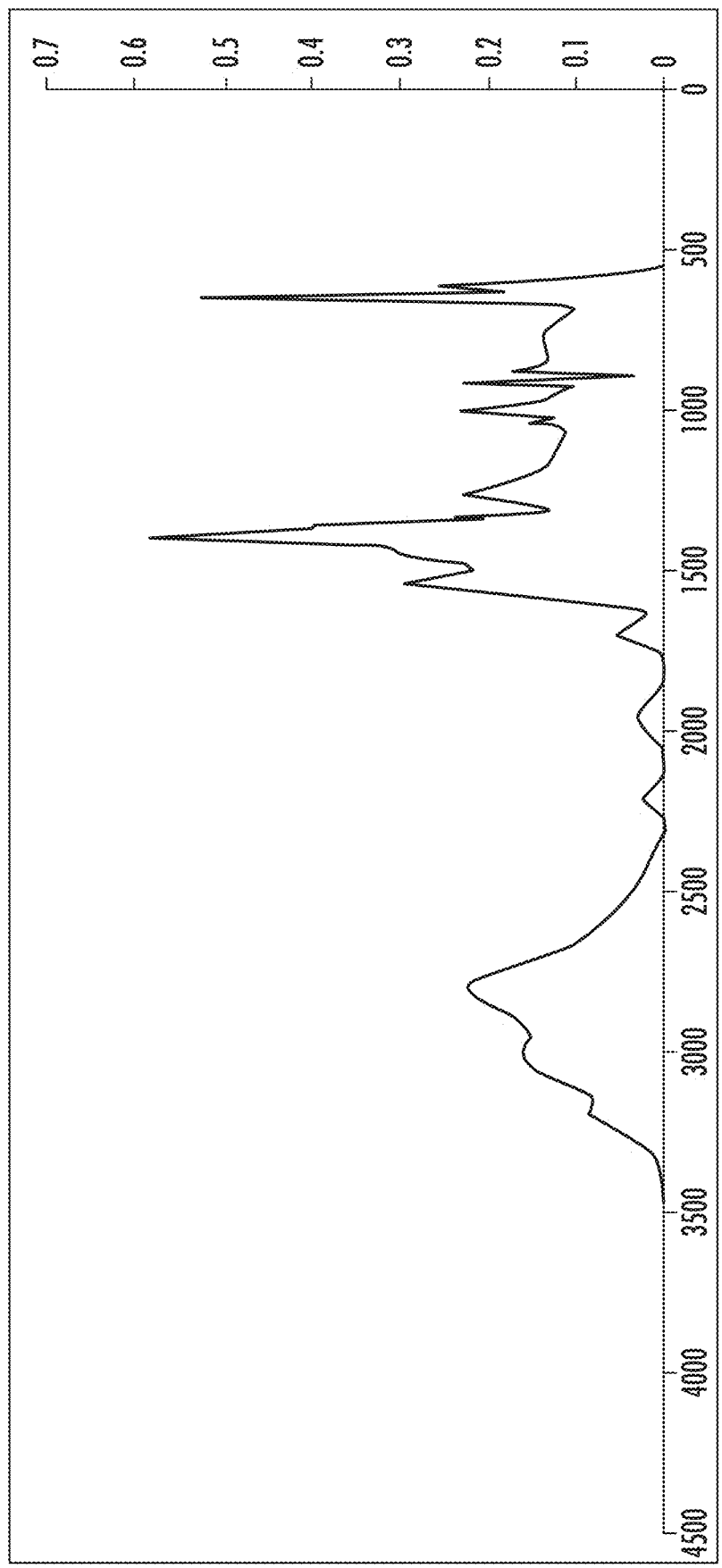
Figure 23:
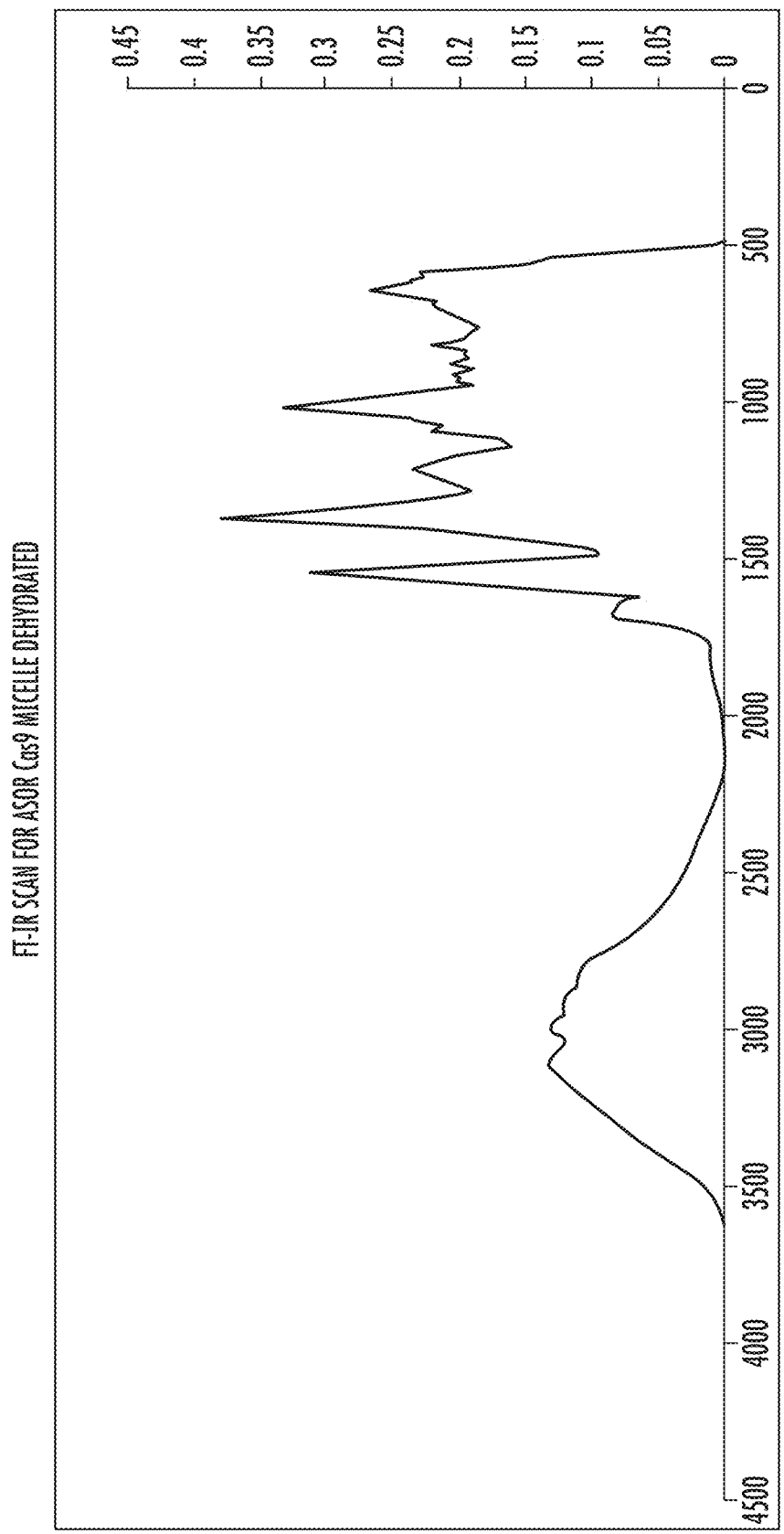
Figure 24:
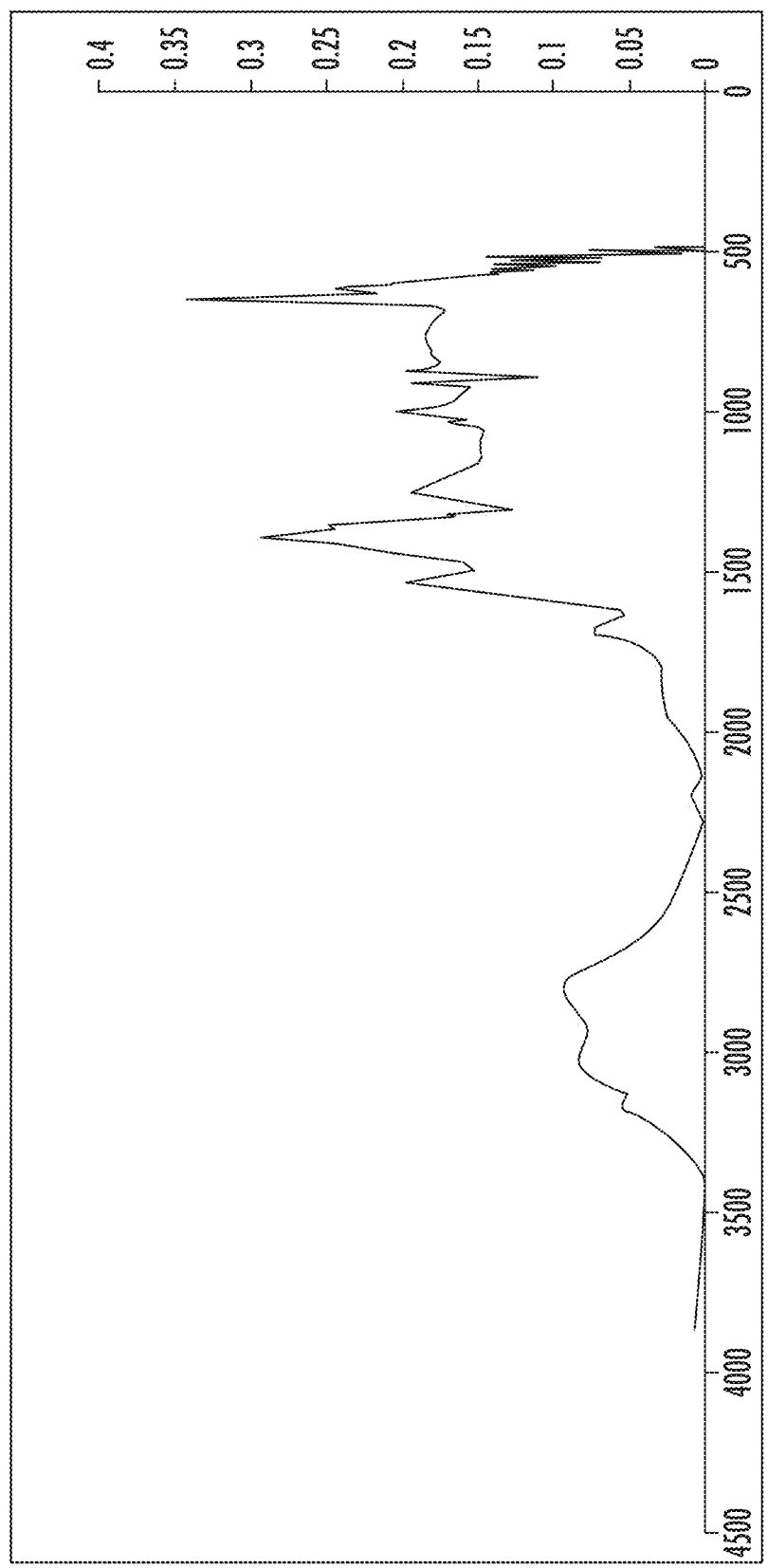
Figure 25:
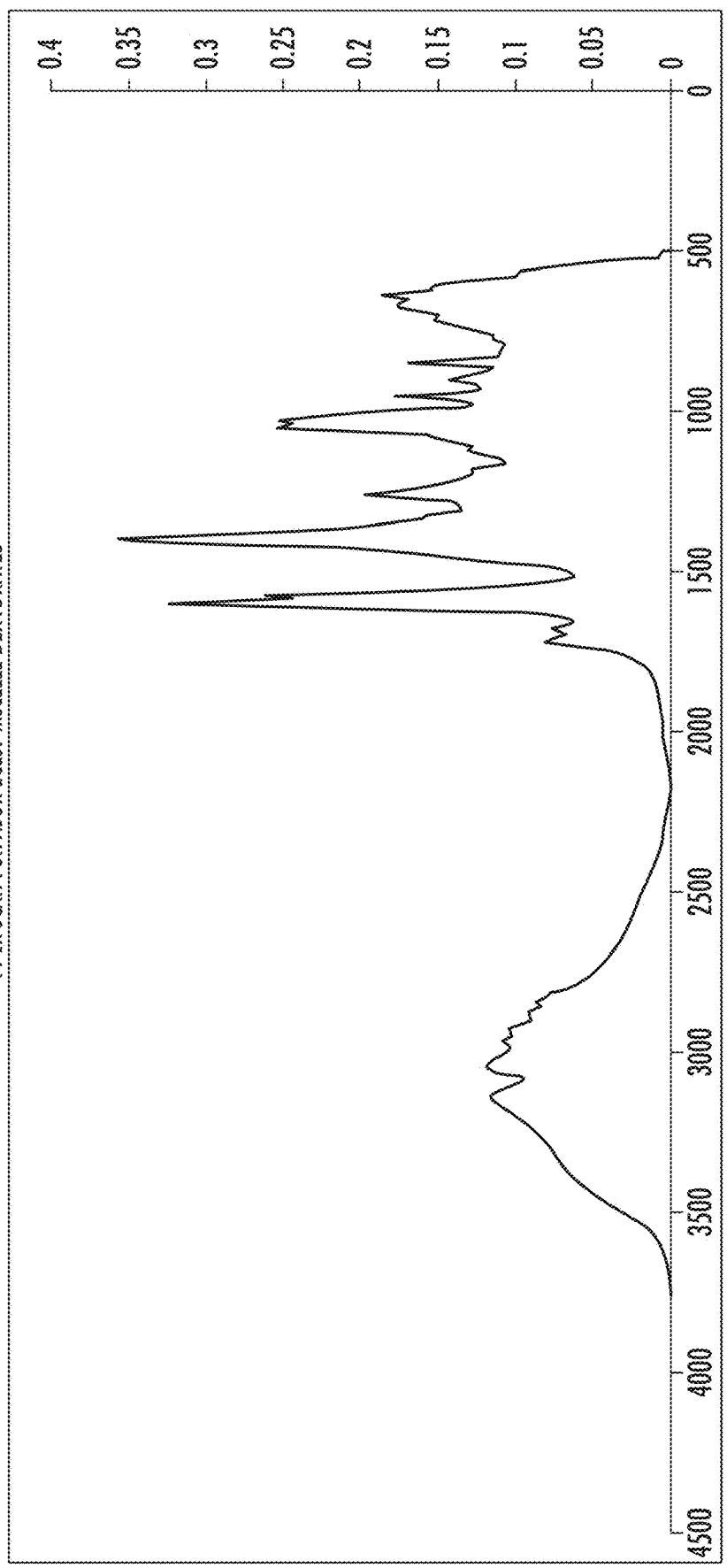
Figure 26:
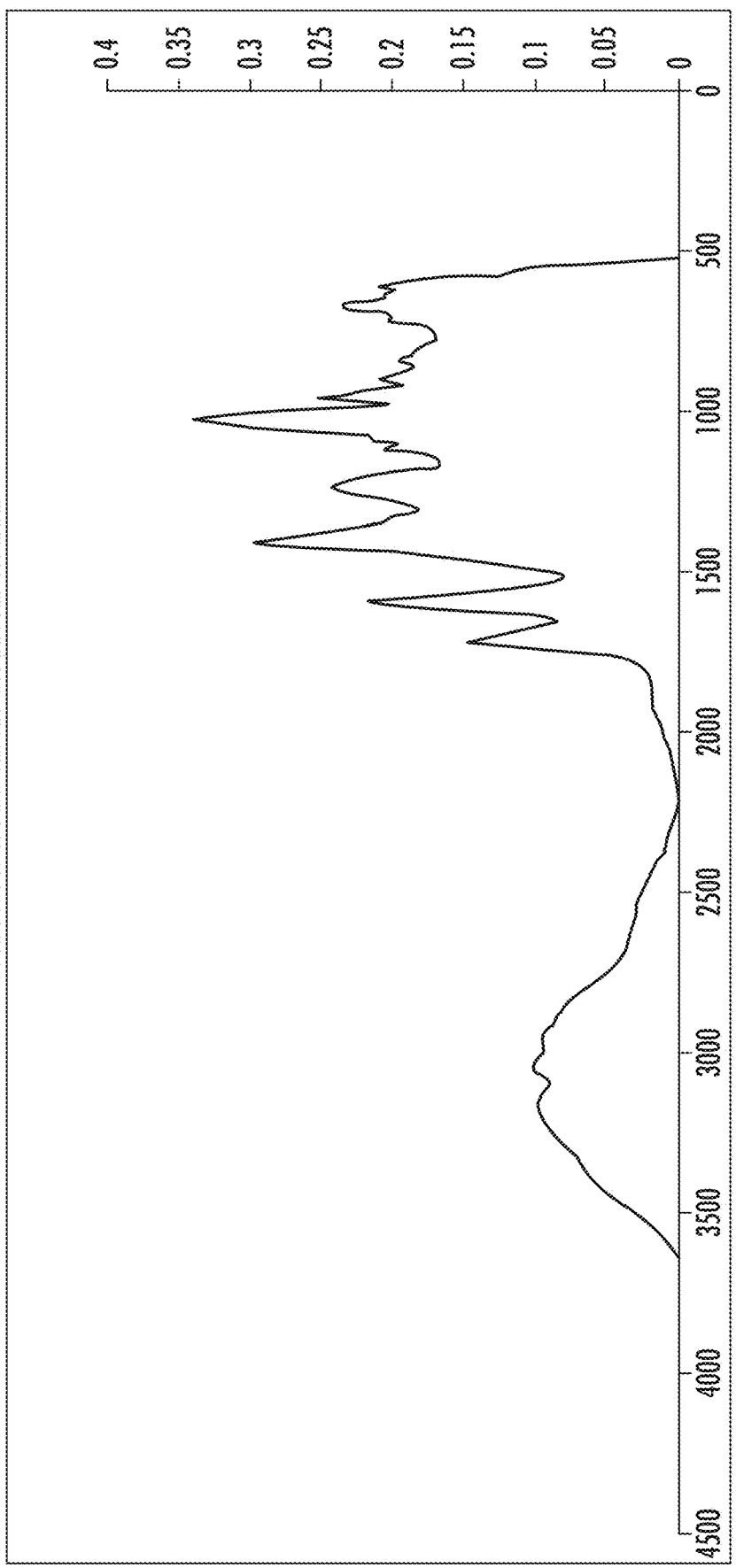
Figure 27:
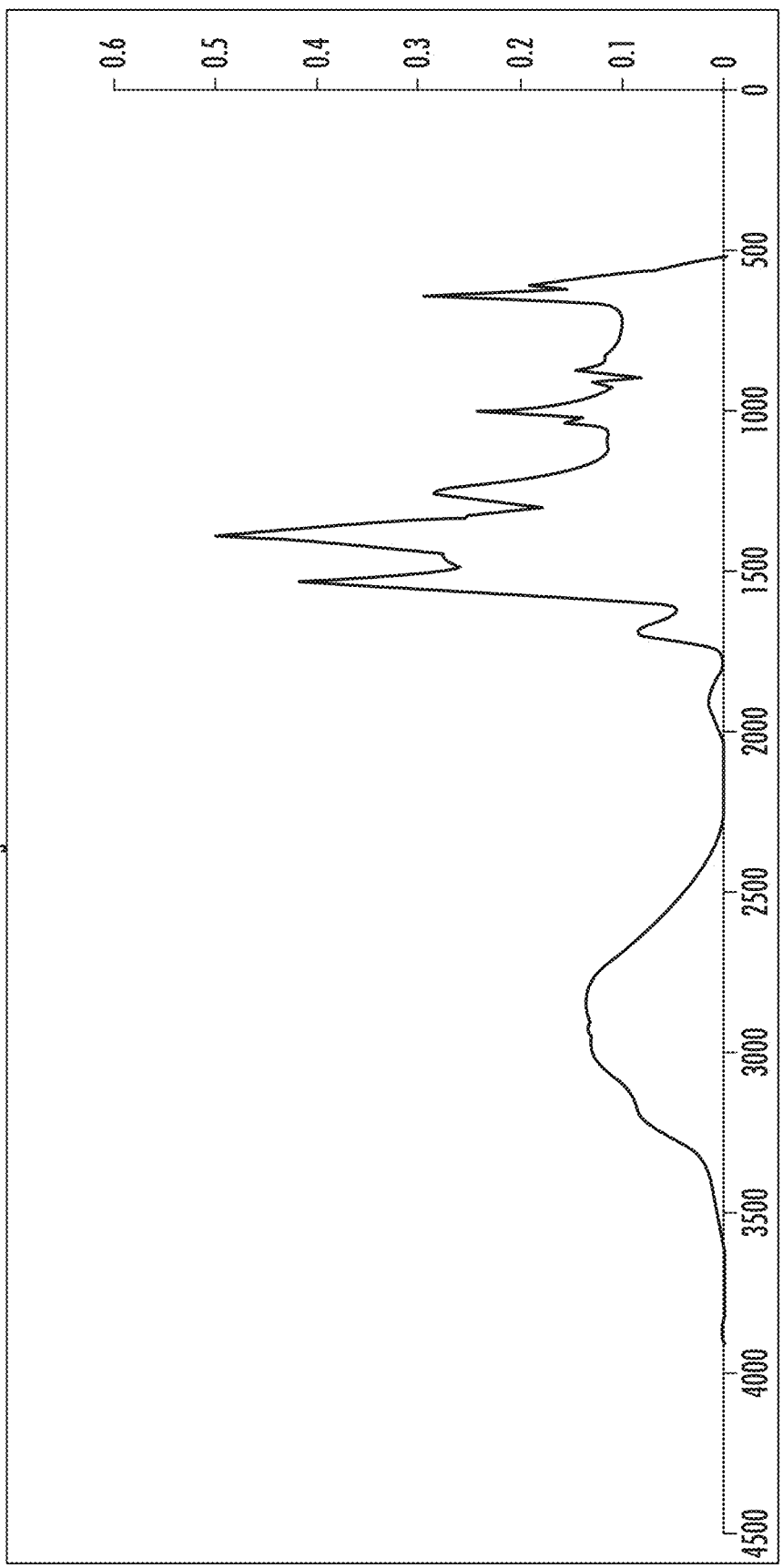
Figures 28, 29:
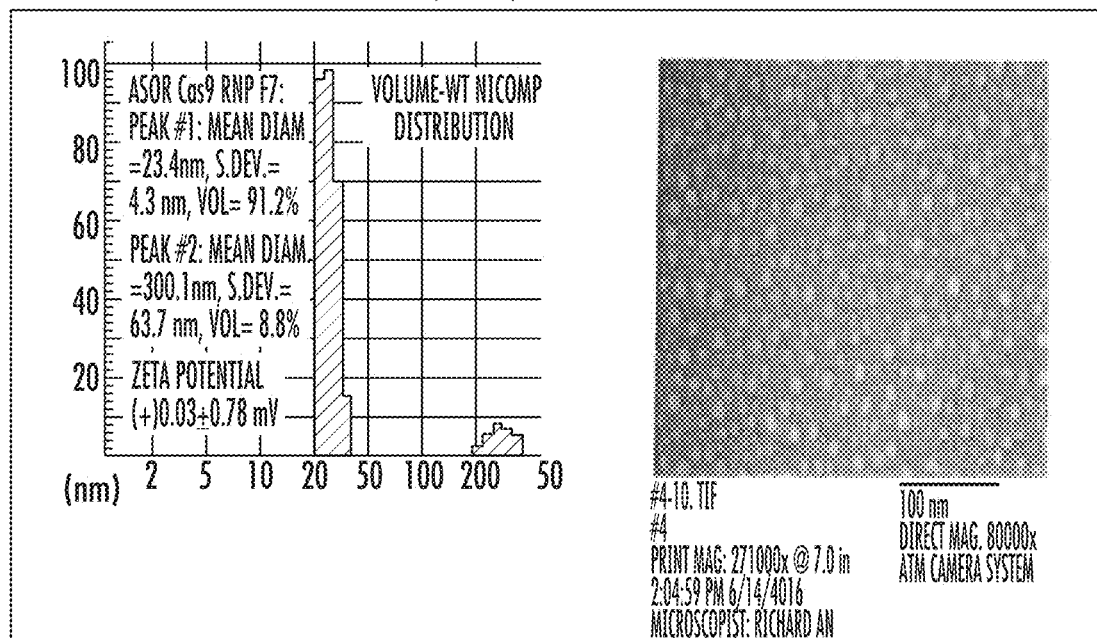
Figure 30:
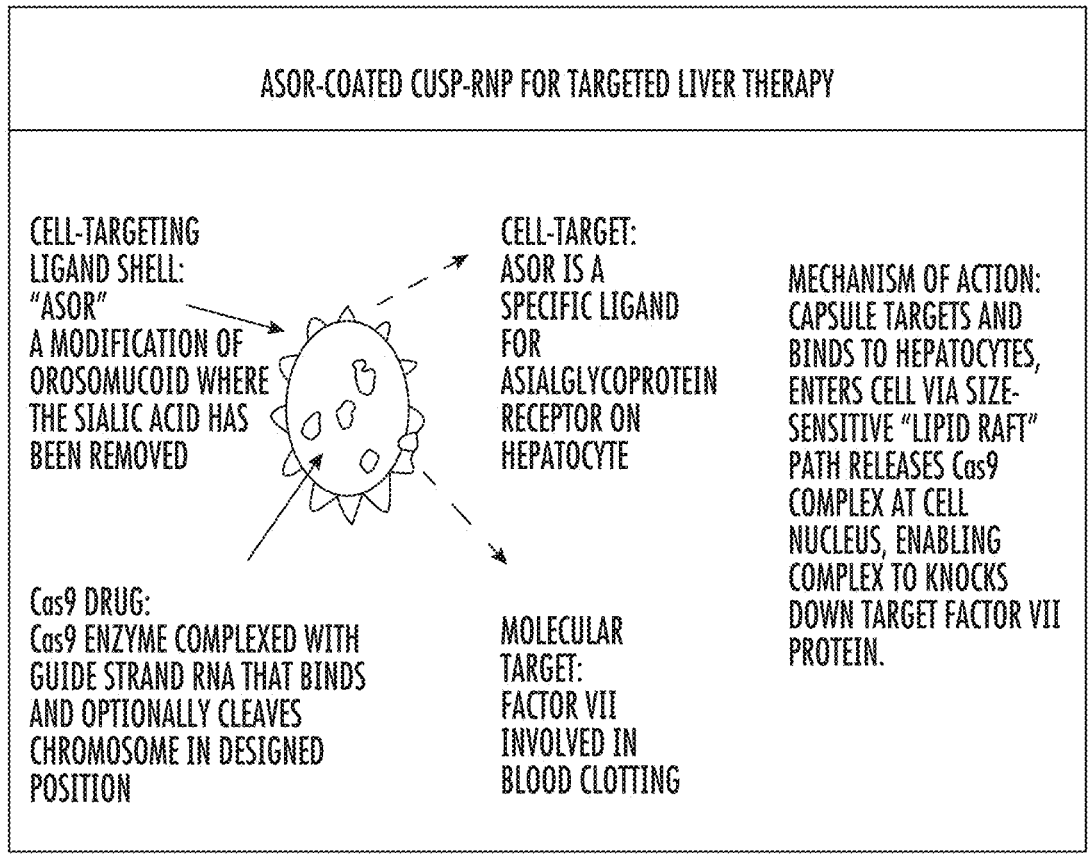
Figure 31:
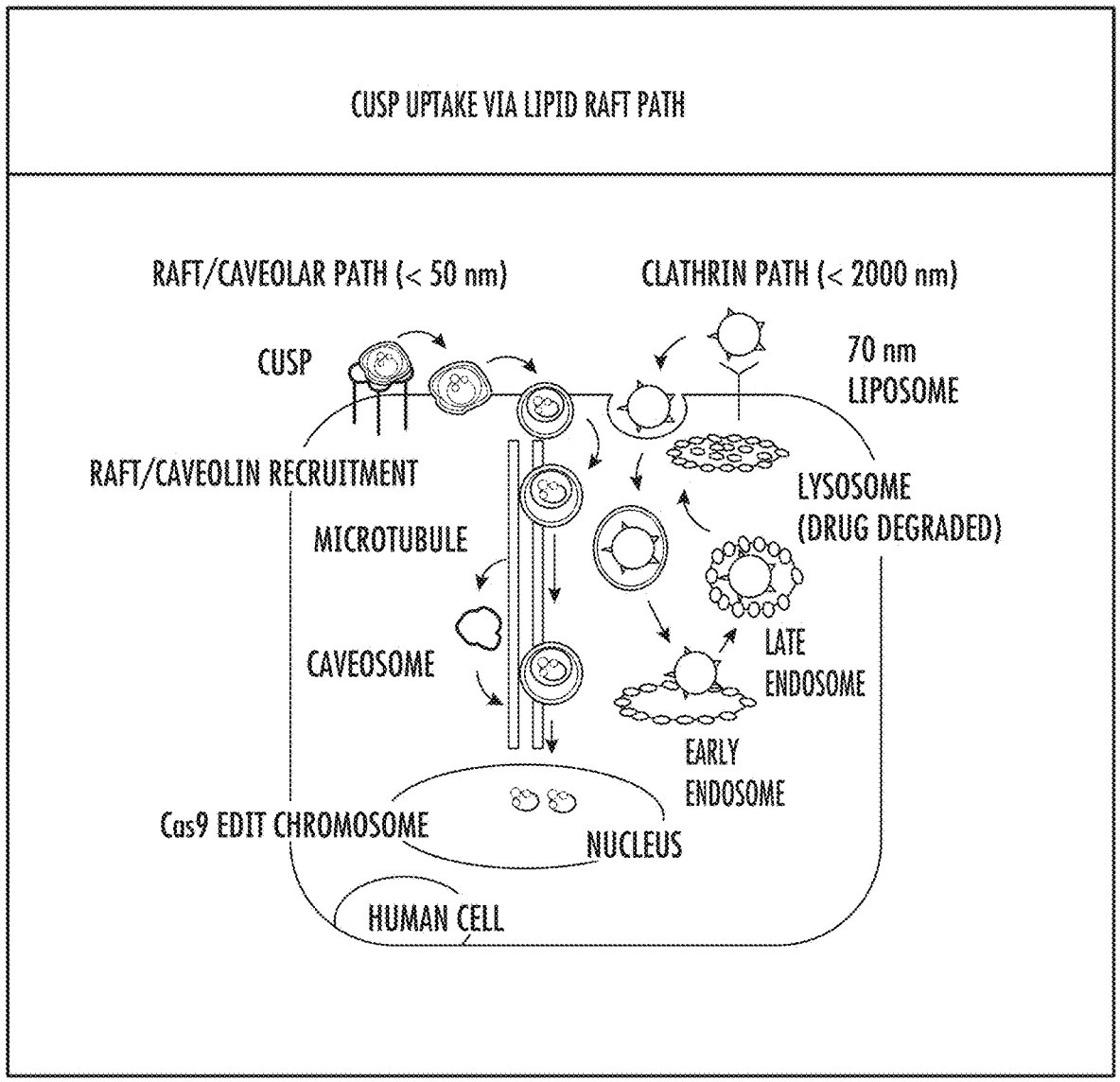
Figure 32:
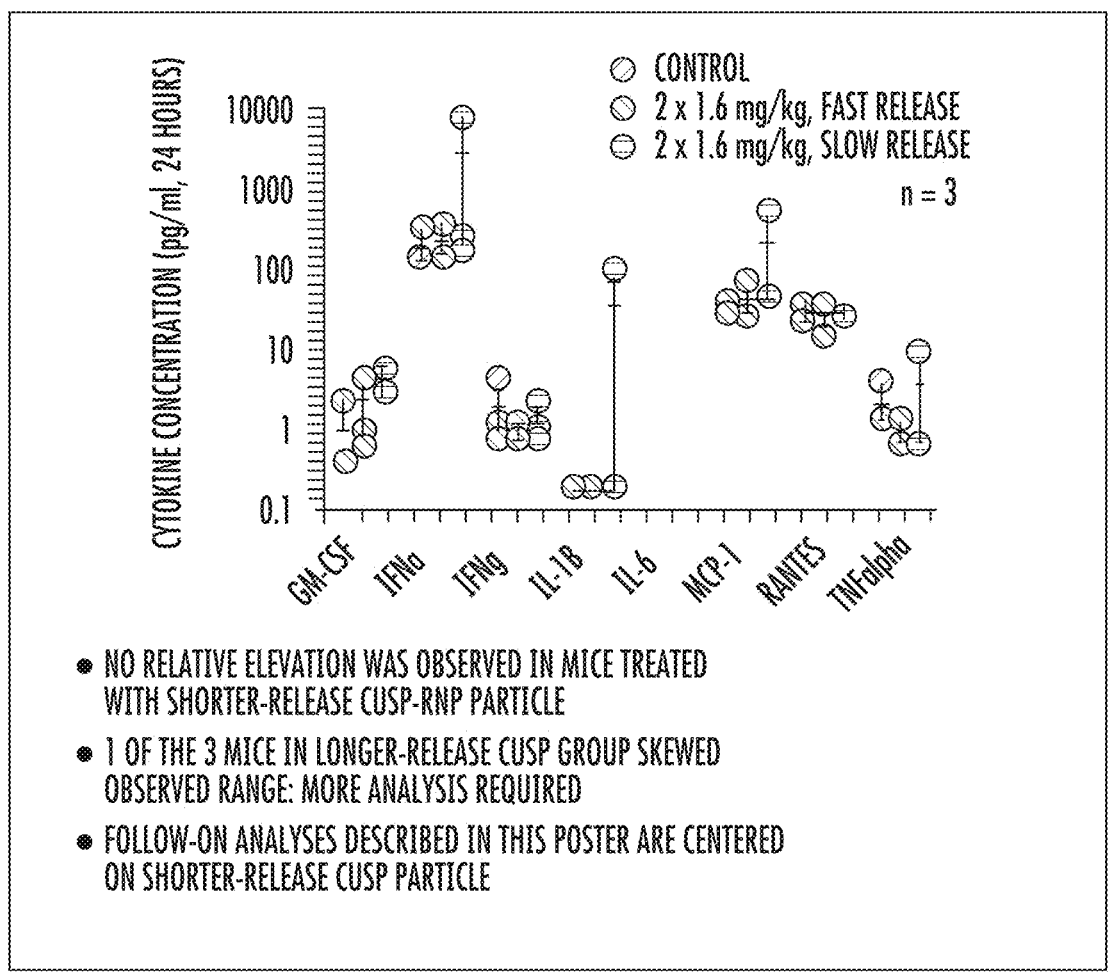
Figure 33:
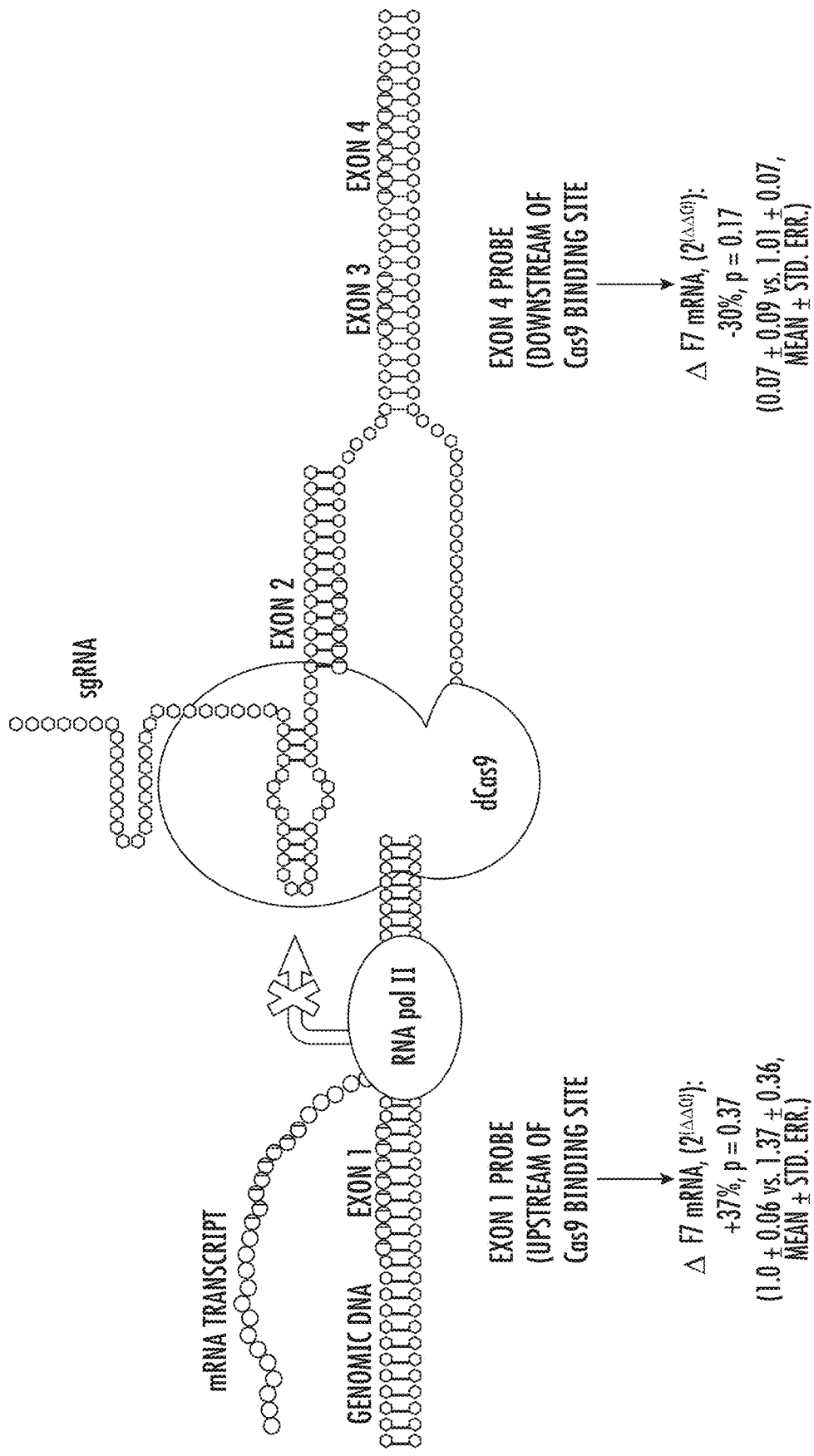
Figure 34:
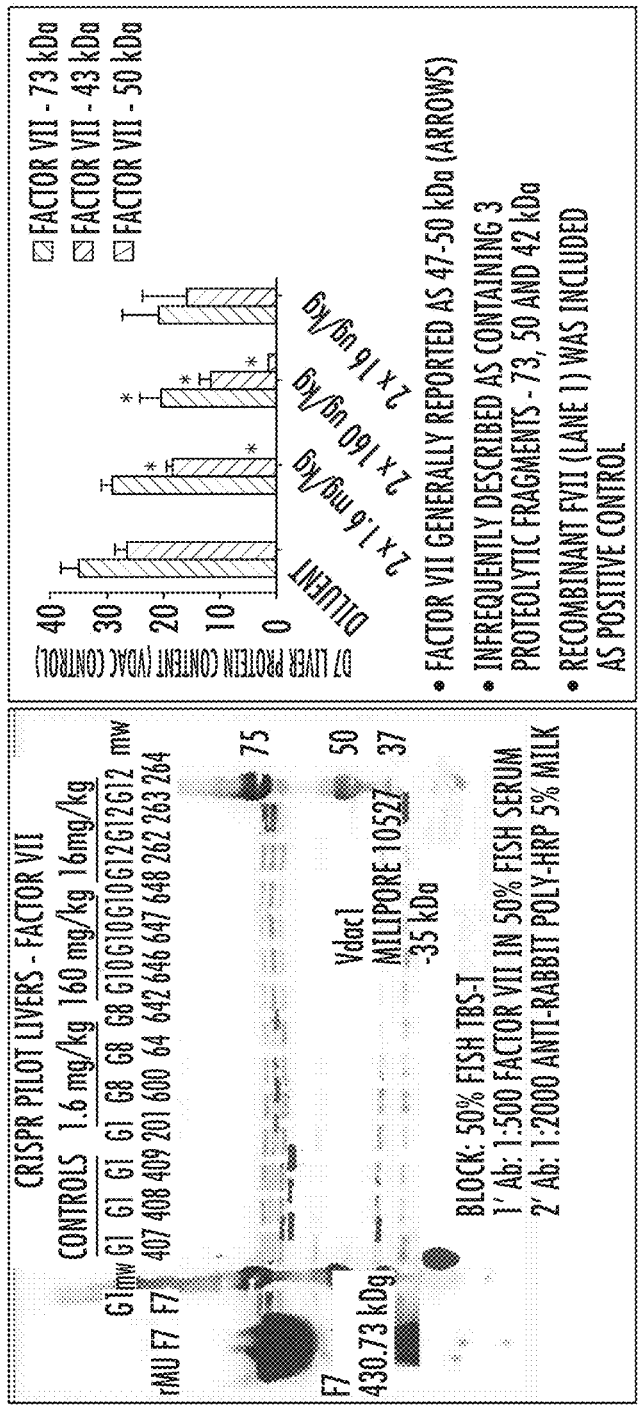
Figure 35A:
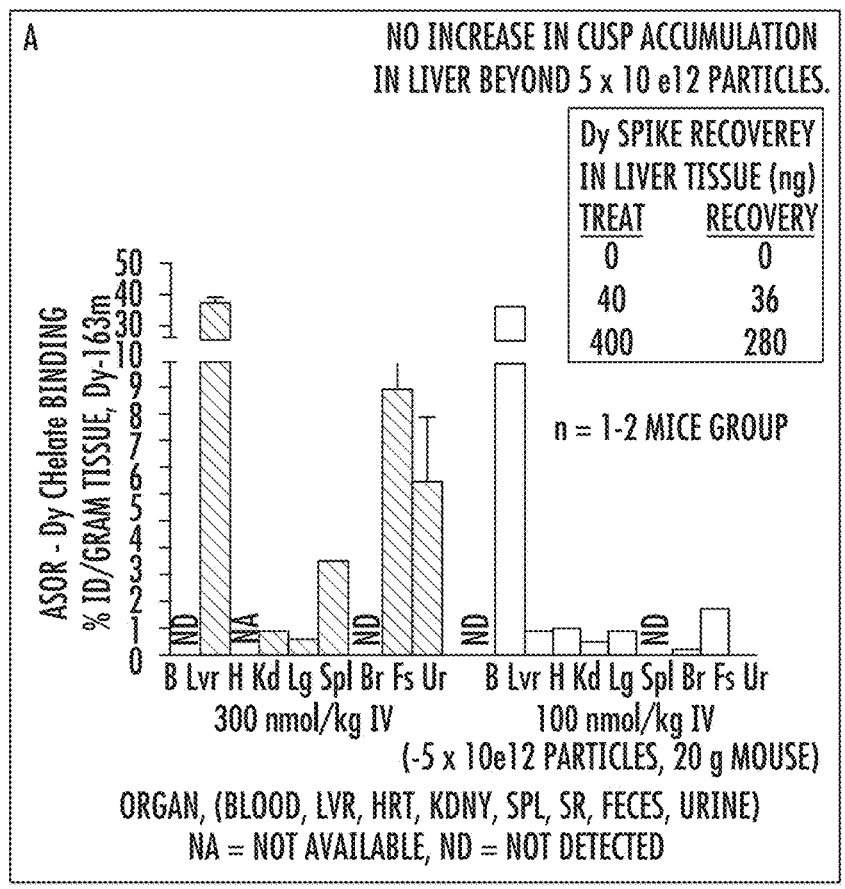
Figure 35B:
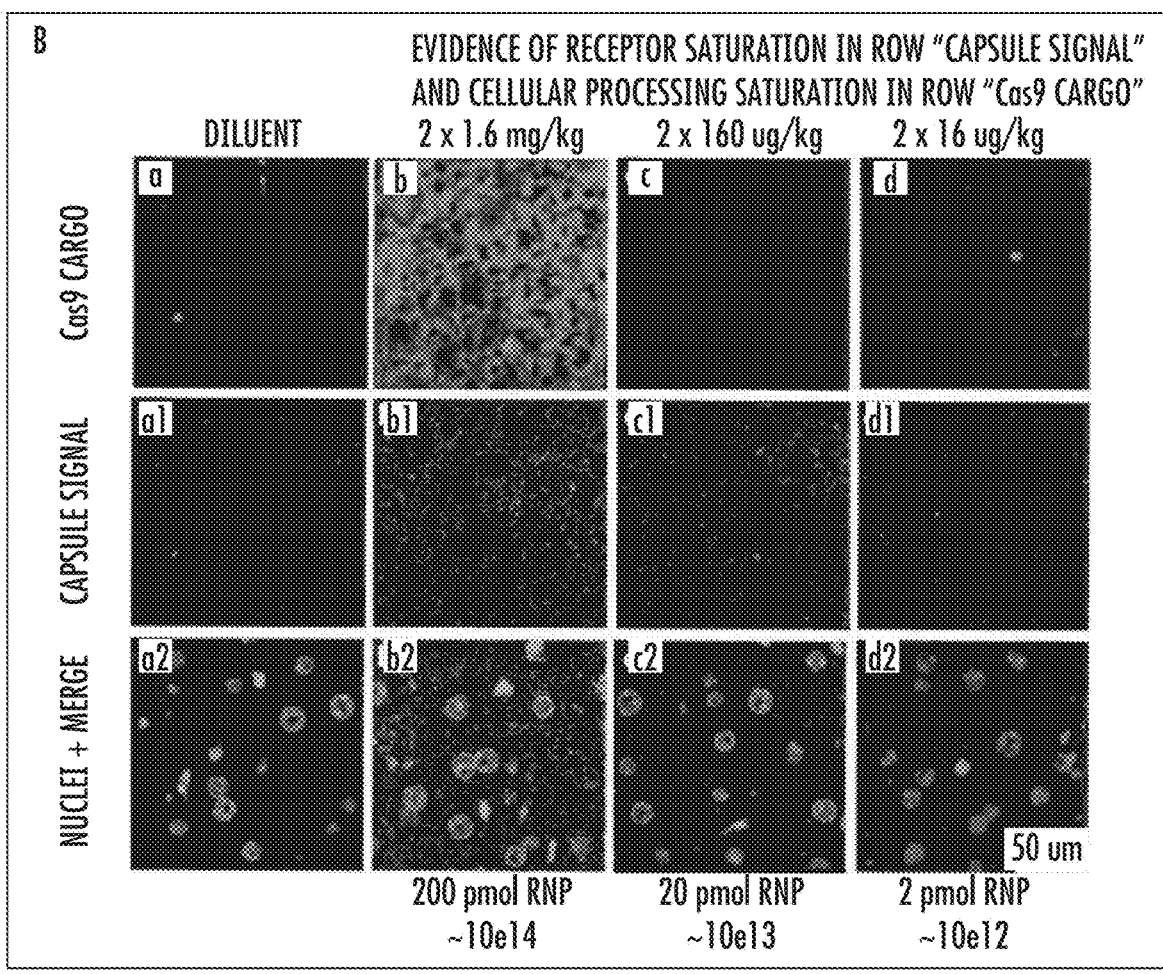
Figure 38:
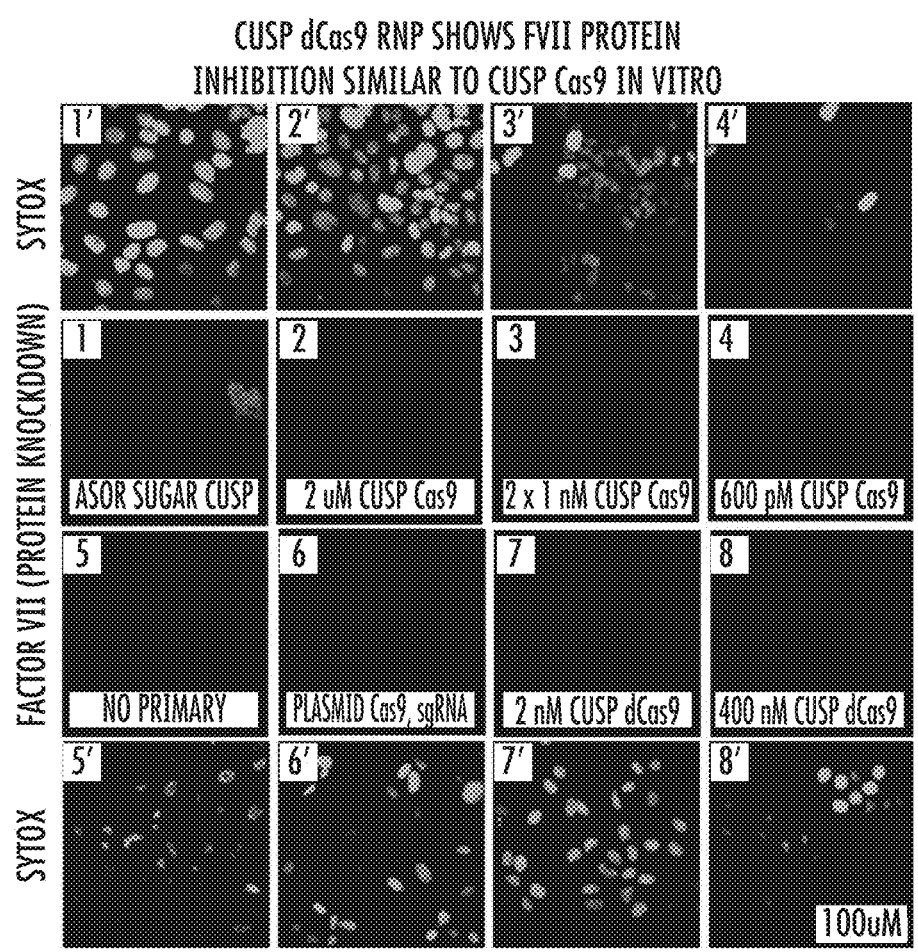
Figure 39:
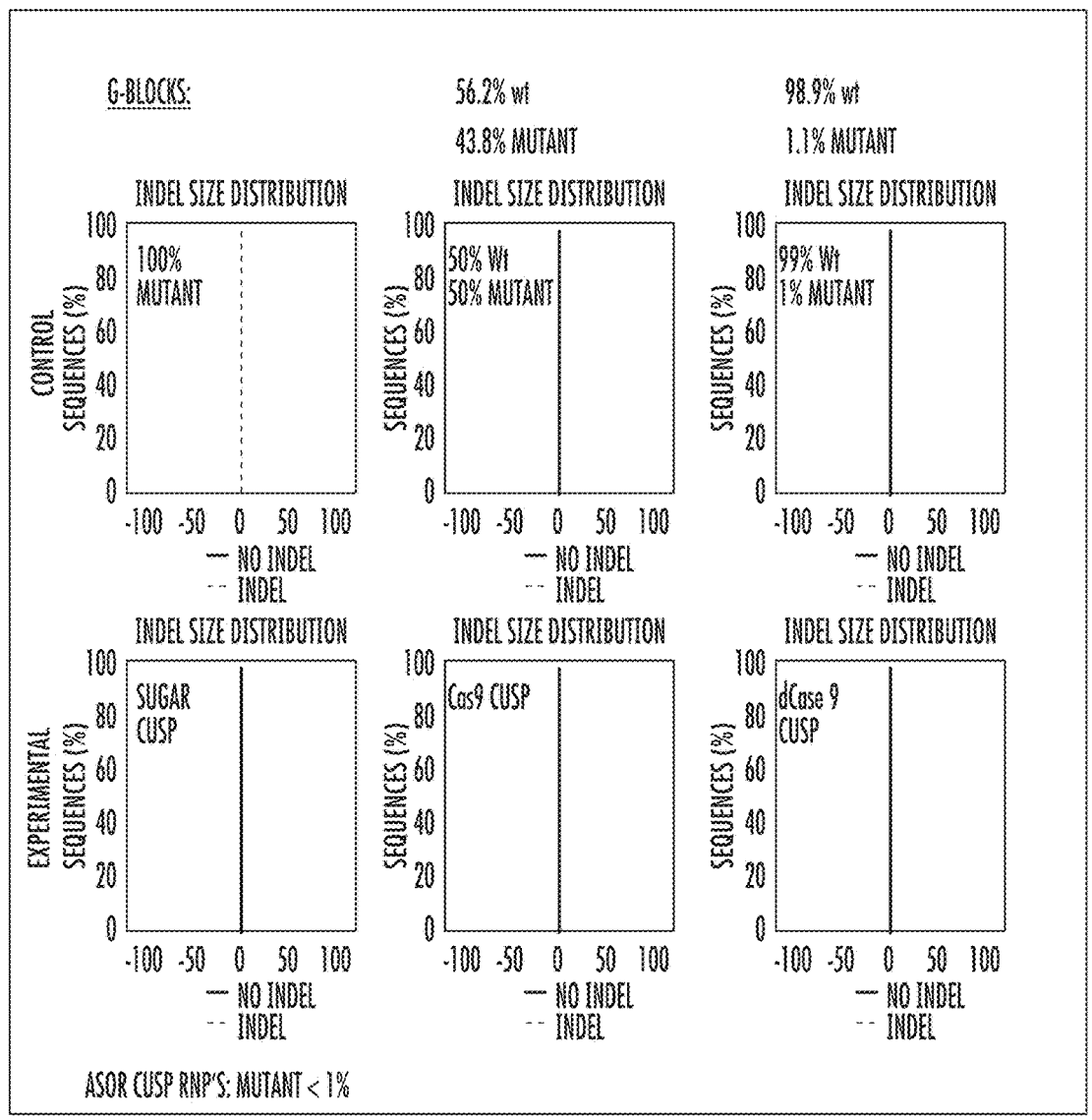

FIG. 11.5 shows TM-Diol Surfactant in 50% DMSO;

FIG. 12 shows FT-IR Scan for Ammonium Acetate Dried;

FIG. 13 shows FT-IR Scan for ASOR Sugar Nanocapsule hydrated;

FIG. 13-2 shows FT-IR Scan for ASOR Sugar Dried Only 2nd Run;

FIG. 14 shows FT-IR Scan for ASOR Sugar Nanocapsule dehydrated;

FIG. 15 shows FT-IR Scan for ASOR Sugar Micelle dehydrated;

FIG. 16 shows FT-IR Scan for ASOR RISC RNAi F7 Nanocapsule dehydrated;

FIG. 17 shows FT-IR Scan for ASOR RISC RNAi F7 Micelle;

FIG. 18 shows FT-IR Scan for ASOR RISC 2RF7 Micelle;

FIG. 19 shows FT-IR Scan for ASOR RNAi F7 Nanocapsule dehydrated;

FIG. 20 FT-IR Scan for ASOR RNAi F7 Micelle dehydrated;

FIG. 21 shows FT-IR Scan for ASOR Cas9 F7 Nanocapsule hydrated;

FIG. 22 shows FT-IR Scan for ASOR Cas9 F7 Nanocapsule dehydrated;

FIG. 23 shows FT-IR Scan for ASOR Cas9 Micelle dehydrated;

FIG. 24 shows FT-IR Scan for ASOR dCas9 F7 Nanocapsule dehydrated;

FIG. 25 shows FT-IR Scan for ASOR dCas9 Micelle dehydrated;

FIG. 26 shows FT-IR Scan of TBG Erythitol Nanocapsule hydrated;

FIG. 27 shows FT-IR Scan Tbg Erythritol Nanocapsule dehydrated;

FIG. 28 shows "short-release" (in vivo) CUSP-RNP particle DLS and TEM;

FIG. 29 shows CUSP RNP pilot study in mice;

FIG. 30 shows ASOR-coated CUSP-RNP for targeted liver therapy;

FIG. 31 shows CUSP-mediated RNP delivery into target cells via non-endosomal lipid raft path;

FIG. 32 shows cytokine levels of mice treated with CUSP-RNP at highest doses: fast+slow release particles;

FIG. 33 shows transcript changes observed via qPCR for Group 10, but differed based on probe set design;

FIG. 34 shows CUSP RNP knocks down FVII protein in RNP pilot study in vivo;

FIG. 35A shows isotopic bio distribution study in mice, utilizing CUSP-encapsulated Dy-Dextran;

FIG. 35B shows co-localization of spCas9 protein cargo (blue) and immuno-labeled CUSP shell;

Figures 36, 37:
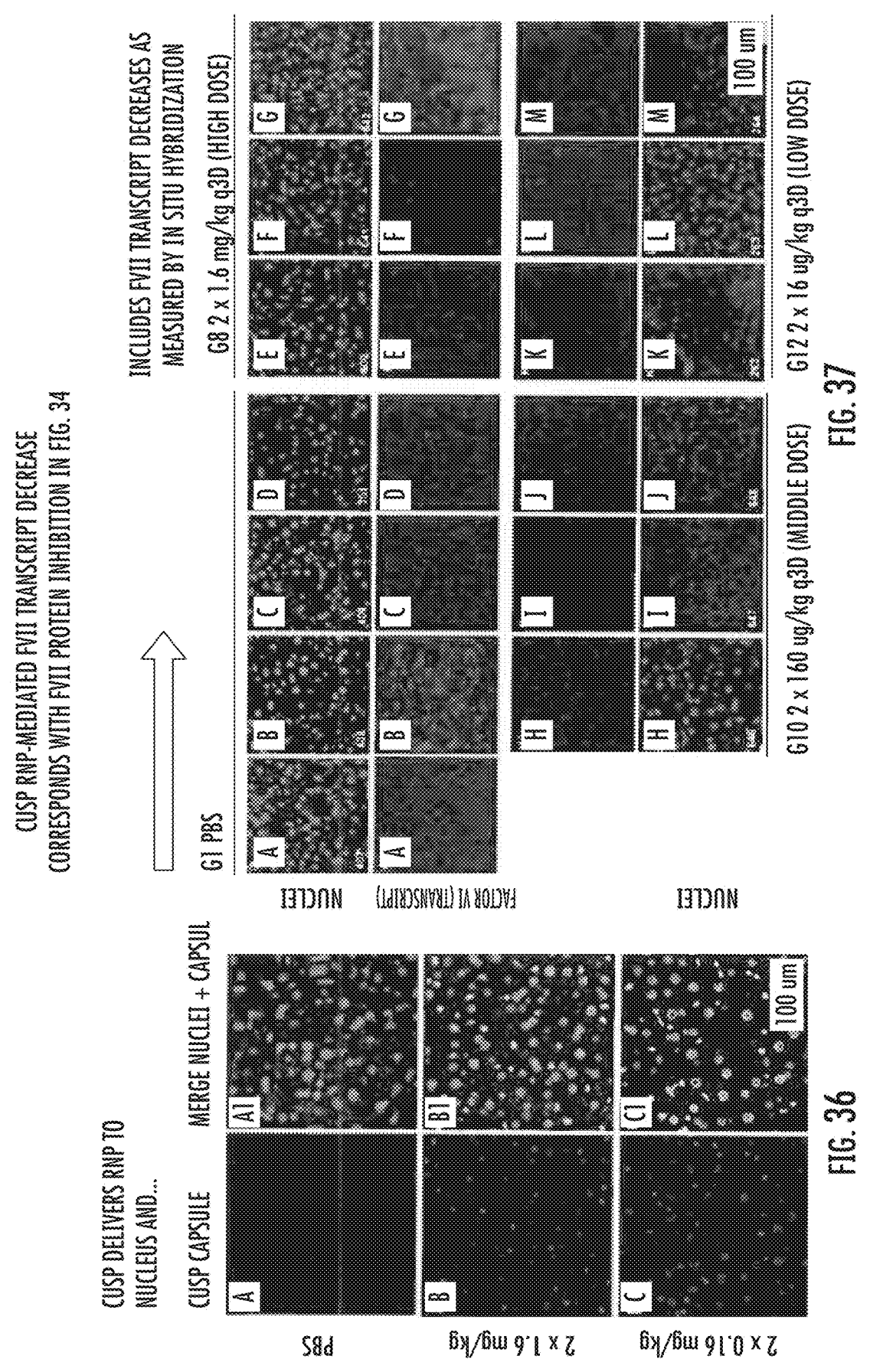

FIG. 36 shows CUSP delivers RNP to nucleus;

FIG. 37 shows CUSP-RNP induces FVII transcript decrease as measured by in situ hybridization;

FIG. 38 shows CUSP dCas9 RNP shows FVII protein inhibition similar to CUSP Cas9 RNP in vitro; and FIG. 39 shows neither dCas9 or Cas9 species shows mutational activity by amplicon deep sequencing;

VI. DETAILED DESCRIPTION OF THE INVENTION

By way of illustrating and providing a more complete appreciation of the present invention and many of the attendant advantages thereof, the following detailed description and examples are given concerning the nanoparticles, nanoparticle compounds, compositions, methods of manufacture and methods to deliver biological or other agents of the present invention.

As used here, the following definitions and abbreviations apply:

ASOR means asialoorosomucoid.

AGO means Argonaute and refers to, by way of non-limiting examples, the mammalian Argonaute protein family currently known in the art to consist of eight members, four of which are ubiquitously expressed (Ago subfamily), with the remaining four (Piwi subfamily) being expressed in germ cells. Similarly, Ago2 is useful in the instant invention in gene silencing independent of such cleavage activity, such as in translational repression. Argonaute can be an *Aquifex aeolicus*, a *Microsystis aeruginosa*, a *Clostridium bartlettii*, an *Exiguobacterium*, an *Anoxybacillus flavithermus*, a *Halogeometricum borinquense*, a *Halorubrum lacusprofundi*, an *Aromatoleum aromaticum*, a *Thermus thermophilus*, a *Synechococcus*, a *Synechococcus elongatus*, or a *Thermosynechococcus elogatus* Argonaute. Argonaute can be mammalian Argonaute, such as mouse AGO2. Argonaute can refer to the wild-type or a modified form of the Argonaute protein that can comprise an amino acid change such as a deletion, insertion, substitution, variant, mutation, fusion, chimera, or any combination thereof. The proteins referred to herein may also be identified by their NCBI accession numbers; Ago 1, NP-036331; Ago2, NP-036286, Ago3, NP-079128, and Ago4, NP-060099.

Biologic agents of the instant invention are, by way of non-limiting example, gene editing agents, agents that affect or modulate transcription or translation, guided endonuclease machinery, or agents that cause other genetic or biochemical changes in a biologic system.

Cas protein, or Cas, refers to CRISPR-associated proteins and by non-limiting examples, Cas9 proteins, Cas9-like proteins encoded by Cas9 orthologs, Cas9-like synthetic proteins, Cpf1 proteins, proteins encoded by Cpf1 orthologs, Cpf1-like synthetic proteins, C2c1 proteins, C2c2 proteins, C2c3 proteins, and variants and modifications thereof. In a preferred embodiment, a Cas protein is a Class 2 CRISPR-associated protein, for example a Class 2 Type II CRISPR-associated protein or a Class 2 Type V CRISPR-associated protein. Each CRISPR-Cas protein interacts with one or more cognate polynucleotide (typically RNA) to form a nucleoprotein complex (typically a ribonucleoprotein complex).

Cas9 protein (or Cas9) as used herein refers to a Cas9 wild-type protein derived from Type II CRISPR-Cas9 systems, modifications of Cas9 proteins, variants of Cas9 proteins, Cas9 orthologs, and combinations thereof. The term "dCas9" as used herein refers to variants of Cas9 protein that are nuclease-deactivated Cas9 proteins, also termed "catalytically inactive Cas9 protein," or "enzymatically inactive Cas9."

Chimeric refers a molecule that is composed of both RNA and DNA moieties that are naturally occurring or nucleotide analogs, linked by phosphodiester, phosphorothioate, and/or any other naturally occurring or synthetic linkage that permits the nucleotides or analogs to retain their intended function.

Cognate, as used here, typically refers to a Cas protein and one or more Cas polynucleotides that are able of forming a nucleoprotein complex capable of site-directed binding to a target nucleic acid complementary to the target nucleic acid binding sequence present in one of the Cas polynucleotides.

Cpf1 protein refers to a Cpf1 wild-type protein derived from Type V CRISPR-Cpf1 systems, modifications of Cpf1 proteins, variants of Cpf1 proteins, Cpf1 orthologs, and combinations thereof. The term "dCpf1" as used herein refers to variants of Cpf1 protein that are nuclease-deactivated Cpf1 proteins, also termed "catalytically inactive Cpf1 protein", or "enzymatically inactive Cpf1".

CRISPR means clustered regularly interspaced short palindromic repeats.

dCas9 means endonuclease dead Cas9, also known as dead Cas9 and is a mutant form of Cas9 whose endonuclease activity is removed through point mutations in its endonuclease domains.

DLS means Dynamic Light Scattering and, in connection with data shown herein, means a Nicomp ZLS 380 instrument.

Donor template DNA, in reference to CRISPR technology or RISC technology or, means DNA that is configured to provide a template for DNA synthesis in regions that have been excised by CRISPR technology or RISC technology.

DTT means dithiothreitol.

Flag means FLAG-tag comprising the amino acid residues DYKDDDDK.

fpm means feet per minute.

Gene editing, as used herein, refers to the insertion, deletion or replacement of nucleic acids in genomic DNA so as to add, disrupt or modify the function of the product that is encoded by a gene.

"Guide strand" refers to the single-stranded polynucleotide that comprises at least 12 nucleotides that binds to an Argonaute polypeptide or a related RISC complex and is capable of directing NP complex to a target polynucleotide. The guide molecule can be a DNA or an RNA or a chimeric molecule. The skilled artisan, with the teaching herein, is readily able to design the guide strand, typically optimizes for uniform hybridization energies across sequences at sites of low target mRNA secondary structure while siRNA design is more focused on optimizing a hybridization profile across the sequence within the context of sequence "rules". Design algorithms such as Soligo for antisense and SiRNA for siRNA are publicly available.

In concert (as a biologic agent) means performing a biologic function together as part of a complex or physical association or interaction such as that which occurs in substrate-enzyme binding or other physicochemical interactions.

Instant means, by way of non-limiting examples, when used as is "instant nanoparticles" or "instant ligands" means the nanoparticles or ligands of the present invention.

NP means nucleoprotein complex which is a polynucleotide-protein complex. By non-limiting examples of such complexes are Cas-sgRNA, RISC, PNA, and SGN complexes. Typically, the polynucleotide portion is an RNA species, although DNA-protein complexes and chimeric nucleic acid polymers are also contemplated here.

PNA means Triplex-forming peptide nucleic acid oligomers. PNAs refer to complexes in which, by way of non-limiting example, the phosphate backbone of polynucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that are similar to polynucleotides, but are achiral and neutrally charged molecules. Peptide nucleic acids are comprised of peptide nucleic acid monomers. PNA complexes have a charge-neutral peptide-like backbone and nucleobases enabling hybridization with DNA and RNA with high affinity. PNA/DNA/PNA triplexes recruit the cell's endogenous DNA repair systems to initiate site-specific modification of the genome when single-stranded "donor template DNAs" are co-delivered as templates containing the desired sequence modification. This technology, described by Rogers, et al., Proc. Natl. Acad. Sci. USA, 99:16695-16700 (2002) is also contemplated to be useful according to the present invention as taught by U.S. 20170283830. More recently, a review describing useful aspects of this technology has been published by Siddiquee et al. in Adv Tech Biol Med 2015, 3:2.

Polynucleotide, as used here, means a biopolymer composed of any number of nucleic acid monomer of deoxyribonucleic acid or ribonucleic acid and contemplates nature and modified or synthetic nucleic acid monomers. "Polynucleotide components", as used herein, means polynucleotides with the additional teaching set forth elsewhere herein.

rAgo2 means recombinant protein argonaute-2.

RISC as used herein means RNA-induced silencing complex and, by way of non-limiting example, a guide strand-AGO protein complex.

RISC nanoparticles means the instant nanoparticles wherein the biologic agent is a RISC.

RNAiF7 means a single stranded RNA polynucleotide complementary to Factor VII (i.e. a guide RNA).

RNP means ribonucleic protein.

sgRNA-Cas nanoparticles means the instant nanoparticles wherein the biologic agent is an sgRNA-Cas nucleoprotein complex.

siF7 means a double stranded siRNA complementary to Factor VII coding sequence.

SGN means the structure-guided endonuclease gene editing technology, for example, where the protein component is a FEN-1 fusion (endonuclease) and where the polynucleotide is a guide DNA. The guide DNA can be about 20 to about 50 nucleotides. The gene editing function of SGN is described, for example, in Xu S, Cao S, Zou B, Yue Y, Gu C, Chen X, et al. An alternative novel tool for DNA editing without target sequence limitation: the structure-guided nuclease (SGN). Genome Biol. 2016 and Varshney G K, Burgess S M. DNA-guided genome editing using structure-guided endonucleases. Genome Biology. 2016; 17:187. doi: 10.1186/s13059-016-1055-4.

sgRNA or gRNA means a single-guide RNA with about 20 nucleotides and directs Cas9 or dCas9 or other Cas proteins to their targets and together make up the whole or part of the CRISPR system.

Biologic Agents and Protein and Polynucleotide Components

Biologic agents can be any Biologic agent that comprises a protein component comprising one or more proteins and a polynucleotide component, comprising one or more polynucleotides, where the biologic activity of the biologic agent requires at least the co-action of the protein component and the polynucleotide component.

Examples of such biologic agents are RNA-induced silencing complexes ("RISC") which is a complex which incorporates one strand of a single-stranded RNA (ssRNA) fragment (such as microRNA [miRNA], or double-stranded small interfering RNA [siRNA]) and one or more specific RISC-associated proteins.

Other examples of such biologic agents are complexes between sgRNA and one or more CRISPR associated protein ("Cas").

Other examples are Triplex-forming peptide nucleic acid oligomers.

Other examples are guide nucleic acid and FEN-1 using the so-called structure-guided endonuclease technology.

By way of non-limiting example, protein and polynucleotide component pairs (capable of forming a biologic agent) of the instant invention comprise one or more of:

an argonaute protein and a guide strand where the guide strand is single stranded RNA (ssRNA);

an argonaute protein and a guide strand where the guide strand is a small interfering RNA (siRNA);

an argonaute protein and a guide strand where the guide strand is microRNA (miRNA);

a Cas9 protein and a sgRNA;

a Cas9 protein, an sgRNA, and a donor template DNA;

a dCas9 protein and an sgRNA;

a Cpf1 protein and a sgRNA;

a PNA; and/or

FEN-1 and a guide nucleic acid.

It should be further understood that the instant biologic agents are useful as therapeutic agents.

Biologic Agent Complex

Instant biologic agents are co-encapsulated according to the instant invention in a configuration that may or may not represent the configuration or complex structure that occurs in their physiologically-active state. For example, it is well understood that in RISC complexes and Cas-sgRNA complexes, there is a specific interaction between the protein components and the polynucleotide components that dictate their coordinate action. Nevertheless, this complex not only co-delivers the protein components and the polynucleotide components, these components are delivered in immediate, physical proximity to one another and provide a means for efficient transition to an optimal configuration. Moreover, when formed as taught herein, nanoparticles are made with superior efficacy and loading. For drafting convenience, the complex formed between the protein components and the polynucleotide components in the instant nanoparticles is also referred to as a "biologic agent".

The biologic agent of the instant invention may be formed by complexing the protein components and the polynucleotide components by methods described below and further in the Examples. However, with the teaching herein, the skilled artisan will readily appreciate useful modifications of these methods.

With regard to the complex formed between the polynucleotide component and the protein component as encapsulated in the nanoparticles, in some embodiments, this complex is of the manner an aggregate, meaning a heterogeneous interaction involving different interactions ranging from specific, high affinity interaction to non-specific interactions. In other embodiments, the complex is made of one or more specific interactions such as an enzyme binding to a substrate or a polymerase binding to a polynucleotide acid.

Preparation of Nanoparticles

The instant nanoparticles are produced as taught by the methodology, examples, and principles herein and also considering certain general methods taught by Unger in U.S. Pat. No. 6,632,671 and US20160058706 and elsewhere. Provided below are non-limiting embodiments of the nanoparticles and their preparation.

I. Reaction Binding of the Protein Component and the Polynucleotide Component.

The protein component is suspended in buffer (e.g. at about 1 to 70% w/w) and the polynucleotide component is added (e.g. by weight at 25-120% of protein component on a molar basis) in sufficient volume to maintain protein weight percent at or below 25% w/v for reaction. The polynucleotide and protein components are allowed to interact and complex by gentle mixing (e.g. about 3-8 minutes).

The protein component and the polynucleotide component of the biologic agent are selected by the skilled artisan according to biochemical, biophysical, genetic, and physiologic considerations. Typical polynucleotide lengths are 16 to 105 nt.

The protein component and polynucleotide component are generally incubated at about 10 to 120% polynucleotide to protein on a molar basis; e.g. at about 50%.

After complexation, the biologic agent is immediately added to the surfactant to create a reverse micelle.

II. Encapsulation.

An aqueous solution of protein component—polynucleotide complex is encapsulated by dispersing the biologic agent into a biocompatible, water-miscible solvent using a biocompatible, water-insoluble surfactant system suitable for preparation of an inverted or reverse micelle.

Suitable surfactant systems are well-known in the formulation arts as surface-active materials that are essentially hydrophobic and characterized by a hydrophile-lipophile balance (HLB) of less than about 6, a critical micelle concentration (CMC) of less than about 200 μM, or a critical packing diameter greater than 1. In one embodiment, the HLB value is between about 3 and 8, between about 3 and 6, and between about 4 and 6. In one embodiment, the hydrophobic is not biologically toxic as may be determined for example in cell culture testing. Suitable surface-active materials are non-ionic and thus not amphiphilic. In some embodiments, the HLB is less than about 5. Hydrophobic surfactants and hydrophobic, water-miscible solvents suitable for preparing reverse micelles are described in Pashley & Karaman (2004, In Applied Colloid and Surface Chemistry, John Wiley, pp. 60-85), Rosen (2004, in Surfactants and Interfacial Phenomena, John Wiley), The Handbook of Industrial Surfactants (1993, Ash, ed., Gower Pub), and Perry's Chemical Engineer's Handbook (1997, Perry & Green, 7th Ed., McGraw Hill Professional), incorporated herein by reference.

In some embodiments, the surfactant component may be 2,4,7,9-tetramethyl-5-decyn-4,7-diol(TM-diol), blends of 2,4,7,9-tetramethyl-5-decyn-4,7-diol(TM-diol), molecules having one or more acetylenic dial groups, cetyl alcohol, or any combination of any of these. In some embodiments, water-miscible solvents comprising food or USP grade oils, such as DMSO, DMF, castor oil, or any combination thereof, may be used. In one embodiment, a hydrophobic surfactant can be 2,4,7,9-tetramethyl-5-decyn-4,7-diol (TM-diol) or preparations thereof, such as Surfynol SE (Air Products), used in a concentration of up to about 15% by weight on protein, and a water-miscible solvent can be DMSO. The concentration of surfactant selected should be sufficient to prepare an optically clear nanoemulsion, but not so much as to induce aggregation, since aggregation may lead to overly large nanoparticles.

IV. Optional Ligand Coating.

The micelles can be coated with ligand by mixing one or more ligands with an aqueous buffer (e.g. about pH=7.4, 7-7.5) dilution of the composition (nanoparticles) of the previous step. In some embodiments, ligands can be mixed with nanoparticles in a ratio (by weight) of about 1:500 to about 1:0.1 of ligand to biologic agent, depending upon factors including the targeting moiety and the rate at which the nanoparticle is desired to dissolve or disassemble. In one embodiment, the weight ratio is about 1:80 (that is, about ⅟₈₀th) of ligand to biologic agent. In one embodiment, the weight ratio is about 1:40 of targeting moiety to biologic agent.

V. Stabilization.

Optionally, ligand-coated nanoparticles are further stabilized. To further stabilize the ligand-adsorbed nanoparticle, the aqueous suspension of nanoparticles coated with one or more ligands can be mixed into an aqueous solution of metal ions (i.e., a "stabilization solution or receiving bath") capable of precipitating, crystallizing, or iontophoretic exchange with the coated nanoparticles. Representative, non-limiting examples of solutes that can be used to form coated nanoparticles include ionic species derived from elements listed in the periodic table. Ions may be included in the aqueous stabilization composition in a range from about, for example, 0.1 part per trillion to about 1 M. An adequate amount of ion should be included, such that the coated nanoparticles are sufficiently contacted with ions, but not so much that aggregation occurs, which may lead to overly large nanoparticles.

In one embodiment, a stabilization (or crystallization or receiving) solution can comprise about 10 mM $Ca^{2+}$ and about 125 mM $Li^+$. If ultrapure reagents are used in the stabilization solution, very small amounts (e.g., less than about 1 mM) of ions such as Ba, Fe, Mg, Sr, and Bi may be added to optimize stabilization of the coated nanoparticles. In one embodiment, when the nanoparticles are prepared with sterile water, 126 mM of $Li^+$ is pre-treated with 2.5 ppb of $Cs^+$ for increased stability. In one embodiment, a stabilization solution includes 10.5 mM $Ca^{2+}$, 125 mM $Li^+$ (pre-mixed with 2.5 ppb $Cs^+$), 0.042 mM $Ba^{2+}$, 4 nM $Bi^{2+}$ with 7 nM $Mg^{2+}$, 0.88 nM $Sr^{2+}$, (all ultrapure, all prepared as stock solutions with sterile water, except $Sr^{2+}$, and $Mg^{2+}$ which are prepared with laboratory grade water, all metals are used as chloride salts, total bath volume approximately 36 ml). Flexibility of the system is demonstrated by for example nanoparticles showing high levels of cellular uptake that have been synthesized at lithium levels about 10-fold lower than those described here (data not shown). The artisan will understand that a variety of counter-ions can be used with these metals in the stabilization solution, such as chloride, sulfate, and nitrate.

In one embodiment, the stabilization solution comprises lithium pretreated with Cesium (Cs).

This stabilization is associated with changes in polymorphic form, as evidenced by substantive differences in melting point, thermal spectra and FTIR spectra.

VI. Storage.

The ligand-coated nanoparticle may be used immediately or dried and reconstituted in the future.

Nanoparticle Sizings

The instant nanoparticles have an average size of less than about 50 nm. Optionally, the $D_{90}$ (that is, the minimum size which is greater than the diameter of 90% of the particles) is about 50 nm, or optionally about 45 nm, or optional about 40 nm, or optionally about 35 nm, or optionally about 30 nm. In one embodiment, the instant nanoparticles are on average between about 2 and about 50 nanometers in diameter.

Ligands

Nanoparticles of the instant invention can optionally include a polymer shell comprising a ligand or targeting moiety for targeting the nanoparticles to a specific biological compartment, tissue, cell-type, or subcellular compartment.

In one embodiment, the instant nanoparticles provide a means for targeting the nanoparticles to a given tissue or cellular target, without the steps of chelating, conjugating, or covalently attaching the ligand or targeting moiety to the polymer coated nanoparticle or to the surfactant micelle.

In one embodiment the instant nanoparticles comprise a hydrophobic surface for adsorbing ligands including hydrophilic ligands in a manner that does not require complex chemistry development and is not limited by the ligand-size constraints associated with for example nanoparticles comprising ligands conjugated to or within said nanoparticles. Accordingly, one having skill in the art will understand that, with judicious selection of a targeting moiety based upon the intended target and methods and compositions known in the art, the inventive nanoparticles are capable of delivering bioactive agents to predetermined target tissue and cells.

Ligands, by way of non-limiting example, can be natural or synthetic nucleic acids, proteins, peptides, small molecules, etc., such as asialoglycoprotein, insulin, low density lipoprotein, growth factors, galactose, lectin, folate, and monoclonal and polyclonal antibodies directed against cell surface molecules etc.

The skilled artisan, with the teaching herein, will readily recognize such ligands in the literature, sometimes referred to as targeting factors, cell surface membrane receptor associated targeting factors, and other terms of art. For example, U.S. 20030138432 gives many examples of useful ligands in the art and describes methods of using such ligands as a targeting factor. U.S. Pat. No. 7,716,030 further teaches methods of designing targeting ligands.

By way of another example, tenfibgen can be a ligand of the instant invention and cause the nanoparticle to target tenascin receptors.

Other non-limiting examples include asialoorosomucoid (ASOR) and hyaluronan.

sgRNA-Cas Nanoparticle

In one embodiment of the instant invention, the protein component is a Cas protein and the polynucleotide component is sgRNA. With the instant invention, it is only now possible to modulate gene expression through the CRISPR technology in a manner with one or more of greater precision, efficacy, higher therapeutic levels, cellular targeting, subcellular targeting, modular and versatile structure, and shelf stability. sgRNA-Casa nanoparticles can further comprise template DNA. It is clear, according to the examples contained herein and according to insight by the mind of the inventor, that the technology is operable over a wide range of Cas proteins (and Cas-like proteins) and over a wide range of guide nucleic acids.

RISC Nanoparticles

In one embodiment of the instant invention, the protein component is any RISC protein such as an argonaute protein and the polynucleotide component is as guide RNA. With the instant invention, it is only now possible to modulate gene expression through the RISC technology (or RNAi technology) in a manner with one or more of greater precision, efficacy, higher therapeutic levels, cellular targeting, subcellular targeting, modular and versatile structure, and shelf stability. It is clear according to the examples contained herein and according to insight by the mind of the inventor, that the technology is operable over a wide range of of RISC proteins and RISC like proteins and for a wide range of guide nucleic acids.

Other Embodiments

It is specifically contemplated by the inventor that the instant technology is useful when the protein component is any protein component involving endonuclease activity that interacts biologically and physically with a polynucleotide in a complex and where the interaction is part of a biologic unit or cellular machinery. With the disclosure here, the skilled artisan is now able to encapsulate for example proteins and polynucleotides with diverse physicochemical properties.

In one embodiment, the protein component is an enzymatically active protein and the polynucleotide component is a substrate for the enzymatically active protein component.

In another embodiment, the protein component is an enzymatically active protein and the polynucleotide component is a substrate for the enzymatically active protein component and the two components are complexed in the nanoparticle by an enzyme-substrate interaction.

In another embodiment, the polynucleotide and protein components comprise PNA complexes and optionally further comprise donor DNA.

In one embodiment, the protein and polynucleotide components are not conjugated to each other.

In one embodiment, the instant nanoparticles comprise a surfactant wherein such surfactant is not amphiphilic.

In one embodiment, the instant nanoparticles do not require cholesterol for assembly; in other embodiments the instant nanoparticles do not contain cholesterol.

In some embodiments, the instant nanoparticles do not comprise polyethylene glycol (PEG) or derivatives thereof. In some embodiments, the instant nanoparticles do not comprise polyethylenimine (PEI) or derivatives thereof.

Uses of Instant Nanoparticles

Nanoparticles of the present invention are useful for gene editing in vitro, ex vivo, and in vivo. Instant nanoparticles are useful for gene editing in subjects, e.g. any plant or animal recipient of the administered nanoparticles. Other non-limiting examples are mammals such as humans, non-human primates, vertebrate animals, rodents, and the like. Non-limiting examples of ex vivo systems useful in combination with instant nanoparticles are those where experimentation is done in or on tissue from an organism in an external environment.

In some embodiments, the instant nanoparticles are useful for providing therapies for diverse genetic diseases.

Certain embodiments are useful for probing gene function in vivo (e.g. in animal models).

Certain embodiments are useful for identifying molecular targets in animal models of disease. The skilled artisan will readily envision other utilities.

Significantly, 80-90% of protein mutations responsible for human disease arise from the substitution, deletion, or insertion of single nucleotides. Sg-Cas nanoparticles, when further containing an appropriate donor template DNA, are useful for correcting such genetic defects.

Sg-Cas nanoparticles or RISC nanoparticles are useful to induce gene silencing at the transcriptional level. Sg-Cas nanoparticles are useful to induce gene silencing at the translational level. Accordingly, such nanoparticles of the instant invention are useful for preventing synthesis of defective gene products; e.g. to treat autosomal dominant diseases.

Sy-Cas nanoparticles according to the instant invention are useful to induce exon skipping to treat, for example, Duchene muscular dystrophy.

In certain embodiments, instant nanoparticles may be topically administered to intact, unbroken skin.

In other embodiments, nanoparticles may be topically administered without the use of physical methods and/or external enzymatic penetration enhancers and/or external chemical penetration enhancers, thus potentially reducing or avoiding cell damage, treatment pain, and other adverse reactions at the site of treatment.

In one embodiment, the invention provides methods of treating a subject having a disease of the liver. Such methods generally include the steps of administering a composition of liver-specific nanoparticles to a subject having a disease of the liver. It is a feature of one embodiment of the invention that the instant nanoparticles comprising a ligand shell can be targeted to and bind to liver cells and the binding of the nanoparticles to the liver cells results in the delivery of the pharmaceutical agent to the liver cells. Representative diseases of the liver include, without limitation, alpha-1-antitrypsin deficiency, Wilson's disease, familial hypercholesterolemia, ornithine transcarbamylase deficiency, phenylketonuria, peroxisome diseases, and familial amyloidosis.

In one embodiment, the invention provides for methods of mediating site-directed repair of a genomic mutation in liver cells of a subject.

In one embodiment, the compositions of the present invention may be administered by a number of routes, depending upon whether local or systemic treatment is desired and upon the area to be treated. In one embodiment, administration may be topical (including ophthalmic, vaginal, rectal, intranasal, transdermal), oral or parenteral. In one embodiment, topical treatment comprises treating a subject diagnosed with Pachyonychia Congenita disease. Parenteral administration includes intravenous administration, subcutaneous, intraperitoneal or intramuscular injection, intratumoral, or intrathecal or intraventricular administration. Without wishing to be bound by theory, the flexibility of particle (composition) administration options is enabled, in part, by the small size and low surface charge of the inventive and highly stable nanoparticle, allowing the particle and its drug cargo to traverse biologic barriers and size-limited structures such as the bloodstream wall, lymphatic channels, and the skin to reach cellular and molecular targets.

In one embodiment, the target is an in vitro biological system such as in vitro tissues or cells. In one embodiment, inventive non-ionic micelles and ligand-coated micelles are used for high-throughput testing of primary cells cultured 3-dimensionally.

In one embodiment, nanoparticles bearing protein combinations enable an ex vivo treatment of dendritic cells for subsequent readministration to a patient.

In one embodiment, nanoparticles bearing protein combinations enable an ex vivo treatment of dendritic cells for subsequent readministration to a patient for purposes of vaccination as part of a treatment protocol for solid and hemapoietic malignancies.

In one embodiment, instant nanoparticles are administered in to the airway epithelium. In one embodiment, the nanoparticles carry a bioactive agent useful for treating any one of the following genetic disorders affecting the lungs: Acropectorovertebral dysplasia F form, Acute interstitial pneumonia, Allergic bronchopulmonary aspergillosis, Alpha-1 antitrypsin deficiency, Alveolar capillary dysplasia, Arterial tortuosity syndrome, Asbestosis, Autoimmune pulmonary alveolar proteinosis, Beryllium disease, Blau syndrome, Brain-lung-thyroid syndrome, Bronchiolitis obliterans, Bronchiolitis obliterans organizing pneumonia, Bronchogenic cyst, Bronchopulmonary dysplasia, Cantu syndrome, Catamenial pneumothorax, Children's interstitial lung disease, Chronic granulomatous disease, Chronic thromboembolic pulmonary hypertension, Classical-like Ehlers-Danlos syndrome, Coal worker's pneumoconiosis, Congenital diaphragmatic hernia, Congenital lobar emphysema, Congenital pulmonary alveolar proteinosis, Congenital pulmonary lymphangiectasia, Congenital tracheomalacia, Cornelia de Lange syndrome, Costocoracoid ligament congenitally short, Cranioectodermal dysplasia, CREST syndrome, Cryptogenic organizing pneumonia, *Cutis laxa*, autosomal dominant, *Cutis laxa*, autosomal recessive type 1, Cystic fibrosis, Cystic medial necrosis of aorta, Diffuse cutaneous systemic scicrosis, Diffuse idiopathic pulmonary neuroendocrine cell hyperplasia, Diffuse panbronchiolitis, Donnai-Barrow syndrome, Eisenmenger syndrome, Ellis-Van Creveld syndrome, Emanuel syndrome, Enthesitis-related juvenile idiopathic arthritis, Eosinophilic granulomatosis with polyangiitis, Familial hypocalciuric hypercalcemia type 1, Familial hypocalciuric hypercalcemia type 2, Familial hypocalciuric hypercalcemia type 3, Familial mixed cryoglobulinemia, Familial thoracic aortic aneurysm and dissection, Familial thyroglossal duct cyst, Feingold syndrome, Fetal akinesia deformation sequence, Fibrosing mediastinitis, Froster-Huch syndrome, Game Friedman Paradice syndrome, Gaucher disease type 1, Gaucher disease type 2, Gaucher disease type 3, Geroderma osteodysplastica, Goodpasture syndrome, Granulomatosis with polyangiitis, Hashimoto-Pritzker syndrome, Hemangiomatosis, familial pulmonary capillary, Henoch-Schonlein purpura, Hereditary fibrosing poikiloderma with tendon contractures, myopathy, and pulmonary fibrosis, Hypercoagulability syndrome due to glycosylphosphatidylinositol deficiency, Idiopathic acute eosinophilic pneumonia, Idiopathic pulmonary fibrosis, Idiopathic pulmonary hemosiderosis, Intrahepatic cholestasis of pregnancy, Jeune syndrome, Juvenile dermatomyositis, Juvenile polymyositis, Kabuki syndrome, Kaolin pneumoconiosis, Kartagener syndrome, Laryngoonychocutaneous syndrome—See Epidermolysis bullosa, Lethal congenital contracture syndrome 1, Limited cutaneous systemic sclerosis, Limited systemic sclerosis, Loeys-Dietz syndrome, Loeys-Dietz syndrome type 1, Loeys-Dietz syndrome type 2, Loeys-Dietz syndrome type 3, Loeys-Dietz syndrome type 4, Lung agenesis, Lymphangioleiomyomatosis, Manouvrier syndrome, Meconium aspiration syndrome, Microphthalmia syndromic 9, Microscopic polyangiitis, Mixed connective tissue disease, Mounier-Kuhn syndrome, Multifocal fibrosclerosis, Multisystemic smooth muscle dysfunction syndrome, Niemann-Pick disease type B, Nocardiosis, Nontuberculous mycobacterial lung disease, Novak syndrome, Occipital horn syndrome, Orofaciodigital syndrome 4, PAGOD syndrome, Pallister-Killian mosaic syndrome, Pentalogy of Cantrell, Peroxisomal biogenesis disorders, Primary ciliary dyskinesia, Psoriatic juvenile idiopathic arthritis, Pulmonary alveolar microlithiasis, Pulmonary sequestration, Pulmonary venoocclusive disease, Recurrent respiratory papillomatosis, Respiratory distress syndrome, infant, Sarcoidosis—Not a rare disease, SCARF syndrome, Short rib-polydactyly syndrome type 3, Short rib-polydactyly syndrome type 1, Short rib-polydactyly syndrome type 2, Short rib-polydactyly syndrome type 4, Silicosis, Simpson-Golabi-Behmel syndrome, Sprengel deformity, Sudden infant death with dysgenesis of the testes syndrome, Systemic onset juvenile idiopathic arthritis, Thoracic dysplasia hydrocephalus syndrome, Thoracolaryngopelvic dysplasia, Thoracomelic dysplasia, Tracheal agenesis, Tracheobronchomalacia, Tracheobronchopathia osteoplastica, Vascular Ehlers-Danlos syndrome, Wilson-Mikity syndrome, Wolf-Hirschhorn syndrome, Wrinkly skin syndrome, Yellow nail syndrome, Young syndrome.

Unexpected Results

Through insight of the inventors, many of the challenges of gene therapy are now overcome by the delivering bio-machinery complexes (or portions of bio-machinery complexes) to cells and tissues of interest instead of merely delivering one or more bio-active components. This delivery of such machinery components has now been made possible by the inventors' technological breakthroughs which enable complexing of proteins with polynucleotides in a compact, stable, and non-toxic nanoparticle that optionally may be targeted to specific tissues and cells. Thus, the long-recognized need for effective gene-editing has now been met by the instant invention.

As demonstrated herein, or as observed in the mind of the inventor, the instant nanoparticles have one or more of the following surprising superior results:

a. When administered to a subject in need, they demonstrate superior efficacy when compared to nanoparticles lacking the protein component;
b. Demonstrate reduce immunogenicity;
c. Result in delivery to relevant subcellular locations;
d. Provide a means to supply functional machinery components to cell types that otherwise are deficient in them;
e. Provide higher therapeutic levels at the target tissues; and/or
f. Show increased stability in vivo and upon storage

VII. EXAMPLES

Example 1—Production of Nanoparticles and Comparators

Illustrative nanoparticles are generated as follows. These examples describe how some colloidal formulations of diverse cargos and biocompatible polymers may be generated, for subsequent in vivo and in vitro administration, Nanoparticles are prepared by the "dispersion atomization" method described in U.S. Pat. No. 6,632,671, which is incorporated herein by reference in its entirety, using modifications as described herein. The instant protein components are recombinantly prepared at PNA Bio (dCas9-NLS), Novaprotein (Cas9; E67) and Active Motif (Flag-Argonaute 2, 31886). Polynucleotide preparations are synthesized as described in Table 1.

TABLE 1

Polynucleotide component preparations

| Seq No. | Name | Description | Sequence (5'-3') | Manufacturer |
|---|---|---|---|---|
| 1 | RNAi F7 | Single-strand chimeric | 5'-gta aga ctt gag a 2o'ME [UGAUCC]-(propyl)-3' | Trilink |
| 1 | 2RF7 | Modified single-strand chimeric | 5'-g2o'ME[U]a aga ctt gag a 2o'ME[UGAUCC]-(propyl)-3' | Trilink |
| 2 | siF7 | Double-stranded siRNA | 5'☐GGAUCAUC UCAAGUCUUAC TT-3'(p) | Dharmacon |

TABLE 1-continued

Polynucleotide component preparations

| Seq No. | Name | Description | Sequence (5'-3') | Manufacturer |
|---|---|---|---|---|
| 3 | crF7 | Single guide (sg) RNA equaling 19 nt targeting sequenc (BOLD) + tracer RNA scaffolding sequence modified by the MS method of Porteus (2015 NBT). | AAGCACAUGGUGU CCUACACGUUUUA GAGCUAGAAAUAG CAAGUUAAAAUAA GGCUAGUCCGUUA UCAACUUGAAAAA GTGGCACCGAGU CGGUGCUUUU | Trilink Biotechnologies |

*p denotes passenger strand, sense strand or mRNA target region.
Lower case denotes phosphodiester DNA, upper case RNA.

Nanoparticles were made and designated as set forth in Table 2

TABLE 2

Nanoparticle Designations

| | ligand | Protein compnent | Polynucleotide component | other |
|---|---|---|---|---|
| Formula A | ASOR | rAgo2 | | |
| Formulas B | ASOR | rAgo2 | RNAiF7-50 | |
| Formula C | ASOR | rAgo2 | RNAiF7-100 | |
| Formula Da | ASOR | rAgo2 | 2RF7 - | |
| Formula E | ASOR | | RNAiF7 | |
| Formula F | ASOR | | siF7 | |
| Formula G | ASOR | | | sugar |
| Formula Ha | ASOR | Cas9 | crF7-short crystalization period | |
| Formula Hb | ASOR | Cas9 | crF7-extended crystalization | |
| Formula I | ASOR | dCas9 | crF7 | |

Briefly, to prepare each formula below, the following procedures were used:

Formula A, (ASOR rAgo2, MW 106 kDa). About 31.25 μg of Flag-Ago2 (from insect cells) is resuspended into about 100 μl of reaction buffer (prepared using sterile water as about 20 mM Hepes, about ph 7.4, about 5% ethylene glycol, about 1 mM DTT) following washing with reaction buffer through about a 30 kDa MWCO filter (Vivaspin 6, Sartorius). This protein component is then dispersed using a water-insoluble surfactant system (2,4,7,9-tetramethyl-5-decyn-4,7-diol (TM-diol; SE-30 (Air Products), about 1 μg in about 50% DMSO. Following emulsification with a water-miscible solvent (DMSO), by adding about 150 μl of DMSO, vortexing, and subsequently placing in bath sonicator for about 15 minutes, the micelles are then inverted and diluted by the addition of about 700 μl of PBS, also prepared in sterile water.

The resultant hydrophobic micelles are coated (non-covalently) by the addition of about 0.4 μg of Asialoorosomucoid (Athens Research), placed in a bath sonicator for about 30 minutes, is transferred to a 5 ml polypropylene tube, and is diluted up to about 3 ml with PBS, prepared with sterile water, then is atomized with a manual actuator using an approximately 250 μm diameter orifice with feed pressure of less than about 10 psi into a salt receiving solution of sterile water containing primarily $Li^+$ (about 31.4 mg $Li^+$ (pre-mixed with about 2.5 ppb $Cs^+$ on $Li^+$), about 15.0 mg $Ca^{2+}$, about 210 μg $Ba^{2+}$, about 29 μg $Bi^{2+}$ with about 6.12 ng $Mg^{2+}$, about 2.76 ng $Sr^{2+}$, (all ultrapure, all are prepared as stock solutions with sterile water except $Sr^{2+}$ and $Mg^{2+}$ are prepared with laboratory grade water, all metals are used as chloride salts, total bath volume approximately 32 ml). The total reaction volume is approximately 36 ml. The level of the following metals tested for in the sterile water used to prepare the stabilization solution is determined to be less than about 0.2 parts per million in sum total: aluminum, arsenic, barium, cadmium, chromium, copper, iron, lead, manganese, nickel, rubidium, sulfur, vanadium, and zinc.

The premixing step comprises adding $Cs^+$ at about 0.1 μg/1 ml to about 4M $Li^+$, at about 2.5 ppm $Cs^+$ to $Li^+$ by weight, in sterile water in a 50 ml tube, and rotating for about 2 minutes. Following cold-room incubation (at about 4° C.) on a roller mill at about 0.5 rpm in 40 ml round-bottomed tubes for about 4 hours, which further stabilizes the coated micelles in the salt solution, the sub-50 nm nanoparticles are recovered by centrifugation at about 20,000×g at about 4° C. for about 1 hrs and are resuspended in about 10 mM Hepes+10% lactitol, about pH=7.4, (at a concentration of about 0.125 μg/μl), transferred to a 2 ml conical, and spun down at maximum speed for about 5 minutes at about 4° C., and is washed by resuspending pellet in about Hepes/10% lactitol, and is sterilized through a 0.2 μm filter, and frozen at about −20° C.

In all formulations described in the instant example, a small amount (about 1% of coating weight) of Syrian Hamster IgG is added in tracer amounts into the ligand coat to enable immunodetection of nanoparticle uptake by anti-Syrian Hamster antibodies. Average particle size is less than about 50 nm, as measured Dynamic Light Scattering (DLS) on a Nicomp ZLS 380 instrument. Particle size is measured as about 2±0.4 nm, a count rate of about 84 KHz with population volume of about 99.8% along with a surface charge of about 5.6+/−0.5 mV per manufacturer's instruction.

Formula B, (ASOR rAgo2 RNAiF7-50), Approximately 50% of the Ago2 is co-encapsulated with the polynucleotide component as in Formula A and as follows. About 31.25 μg of Flag-Ago2 (from insect cells) is resuspended into about 100 μl of reaction buffer (prepared using sterile water as about 20 mM Hepes, at about ph 7.4, about 5% ethylene glycol, about 1 mM DTT) following washing with reaction buffer through an about 30 kD MWCOa filter (Vivaspin 6, Sartorius). The protein component (Ago2) in an amount of about 295 pmol is then reacted with an amount of polynucleotide (guide RNA, i.e. RNAi F7, Sequence 1 from Table 1) by slow trituration about every two minutes over about a six minute period. This is generally sufficient to drive the complexation such that about or greater than 50% of the protein is complexed. RNAi F7 is chimeric guide strand (single-stranded) from siFVII, (Akinc, et. al, 2009 Mol Ther 17(5)872-879) and listed as Sequence 1. Backbone chemistry is described in its entirety in U.S. Pat. No. 9,132,148, incorporated herein in its entirety.

Polynucleotide-protein complex is then dispersed using a water-insoluble surfactant system (2,4,7,9-tetramethyl-5-decyn-4,7-diol (TM-diol; Surfynol SE (Air Products), about 1 μg in about 50% DMSO. Following emulsification with a water-miscible solvent (DMSO), by adding about 150 μl of DMSO, vortexing, and subsequently placing in bath sonicator for about 15 minutes, the micelles are then inverted and diluted by the addition of about 700 μl of PBS.

The resultant hydrophobic micelles are coated (non-covalently) by the addition of about 0.4 μg of Asialoorosomucoid (Athens Research), are placed in a bath sonicator for about 30 minutes, are transferred to a 5 ml polypropylene tube, and are diluted up to about 3 ml with PBS, then they are atomized with a manual actuator using an approximately 250 µm diameter orifice with feed pressure of less than about 10 psi into a salt receiving solution of sterile water containing primarily Li$^+$ (about 31.4 mg Li$^+$ (premixed with about 2.5 ppb Cs$^+$ on Li$^+$), about 15.0 mg Ca$^{2+}$, about 210 µg Ba$^{2+}$, about 29 µg Bi$^{2+}$ with about 6.12 ng $Mg^{2+}$, about 2.76 ng $Sr^{2+}$, (all ultrapure, all are prepared as stock solutions with sterile water except $Sr^{2+}$ and $Mg^{2+}$ prepared with laboratory grade water, all metals are used as chloride salts, total bath volume approximately 32 ml). The total reaction volume is approximately 36 ml.

Following cold-room incubation at about (4° C.) on a roller mill at about 0.5 rpm in 40 ml round-bottomed tubes for about 4 hours, which further stabilizes the coated micelles in the salt solution, the approximately sub-50 nm nanoparticles are recovered by centrifugation at about 20,000×g at 4° C. for about 1 hrs and are resuspended in about 10 mM Hepes+10% lactitol, at about pH=7.4, (at a concentration of about 0.125 μg/μl), is transferred to a 2 ml conical, and spun down at maximum speed for about 5 minutes at about 4° C., are washed by resuspending pellet in about Hepes/10% lactitol, sterilized through an about 0.2 μm filter, and frozen at about −20° C.

Average particle size for Formula B is less than about 50 nm as measured by DLS. Particle size is measured as about 11±2 nm, a count rate of about 24 KHz with population volume of about 99.6% along with a surface charge of about 3±0.6 meV per manufacturer's instruction.

Formula C, (ASOR rAgo2 RNAiF7-100) is formulated similarly to Formula B except that the Ago 2 protein is reacted with the polynucleotide comprising chimeric single-stranded poly RNAi F7 in an amount calculated to achieve about 110% of completion of the reaction in that about 325 pmol of the polynucleotide was reacted with about 295 pmol of Ago2 to initiate a core to support formation of a micelle. For characterization, average particle size for Formula C is less than about 50 nm, as measured by DLS. Particle size is measured as about 19±2 nm, a count rate of about 26 kHz with population volume of about 98.6% along with a surface charge of about 2.9+/−0.1 mV per manufacturer's instruction.

Formula D, (ASOR rAgo2 2RF7) is formulated similarly to Formula C with the change that the polynucleotide (guide strand) has a different backbone chemistry (2RF7, Sequence 1). 2RF7 is distinguished from RNAi F7 by modifying the typical nucleotide in position 2 from the 5' end to a 2'-O-Methyl Ribonucleotide. For characterization, average particle size for Formula C is less than about 50 nm, as measured by DLS. Particle size is measured as about 14±2 with population volume of about 99.5% along with a surface charge of about 0.3+/−1 mV per manufacturer's instruction.

Formula E, (ASOR RNAiF7 6115 Da MW). About 250 μg of about 20 mer, chimeric, single-stranded guide strand RNAiF7 (Table 1) is formulated generally as in Formula A, by first complexing the polynucleotide component with about 62.5 μg of about 11,800 Da MW polyornithine (Sigma), then dispersing using a water-insoluble surfactant system (2,4,7,9-tetramethyl-5-decyn-4,7-diol (TM-diol; SE-30 (Air Products), at about 7.5 μg in about 50% DMSO. Following emulsification with a water-miscible solvent (DMSO), by adding about 150 μl of DMSO, vortexing, and subsequently placing in bath sonicator for about 15 minutes, the resultant micelles are then inverted and diluted by adding about 700 μl of PBS, also prepared in sterile water. Following the addition of about 3.125 μg of ASOR to coat micelles as described in Formula A, the resultant hydrophobic micelles are then processed as generally described in Formula A with the following changes in receiving bath component weights: about 2.42 ng $Mg^{2+}$, about 10.92 ng $Sr^{2+}$. For characterization, average particle size for Formula E is less than about 50 nm, as measured by DLS. Particle size is measured per manufacturer's instruction at about 10±1 nm with population volume of about 99.2% along with a surface charge of about 0.2+/−0.4 mV.

Formula F, (ASOR siF7, 13,800 Da MW nominal) about 250 μg of about 21 mer, unmodified, double-stranded RNA polynucleotide (siFVII, Akinc, et. al, 2009 *Mol Ther* 17(5) 872-879), is first complexed with about 54 μg Beta-cyclodextrin (Sigma), then is dispersed into about 100 μl of sterile water using a water-insoluble surfactant system (2,4,7,9-tetramethyl-5-decyn-4,7-diol (TM-diol; SE-30 (Air Products)), about 7.5 μg in about 50% DMSO.

Following the addition of about 3.125 μg of ASOR to coat micelles as described in Formula A, the resultant hydrophobic micelles are then processed as generally described in Formula A with the following changes in receiving bath component weights: about 10.72 ng $Mg^{2+}$, about 212.5 ng $Sr^{2+}$. For characterization, average particle size for Formula E is less than about 50 nm, as measured by DLS. Particle size is measured per manufacturer's instruction at about 11±2 nm with population volume of about 99.4% along with a surface charge of about 0.2±0.7 meV.

Formula G, (ASOR sugar), about 500 μg of erythritol (MW 122.12) is dispersed into about 100 μl of sterile water using a water-insoluble surfactant system (2,4,7,9-tetramethyl-5-decyn-4,7-diol (TM-diol; SE (Air Products)), about 8.75 μg in about 50% DMSO.

Following the addition of about 6.25 μg of ASOR to coat micelles as described in Formula A, the resultant hydrophobic micelles are then processed as generally described in Formula A with the following changes in receiving bath component weights: about 5.75 ng $Mg^{2+}$, about 10.36 ng $Sr^{2+}$, For characterization, average particle size for Formula E is less than about 50 nm, as measured by DLS. Particle size is measured per manufacturer's instruction at about 13.3±1.9 nm with population volume of about 99% along with a surface charge of about 0.04±0.75 meV.

Formula Ha, (ASOR Cas9 F7-short). The polynucleotide component used here is the recombinant Cas9 endonuclease (Novoprotein E365, pl 9.1, 163 kDa MW) and is reacted with, as the polynucleotide, guide RNA (F7-short). This creates a species with an overall negative charge. The equimolar amount of the about 105 nt guide RNA carries approximately 3.25 nmol (−) charge per μg from phosphate groups, while the protein component carries about a +22 charge per molecule as reported from sequence and supported by it high isoelectric point. Thus, for the about 31.25 μg reaction, an imbalance of negative charge is operable following protein-substrate binding, e.g. about 4290 pmol of (+) charge from about 195 pmol of Cas9 is not balanced by ~22680 of phosphate charge from about 216 pmol of sgRNA.

We compare the impact of charge neutralization as is commonly practiced in art for nucleic acid cargos (See Formulas E, F). Surprisingly, added charge neutralization during the micelle formation step (about 26%, Spermine), (about 55.5%, Spermidine) does not promote capsule formation. Instead, best results are obtained with no externally-mediated charge neutralization in the manner of a sugar cargo which is electrically neutral (See Formula G). This unexpected course of events indicates that a substantially different mechanism is in effect in the synthesis of nanoparticles containing substrate-reacted enzymatic proteins.

In Formula Ha, recombinant Cas9 is coencapsulated with the polynucleotide component at about 110% molar completion of the reaction in a sequence similar to Formula A as follows. About 31.25 μg of recombinant Cas9 (from *E. Coli*) is resuspended into about 100 μl of reaction buffer (prepared using sterile water as about 20 mM Hepes, at about ph 7.4, about 5% ethylene glycol, about 1 mM DTT). The protein component Cas9 (~195 pmol) is then reacted with an amount of guide RNA (crF7, Table 1) sufficient to drive about 110% completion (~216 pmol) of the reaction by slow trituration every two minutes over a six minute period. The polynucleotide component is crF7 guide RNA (single-stranded, about MW 33,528) listed as Sequence 3 in Table 1.

The protein-polynucleotide complex is then dispersed using a water-insoluble surfactant system (2,4,7,9-tetramethyl-5-decyn-4,7-diol (TM-diol; SE (Air Products), about 1 μg in about 50% DMSO. Following emulsification with a water-miscible solvent (DMSO), by adding about 150 μl of DMSO, vortexing, and subsequently placing in bath sonicator for 15 minutes, the micelles are then inverted and diluted by the addition of about 700 μl of PBS.

Figure 1:
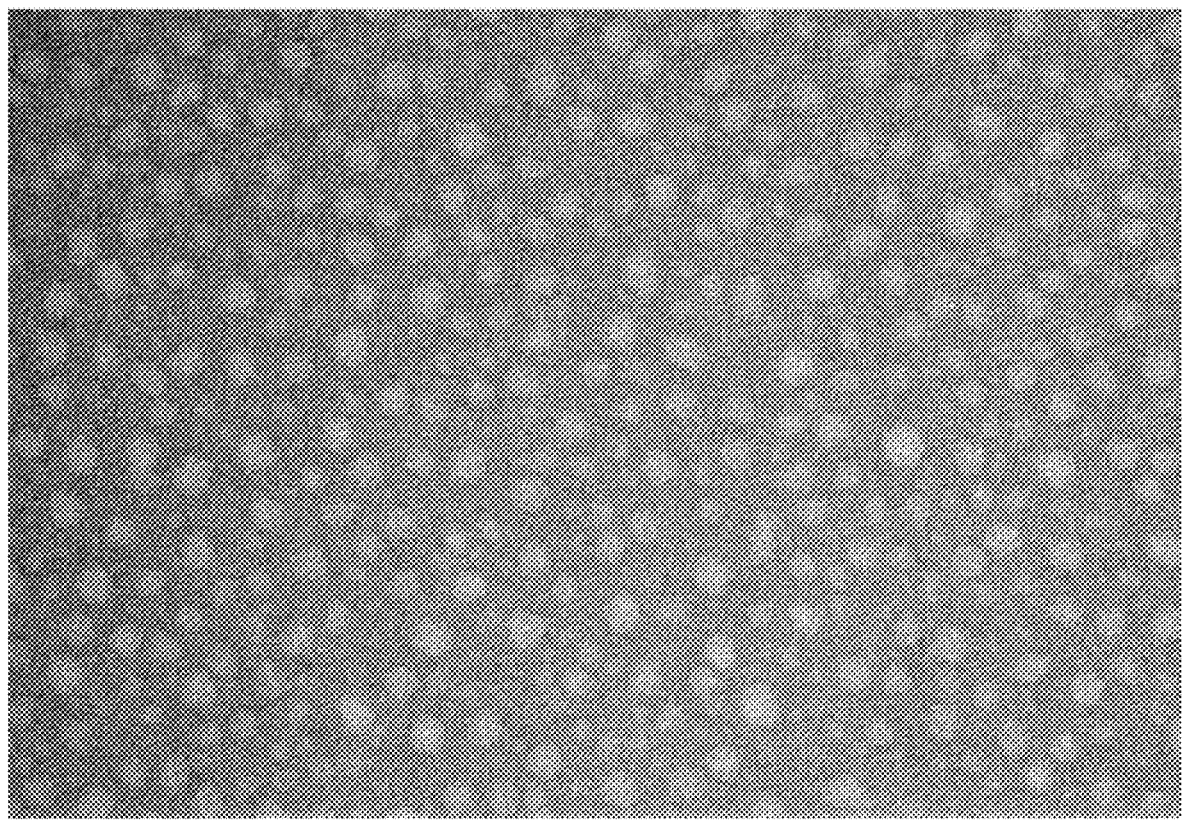
FIG. 1 is a TEM micrograph for Formula IIa.

Following the addition of about 0.4 μg of ASOR to coat micelles as described in Formula A, the resultant hydrophobic micelles are then processed as generally described in Formula A except that the receiving bath component weights are about 5.75 ng $Mg^{2+}$ and about 2.6 ng $Sr^{2+}$. For characterization, average particle size for Formula E is less than about 50 nm, as measured by DLS. Particle size is measured per manufacturer's instruction at about 23.4±4.3 nm with population volume of about 91.2% along with a surface charge of about 0.03±0.78 mV. TEM for Formula Ha is illustrated in FIG. 1 and shows a fractal crystalline morphology with a visible protein ligand corona.

Formula Hb, A more stable crystalline variant of Formula Ha is synthesized by incubating ASOR ligand-coated micelles in the receiving bath for about 36 hours rather than about 4 hours. The receiving bath component weights are about 5.23 ng $Mg^{2+}$, about 2.36 ng $Sr^{2+}$ and without bismuth. In this case, the receiving bath volume is about 40.5 and the total reaction volume is about 44.4 ml. For characterization, average particle size for Formula E is less than about 50 nm, as measured DLS. Particle size is measured per manufacturer's instruction at about 19±3.2 nm with population volume of about 97.1% along with a surface charge of about 0.07±0.73 meV.

Formula Hc is formulated similarly to Formula Ha with the change that about 31.25 ug of a non-canonical TypeII-B Cas9, without a bi-lobe nuclease structure, e.g., from *F. Novicida* is substituted in as the enzymatic protein pre-reacted with it RNA binding partners. Average particle size for Formula Hc is less than about 50 nm, as measured Dynamic Light Scattering (DLS) on a Nicomp ZLS 380 instrument. Zeta potential is measured, based on manufacturer's instructions, and determined to approximately neutral.

Formula Hd is formulated similarly to Formula Hc with the change that non-canonical Type V Cpf1 is substituted for non-canonical Type II-B Cas9.

Formula I, (ASOR dCas9 F7), Formula I is formulated similarly to Formula Ha with the change that the protein component is double mutant recombinant spCas9 with about 6x his tag and NLS from SV40 N-terminus ((D10A/H840A, PNA Bio #CD03) at about 31. about 25 μg. Average particle size for Formula I is less than V50 nm, as measured by DLS. Particle size is measured as about 2K 14+/−2 nm with population volume of about 98.9% along with a surface charge of about 0.6+/−0.8 mV per manufacturer's instruction.

Formula J (Tenfibgen Chymotrypsin-Trypsin). Formula J is formulated similarly to Formula A with the change that about 31.25 μg of trypsin-chymotrypsin mixture (in the activity ratio 6:1) having enzymatic activity of about 2000 AU/mg was substituted for the enzyme-substrate combination and tenfibgen (MW 26,500 Da, the fibrinogen fragment of Tenascin-C, fully incorporated from U.S. Ser. No. 14/844, 828) is substituted for ASOR. Following the addition of about 0.4 μg of Tenfibgen to coat micelles as described in Formula A, the resultant hydrophobic micelles are then processed as generally described in Formula A with the following changes in receiving bath concentrations: about 6.38 ng $Mg^{2+}$, about 28.75 ng $Sr^{2+}$. Particles are incubated with rolling as described in Formula A with the change of about 48 hours of incubation time before centrifugation and purification. In separate batch runs, non-ionic micelles without ligand coating and ligand-coated micelles without crystallization are also produced. Average particle size for Formula J is less than about 50 nm, as measured Dynamic Light Scattering (DLS) on a Nicomp ZLS 380 instrument. Zeta potential is measured as approximately neutral per manufacturer's instruction.

Formula K (Tenfibgen Erythritol), about 500 μg of erythritol (MW 122.12) is dispersed into about 100 μl of sterile water using a water-insoluble surfactant system (2,4,7,9-tetramethyl-5-decyn-4,7-diol (TM-diol; SE (Air Products), about 8.75 μg in about 50% DMSO. Following the addition of about 6.25 ug of Tenfibgen to coat micelles as described in Formula J, the resultant hydrophobic micelles are then processed as generally described in Formula A with the following changes in receiving bath concentrations: about 6.38 ng $Mg2^+$, about 28.75 ng $Sr2^+$. Particles are incubated with rolling as described in Formula A with the change of about 48 hours of incubation time before centrifugation and purification. For characterization, average particle size for Formula E is less than about 50 nm, as measured Dynamic Light Scattering (DLS) on a Nicomp ZLS 380 instrument.

Thus, we have described in some embodiments compositions and methods for formulation of nanoparticles to deliver protein-polynucleotide complexes where the nanoparticles may be nonionic, ligand-coated or crystalline ligand-coated. The species demonstrate similar desirable properties across a range of diverse cargos and chemistries.

Example 2—Demonstration that Polynucleotide—Protein Complex Encapsulation into Nanoparticles Enhances Incorporation into Crystalline Nanoparticles To date, intracellular enzymes have not been used effectively for in vivo therapy by systemic in vivo delivery. Such use is constrained by enzyme chemical and mechanical fragility through the process of formulation, exposure to denaturing excipients, and exposure during administration to denaturing proteinases in the bloodstream, tissues and intracellularly. It has been discovered, quite unexpectedly, that the instant polynucleotide components may be used to facilitate incorporation of an enzyme into a nanoparticles to create a supramolecular crystalline complex.

Moreover, efforts at systemic delivery of nucleoprotein complexes as the biologic agents taught here as pre-formed entities have not been successful until the development of the instant invention.

In this example, the protein components was Ago2, a 104 kDa endonuclease was coupled with the polynucleotide component of a short, approximately 22 mer, RNA "guide strand" (in this example, a chimeric guide strand) against murine Coagulation Factor VII to provide specificity for specific cleavage of the target mRNA, to inhibit production of the target Factor VII.

Encapsulation of the Ago2—guide strand complex (at about 50% molar loading) is compared with 1) protein component alone (Formula A), 2) anti-Factor VII guide strand—Ago complex with about 50% molar complexation (Formula B), 3) anti-Factor VII guide strand with Ago2 complex with about 110% molar complexation (Formula C) and 4) anti-Factor VII guide strand—Ago2 complex with about 110% molar complexation using an alternate backbone chemistry for the polynucleotide chimeric guide strand.

Following formulation, nanoparticles are characterized by DLS and zeta potential. Supernatants from the lithium crystallization solution (mother liquor) were buffer-exchanged using an about 5 kDa MWCO ultrafilter (Vivaspin 20, Sartorius). Equal volumes are normalized to the control (Ago2 and excipients without crystallization but filtered) from each of the approximately 100 µl retentates are electrophoresed on an about 4-12% gradient bis-tris gel (Invitrogen) using a Tris-glycine buffer and detected for protein by silver staining (Pierce).

The results, summarized in Table 3, show a direct correspondence between polynucleotide component and protein component complexation and incorporation into the crystalline supramolecular nanoparticle complex as less protein was measured in the reaction supernatant with increased completion of the specific binding reaction. For the protein component alone, subjected to nanoencapsulation, a protein band running at the same approximate 100 kDa level as control Ago2 and Ago2 admixed in excipients without further processing is visibly indicating no incorporation into particles that would be in the pellet. Dynamic light scattering (DLS) before any nanoencapsulation, Ago2 protein showed a particle size distribution of about 6±1 nm (about 95%); about 35±6 nm (about 4.6% population volume).

Following the nanoencapsulation process, in the product stream at equivalent volumes, only about a 2 nm species with a high primary incidence (about 98.5% population volume) was measured by DLS along with a high count rate (about 84 KHz) suggesting a degradation for the naked about 6 nm Ago2 protein species. Lower count rates and species larger than about 6 nm appeared as unimodal peaks in reacted Ago2 capsules (Table 3). Between about 50% and 100% of full binding reaction, the residual Ago2 band in the supernatant disappeared indicating a direct correspondence between extent of reaction and feasibility for successful incorporation into inventive nanopartices. We conclude interactions between the protein component and polynucleotide component in the complex provides a means for greatly enhancing incorporation into crystalline nanoparticle supramolecular complexes.

TABLE 3

Incorporation results for polynucleotide complexation into nanoparticle

| Formula, Cargo | Protein Band in supernatant densitometry (1, FIG. 2) | Particle Size by DLS (nm); Population volume (%) | Count rate from equivalent volumes |
|---|---|---|---|
| Ago 2 standard (0.6 ug) | 70.6 | | |
| Ago 2 + excipients, no processing | 39.2 | | |
| Formula A, Ago 2 protein | 19.6 | 2 ± 0.4 (99.8%) | 84 kHZ |
| Form. B, RISC - 50% reacted | 6.0 | 11 ± 2 (99.6%) | 24 kHZ |
| Form. C, RISC - 100% reacted | 2.41 | 19 ± 2 (98.6%) | 26 kHZ |
| Form D, RISC 2RF7 - 100% | 0.31 | 14 ± 2 (99.5%) | 18 kHZ |

Ago2 standard on gel is about 0.6 µg, Supernatant concentrates represented approximately 25% of the total reaction supernatant. Densitometry is performed in NIH Image J using mean values of equivalent areas subtracted from nearby background.

Example 3—Protein Co-Encapsulation of Protein Component with Polynucleotide Component Enriches Cells with Active RISC for Enhanced Target Gene Modulation Superior efficacy of the instant nanoparticles (Risc RNAi F7; Formula B) is demonstrated in comparison to guide strand alone (Formula E) nanoparticles in 3D cultured FL83B hepatocytes (ATCC).

3D hepatocyte cell cultures are prepared by plating about 25,000 murine FL83B murine hepatocyte cells on to ECM-coated spun polymer scaffolds (Corning, UltraMax) in chamber slides. Formula B and Formula E nanoparticles are added at various concentrations to the cultures and harvested for microscopy after about 3 days.

Dose response for Factor VII protein inhibition are assayed by confocal fluorescence microscopy for Factor VII immunosignal (GeneTex) and qPCR.

Formula B administration demonstrates full inhibition of Factor VII protein at about 1 pmol (about 4 nM) continuing through about 2.0 nM with recovery beginning around about 0.32 nM demonstrating about a 3 log response range. In contrast, Formula E bearing the guide strand only shows full inhibition by microscopy at about 5 nmol (about 20 µM) recovering by about 1.25 nmol (about 5 µM) for about a 0.4 log response range and approximate increase in activity of about 3.5 logs (about 2 nM vs. about 12.5 µM) for encapsulated RISC complex vs encapsulated guide RNA alone. Results are illustrated in FIG. 3.

Example 4—In Vivo Demonstration of Superior Results of Instant RISC Nanoparticles Systemic in vivo delivery is demonstrated in C57BL/6NCrSim mice in about a 3 day acute study. Mice are administered equal particle number doses (about 10e13) of 1) ASOR RISC RNAiF7 (Formula B), ASOR RNAiF7 (Formula E), ASOR siF7 (Formula F); control animals treated with about standard 200 µl of about 1 mg/ml ASOR erythritol (Formula G). For G1, Formula B, additional regimens using about 10e12 particle (about 136 µg/kg) doses are tested.

For RISC nanoparticles, about 10e13 particles are approximately equal to about 250 pmol or about 1.36 mg/kg of protein complex while this particle dose is approximately equal to about 1 nmol or about 0.75 mg/kg of polynucleotide component. Particle numbers are estimated assuming closest theoretical packing into final particle size measured by DLS.

At study termination, citrated plasma is collected for Factor VII ELISA by terminal cardiac puncture. By visual observation during necropsy, blood from RISC nanoparticle-treated animals is bright red and of very low viscosity, while blood from control animals is dark with a purple hue and of much higher viscosity in the collection syringe. Blood from animals treated with nanoparticles made to contain F7 RNA or siRNA without Ago2 appear to be of an intermediate nature. A Factor VII ELISA of citrated plasma samples shows that only nanoencapsulated RISC has a significant (about 83%) reduction in Factor VII plasma protein at Day3. Lower doses of nanoencapsulated RISC or oligo or siRNA show no change or in some cases elevations suggesting that biological modulation is occurring.

We conclude that the instant RISC nanoparticle demonstrates superior effective systemic delivery and efficacy and retention of enzymatic activity. Supramolecular crystalline RISC shows significant improvement in inhibition of phenotypic activity and transcript levels confirming in vitro results observed in 3D cell culture.

Example—5 Superior Efficacy of Instant CRISPR Complex Nanoparticles Demonstrated In Vivo We assay for functional in vivo activity of the CRISPR complex nanoparticles i.e. bacterial endonuclease Cas9 reacted with about a 105 nt anti-Factor VII guide RNA (sgRNA, described as Formula H in Example 1) in Balb/C immunocompetent mice. In this study, we compare two formulas, a shorter dissolution capsule (which is prepared using a shorter crystallization period amenable to in vitro studies, Formula IIa) and a longer dissolution capsule (generally used for longer in vivo circulation, Formula IIb).

Three dosing levels are examined with a two dose regimen; 1) about 3e12 particles at about 1.6 mg/kg; 2) about 3e11 particles at about 160 µg/kg q3D; and 3) about 3e10 particles at about 16 µg/kg q3D of RISC nanoparticles. Particle numbers are estimated assuming closest theoretical packing into final particle size measured by DLS. A fractional factorial design is used with groups of three assigned to each dissolution profile design, and mice are sacrificed to collect livers for microscopy, western blotting, qPCR and mutational analysis at about 7 days post initiation of treatment.

Figure 4:
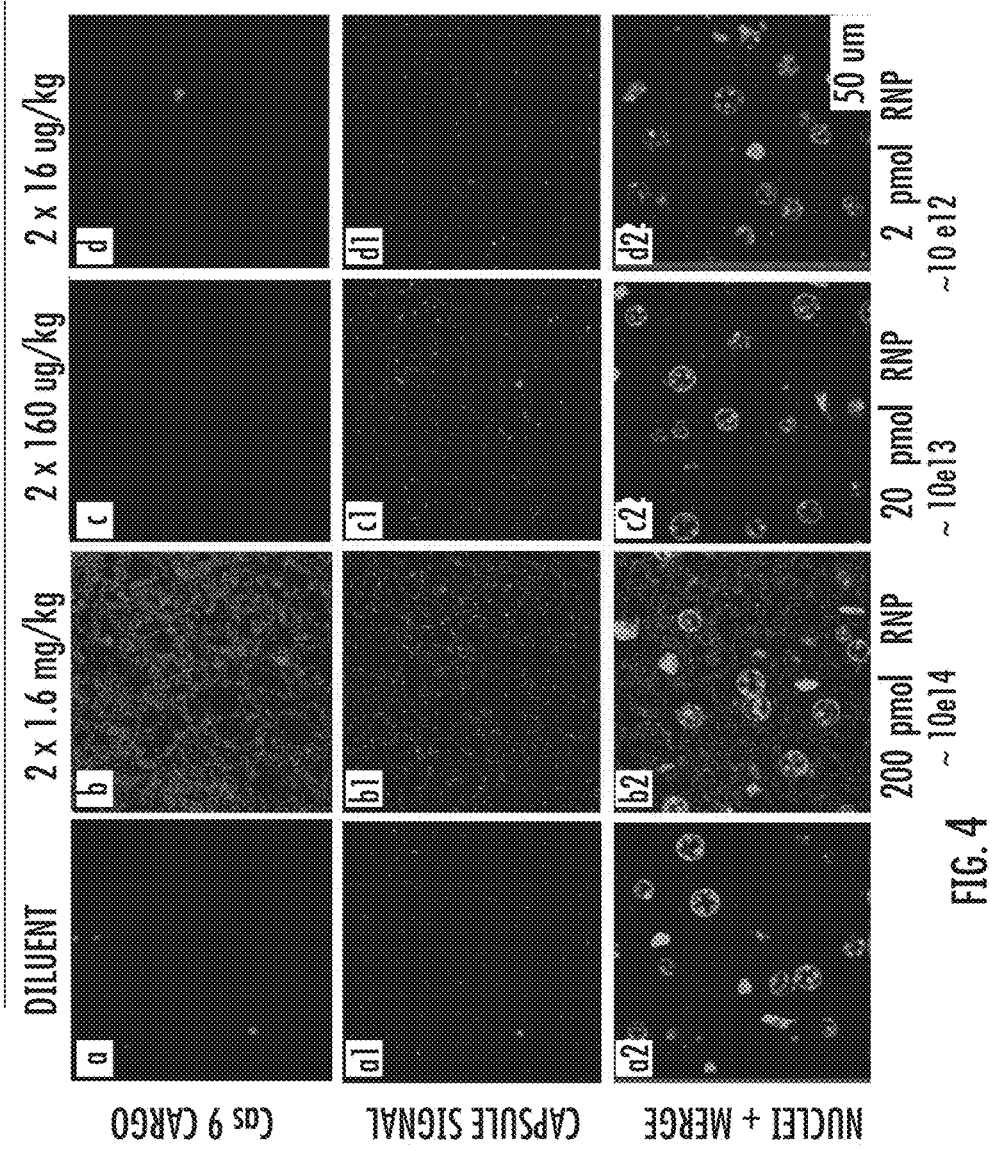
FIG. 4 shows immunohistochemistry of mouse liver.

We investigate changes in Factor VII and Cas9 protein component immunosignal by confocal immunofluorescence microscopy for the groups over the dose range. Cas9 immunosignal is used for capsule localization and trafficking while Factor VII protein immunosignal demonstrated the phenotypic effect of Factor VII mutation and/or CRISPR-based silencing. Results are illustrated in FIG. 4.

We find that Cas9 immunosignal (the nanoparticle cargo) shows a punctate cytoskeletal pattern at mg/kg dose levels (highest dose, about 3e12 particles) in individual hepatocytes that decreases with dose level to not detectable at about 16 µg/kg (lowest dose level, 3e10 particles).

At the same time, Factor VII immunosignal is maximally decreased as detectable Cas9 signal disappears suggesting a sequence of events where capsule processing to "release" Cas9 for action is hindered in the case of potentially too many capsules entering the cell. This means that the highest dose tested is not the optimal biological dose (OPD). This pattern of persistent Cas9 immunosignal indicating saturation corresponding with poorer Factor VII inhibition is confirmed in 3D hepatocyte cell culture.

For Factor VII immunosignal, we observe reduction in signal in 3D mouse hepatocytes that appears maximal at about 1 pmol (about 4 nM) and is nearly recovered by about 0.1 pmol (about 0.4 nM). At the highest dose level of about 5 nmol, no reduction in Factor VII is observed consistent with the existence of an optimal biological dose.

We additionally perform western blotting of liver lysates from mice under denaturing conditions confirming our observations by microscopy. Under denaturing conditions, Factor VII separates into three fragments of about 73, 50 and 43 kDa. Densitometry of Factor VII bands (Genetex) normalized to Lactate dehydrogenase (Cell Signaling) levels indicated about 40-85% knockdown of the three fragments at the peak effective middle dose of about 2×3e12 q3D particles or about 2×160 µg/kg. Results are summarized below in Table 4.

TABLE 4

Densitometry for Factor VII western blotting of 7 day liver lysates

| Treatment | 70 kDa fragment | Δ % | 50 kDa fragment | Δ % | 43 kDa fragment | Δ % |
|---|---|---|---|---|---|---|
| PBS | 35 ± 3 | | 5 ± 0.6 | | 26.3 ± 2.2 | |
| 2 × 1.6 mg/kg | 29 ± 2 | −17.3 | 2.5 ± 0.12 | −49.4* | 18.4 ± 1.3 | −29.8* |
| 2 × 160 µg/kg | 20 ± 3.7 | −42.24* | 0.72 ± 0.23 | −85.5* | 11.63 ± 2 | −55.7* |
| 2 × 16 µg/kg | 20.8 ± 6.4 | −40.4 | 2.8 ± 0.25 | −44.7* | 16 ± 7.7 | −39.2 |

Notes:
*= $p < 0.5$

With respect to mutation, amplicon sequencing using an Illumina Miseq approach detects no double strand breaks as having occurred at the target site indicating no cutting activity of the Cas9 enzyme. We examine mRNA levels for the best responding group (middle dose) using primers that either bind upstream of the Exon 2 binding site (Exon 1) or downstream of the Exon 2 binding site (Exon 4). qPCR executed using Exon 1 primer indicates no change in Factor VII transcript had occurred while qPCR executed using the downstream Exon 4 primer indicates an approximately 39% decrease in transcript measured as (Δcycle time,($2^-$(ΔΔCt)), for treated vs. control, about 0.62±0.16 vs. about 1.01±0.12, mean±Std Err) using TBP+RPLPO as normalizing variables for Formula IIa. mRNA knockdown is confirmed by in situ hybridization using a third probe targeted to downstream of the binding site for the high and middle dose but not the low dose groups confirming microscopy and western blotting. Inhibition appears similar by in situ hybridization for at least the high dose of Formula Hb which was examined.

Example 6—Superior Efficacy of Instant CRISPR Complex Nanoparticles Demonstrated In Vivo We assay for functional in vivo activity of the CRISPR complex nanoparticles i.e. bacterial endonuclease Cas9 reacted with about a 105 nt anti-Factor VII guide RNA (sgRNA, described as Formula H in Example 1) in Balb/C immunocompetent mice. In this study, we compare two formulas, a shorter dissolution capsule (prepared using a shorter crystallization period amenable to in vitro studies, Formula Ha) and a longer dissolution capsule (generally used for longer in vivo circulation, Formula Hb).

Three dosing levels are examined with a two dose regimen; 1) about 10e14 particles at about 1.6 mg/kg; 2) about 10e13 particles at about 160 µg/kg q3D; and 3) about 10e12 particles at about 16 µg/kg q3D of RISC nanoparticles. Particle numbers are estimated assuming closest theoretical packing into final particle size measured by DLS. A fractional factorial design is used with groups of three assigned to each dissolution profile design, and mice are sacrificed to collect livers for microscopy, western blotting, qPCR and mutational analysis at 7 days post initiation of treatment.

We investigate changes in Factor VII and Cas9 protein component immunosignal by confocal immunofluorescence microscopy for the groups over the dose range. Cas9 immunosignal is used for capsule localization and trafficking while Factor VII protein immunosignal demonstrates the phenotypic effect of Factor VII mutation and/or CRISPR-based silencing. Results are illustrated in FIG. 4.

We find that Cas9 immunosignal (the nanoparticle cargo) shows a punctate cytoskeletal pattern at mg/kg dose levels (highest dose, about 10e14 particles) in individual hepatocytes that decreased with dose level to not detectable at about 16 µg/kg (lowest dose level, about 10e12 particles).

At the same time, Factor VII immunosignal is maximally decreased as detectable Cas9 signal disappears suggesting a sequence of events where capsule processing to "release" Cas9 for action is hindered in the case of potentially too many capsules entering the cell. This means that the highest dose tested is not the optimal biological dose (OPD). This pattern of persistent Cas9 immunosignal indicating saturation corresponding with poorer Factor VII inhibition is confirmed in 3D hepatocyte cell culture.

For Factor VII immunosignal, we observe reduction in signal in 3D mouse hepatocytes that appear maximal at about 1 pmol (about 4 nM) and is nearly recovered by about 0.1 pmol (about 0.4 nM). At the highest dose level of about 5 nmol, no reduction in Factor VII is observed consistent with the existence of an optimal biological dose.

We additionally perform western blotting of liver lysates from mice under denaturing conditions confirming our observations by microscopy. Under denaturing conditions, Factor VII separates into three fragments of about 73, 50 and 43 kDa. Densitometry of Factor VII bands (Genetex) normalized to VDAC (CMillipore) levels indicate about 40-85% knockdown of the three fragments at the peak effective middle dose of about 2×3e12 q3D particles or about 2×160 µg/kg. Results are summarized above in Table 4.

With respect to mutation, amplicon sequencing using an Illumina Miseq approach detects no double strand breaks as having occurred at the target site which indicates no cutting activity of the Cas9 enzyme. We examine mRNA levels for the best responding group (middle dose) using primers that either bind upstream of the Exon 2 binding site (Exon 1) or downstream of the Exon 2 binding site (Exon 4). qPCR executed using Exon 1 primer indicates no change in Factor VII transcript had occurred while qPCR executed using the downstream Exon 4 primer indicated an approximately 30% decrease in transcript measured as ($\Delta$cycle time,($2^\wedge$-($\Delta\Delta$Ct)), for treated vs. control, about 0.07±0.09 vs. about 1.01±0.07, mean±Std Err) using TBP+RPLPO as normalizing variables for Formula Ha. Consistent mRNA knockdown is confirmed by in situ hybridization using a third probe targeted to downstream of the binding site for the middle dose with some response seen in the high and low dose groups confirming microscopy and western blotting. Inhibition appears similar by in situ hybridization for at least the high dose of Formula Hb which is examined.

Example 7—CRISPR Nanoparticles Avoid Immunologic Response

Animals from Example—5 are examined for immune response to nanoparticle treatment.

Lethal inflammatory responses have been a problematic sequelae of conventional non-viral strategies for systemic delivery of bacterially-derived NPs. In this study (from Example—5), all mice survive and are assayed for a panel of inflammatory cytodines, including GM-CSF, IFNa, IFNg, IL-1b, IL-6, MCP-1, Rantes and TNFa in the highest dose level group (2×1.6 mg/kg, 3e12 particles) for both nanoparticle designs (Formulas Ha, Hb) vs. control. As previously mentioned, this top dose level was also found to be non-optimal coincident with dysregulation in intracellular trafficking. We find no changes from control in any parameter for any of the mice in the shorter circulation design capsule (Formula Ha) and note some significant elevations (IFNa, IL-6, MCP-1,TNFa) for one mouse in the longer dissolution design.

We compared Factor VII inhibition between ASOR-ligand crystalline particles bearing Cas9, non-canonical Cas9 or dead Cas9 protein complexes in 3D hepatocyte cell culture. The canonical spCas9 endonuclease undergoextensive structural conformation change upon guide RNA binding. Upon guide RNA recognition and binding, the REC lobe moves ~65 angstoms (about 6.7 nm) towards the Nuc lobe in a clamshell motion indicating mechanical fragility. Non-canonical Cas9 enzymes do not contain this particular structure for nuclease activity. dCas9 is mutated (H840A, D10A) in the HNH and RUVEC cleavage domains respectively but does not lose substrate recognition for the guide RNA and joint substrate recognition for the target chromosome site. When dCas9 enzyme binds its sgRNA substrate, it physically reconfigures and transforms into a specific chromosomal binding protein to block mRNA transcription by the RNA polymerase.

Example 8—CRISPR Nanoparticles Avoid Immunologic Response

Animals from Example—5 are examined for immune response to nanoparticle treatment.

Lethal inflammatory responses have been a problematic sequelae of conventional non-viral strategies for systemic delivery of bacterially-derived NPs. In this study (from Example—5), all mice survive and are assayed for a panel of inflammatory cytodines, including GM-CSF, IFNa, IFNg, IL-1b, IL-6, MCP-1, Rantes and TNFa in the highest dose level group (about 2×1.6 mg/kg, about 3e12 particles) for both nanoparticle designs (Formulas Ha, Hb) vs. control. As previously mentioned, this top dose level is also found to be non-optimal coincident with dysregulation in intracellular trafficking. We find no changes from control in any parameter for any of the mice in the shorter circulation design capsule (Formula Ha) and note some significant elevations (IFNa, IL-6, MCP-1,TNFa) for one mouse in the longer dissolution design.

We compare Factor VII inhibition between ASOR-ligand crystalline particles bearing Cas9, non-canonical Cas9 or dead Cas9 protein complexes in 3D hepatocyte cell culture. dCas9 is mutated (H840A, D10A) in the HNH and RUVEC cleavage domains respectively but does not lose substrate recognition for the guide RNA and joint substrate recognition for the target chromosome site. When dCas9 enzyme binds its sgRNA substrate, it physically reconfigures and transforms into a specific chromosomal binding protein to block mRNA transcription by the RNA polymerase.

Example 9—CRISPR Nanoparticles Avoid Immunologic Response

Animals from Example—5 are examined for immune response to nanoparticle treatment.

Lethal inflammatory responses have been a problematic sequelae of conventional non-viral strategies for systemic delivery of bacterially-derived NPs. In this study (from Example—5), all mice survive and are assayed for a panel of inflammatory cytodines, including GM-CSF, IFNa, IFNg, IL-1b, IL-6, MCP-1, Rantes and TNFa in the highest dose level group (about 2×1.6 mg/kg, about 10e14 particles) for both nanoparticle designs (Formulas Ha, Hb) vs. control. As previously mentioned, this top dose level is also found to be non-optimal coincident with dysregulation in intracellular trafficking. We find no changes from control in any parameter for any of the mice in the shorter circulation design capsule (Formula Ha) and note some significant elevations (IFNa, IL-6, MCP-1,TNFa) for one mouse in the longer dissolution design.

We compare Factor VII inhibition between ASOR-ligand crystalline particles bearing Cas9, non-canonical Cas9 or dead Cas9 protein complexes in 3D hepatocyte cell culture. The canonical spCas9 endonuclease undergo extensive structural conformation change upon guide RNA binding. Upon guide RNA recognition and binding, the REC lobe moves ~65 angstoms (about 6.7 nm) towards the Nuc lobe in a clamshell motion indicating mechanical fragility. Non-canonical Cas9 enzymes do not contain this particular structure for nuclease activity. dCas9 is mutated (H840A, D10A) in the HNH and RUVEC cleavage domains respectively but does not lose substrate recognition for the guide RNA and joint substrate recognition for the target chromosome site. When dCas9 enzyme binds its sgRNA substrate, it physically reconfigures and transforms into a specific chromosomal binding protein to block mRNA transcription by the RNA polymerase.

Example 10—In Vitro Analysis of Factor VII Protein Levels 3D hepatocyte cell cultures are prepared by plating about 25,000 murine FL3B murine hepatocyte cells on to ECM-coated spun polymer scaffolds (Corning, UltraMax) in chamber slides. It is worth noting that cells completely reorganize their internal geometry in 3D systems, supporting the use of 3D cultures in CRISPR and intracellular trafficking studies.

Results for Formulas Ha and Hb are illustrated in FIG. 4. Neither formulation showed significant mutation activity while plasmid Cas9 and plasmid sgRNA delivered from separate ASOR nanoencapsulates did show mutational activity by amplicon deep sequencing. In a separate 3D experiment, Formula Hc, in contrast to Formula Ha, induces mutation of the F7 sequence at the level of the chromosome along with inhibition of F7 protein expression.

Neither formulation shows significant mutation activity while plasmid Cas9 and sgRNA delivered from separate ASOR nanoencapsulates do show mutational activity by amplicon deep sequencing.

We conclude that protein co-encapsulation with a polynucleotide substrate is effective for enhancing incorporation into crystalline supramolecular complexes for retention of enzyme bioactivity in non-inflammatory systemic delivery of bacterial dCas9 protein.

Example 11—Protein Co-Encapsulation of Protein Component with Polynucleotide Component Enriches Cells with Active RISC for Enhanced Target Gene Modulation Superior efficacy of the instant nanoparticles (Risc RNAi F7; Formula B) is demonstrated in comparison to guide strand alone (Formula E) nanoparticles in 3D cultured FL83B hepatocytes (ATCC).

3D hepatocyte cell cultures are prepared by plating about 25,000 murine FL83B murine hepatocyte cells on to ECM-coated spun polymer scaffolds (Corning, UltraMax) in chamber slides. Formula B and Formula E nanoparticles are added at various concentrations to the cultures and harvested for microscopy after about 3 days.

Dose response for Factor VII protein inhibition is assayed by confocal fluorescence microscopy for Factor VII immunosignal (GeneTex).

Formula B administration demonstrates full inhibition of Factor VII protein at about 1 pmol (about 4 nM) continuing through about 2.0 nM with recovery beginning around about 0.32 nM demonstrating about a 3 log response range. In contrast, Formula E bearing the guide strand only shows full inhibition by microscopy at about 5 nmol (about 20 µM) recovering by about 1.25 nmol (about 5 µM) for about a 0.4 log response range and approximate increase in activity of about about 3.5 logs (about 2 nM vs. 12.5 µM) for encapsulated RISC complex vs encapsulated guide RNA alone. Results are illustrated in FIG. 3.

Example 12—In Vitro Analysis of Factor VII Protein Levels 3D hepatocyte cell cultures are prepared by plating about 25,000 murine FL3B murine hepatocyte cells on to ECM-coated spun polymer scaffolds (Corning, UltraMax) in chamber slides. It is worth noting that cells completely reorganize their internal geometry in 3D systems, supporting the use of 3D cultures in CRISPR and intracellular trafficking studies.

Figure 5:
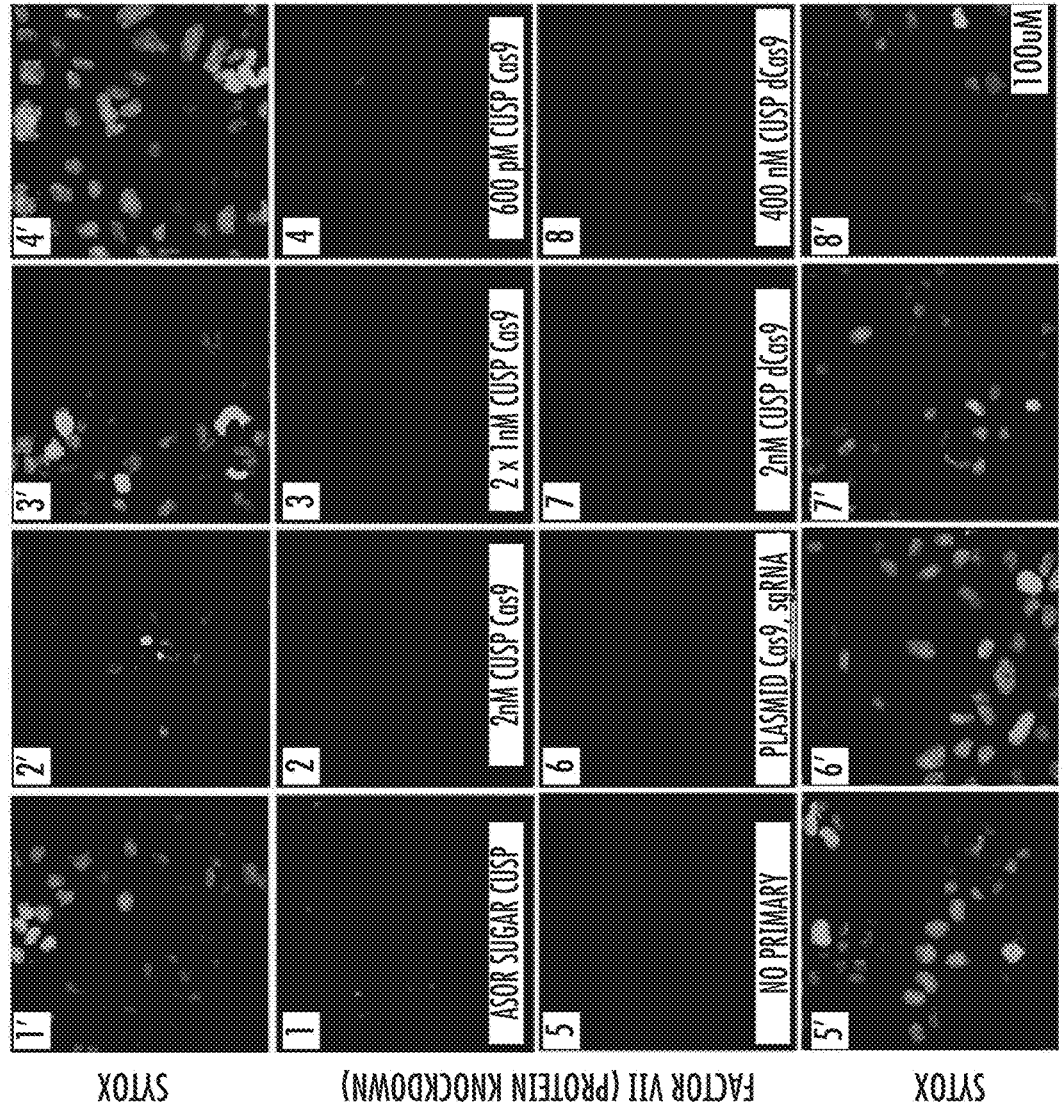
FIG. 5 shows immunohistochemistry in 3D hepatocyte cultures.

Formula Ha (ASOR Cas9 crF7) and Formula I (ASOR dCas9 crF7) are analyzed for functional activity by treating 3D mouse hepatocyte cultures at two dose levels (about 2 nM and 0.4-0.6 nM) and then are assayed for Factor VII protein levels after about 3 days by confocal immunofluorescence microscopy. We observed a similar pattern for both formulations with significant inhibition for both formulations at about 2 nM and partial inhibition at about 0.4-0.6 nM of Cas9 protein. Results are illustrated in FIG. 5.

Neither formulation shows significant mutation activity while plasmid Cas9 and sgRNA deliver from separate ASOR nanoencapsulates show mutational activity by amplicon deep sequencing.

We conclude that protein co-encapsulation with a polynucleotide substrate is effective for enhancing incorporation into crystalline supramolecular complexes for retention of enzyme bioactivity in non-inflammatory systemic delivery of bacterial dCas9 protein.

Example 13—In Vitro Analysis of Factor VII Protein Levels 3D hepatocyte cell cultures are prepared by plating about 25,000 murine FL3B murine hepatocyte cells on to ECM-coated spun polymer scaffolds (Corning, UltraMax) in chamber slides. It is worth noting that cells completely reorganize their internal geometry in 3D systems, supporting the use of 3D cultures in CRISPR and intracellular trafficking studies.

Results for Formulas Ha and I are illustrated in FIG. 4. Neither formulation shows significant mutation activity while plasmid Cas9 and plasmid sgRNA delivered from separate ASOR nanoencapsulates show mutational activity by amplicon deep sequencing. In a separate 3D experiment, Formula He and Formula Hd, in contrast to Formula Ha, induce mutation of the F7 sequence at the level of the chromosome along with inhibition of F7 protein expression.

Neither formulation shows significant mutation activity while plasmid Cas9 and sgRNA delivered from separate ASOR nanoencapsulates show mutational activity by amplicon deep sequencing.

We conclude that protein co-encapsulation with a polynucleotide substrate is effective for enhancing incorporation into crystalline supramolecular complexes for retention of enzyme bioactivity in non-inflammatory systemic delivery of bacterial dCas9 protein.

Example 14—Spectral Characterization of Instant Crystalline Nanoparticles

To further elucidate a basis for the surprising effectiveness for effective systemic delivery of nanoparticles with co-encapsulated protein and polynucleotide components, we analyze thermal spectra by differential scanning calorimetry (DSC) from dried and crushed powders and FTIR spectra in hydrated and partially dehydrated powders prepared either by drying under vacuum with mild heat or buffer exchange with 10 mM ammonium acetate (NH4Oac) followed by similar drying optionally with sample freezing at −80° C. preceding drying. For FTIR spectra, final nanoparticle preparations are compared to ligand-coated micelle intermediates prepared up until cocrystallization in a salt mixture of primarily Cs-modified lithium.

TABLE 5

Spectral characteristics of nanoparticles and uncrystallized intermediates.

Figure 6:
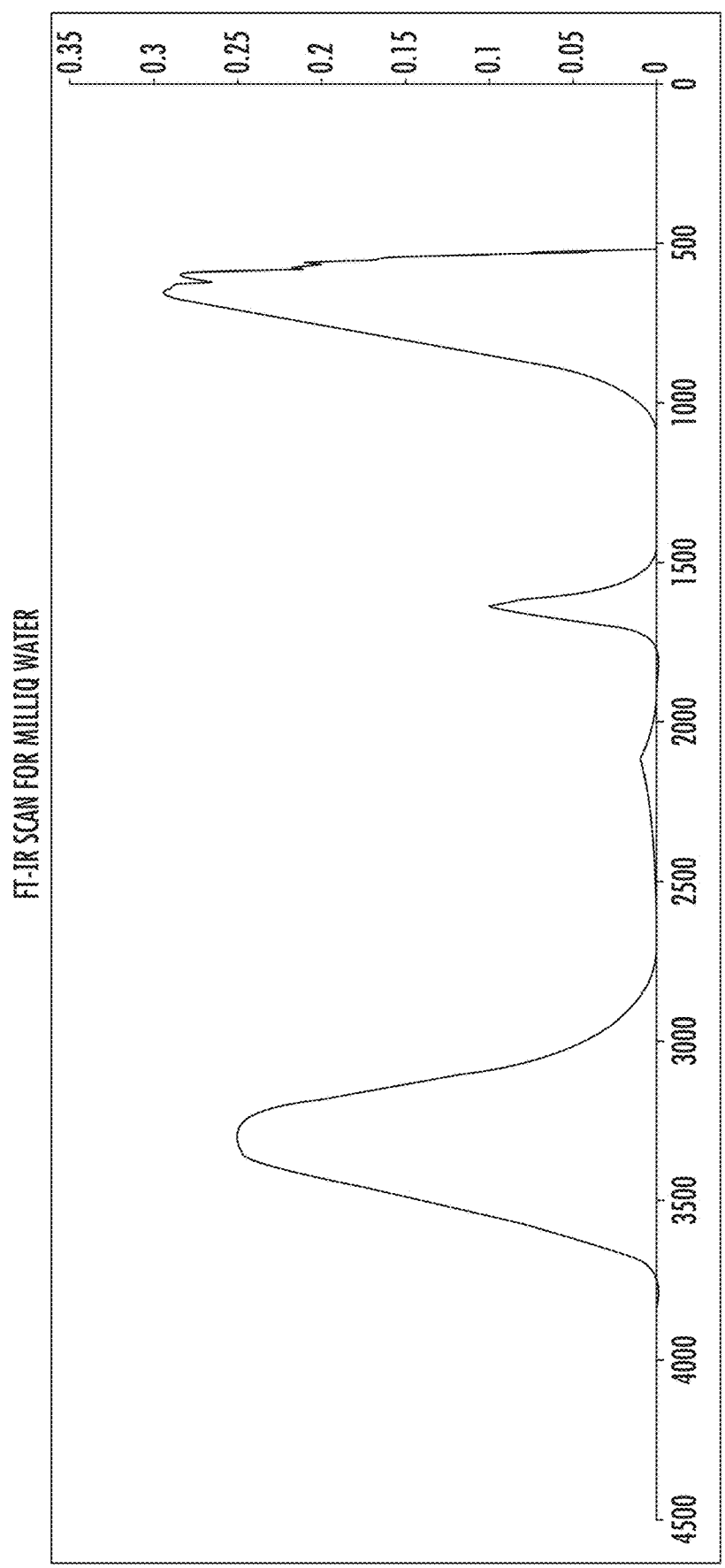
FIG. 6 shows FT-IR Scan for MilliQ Water.
Figure 7:
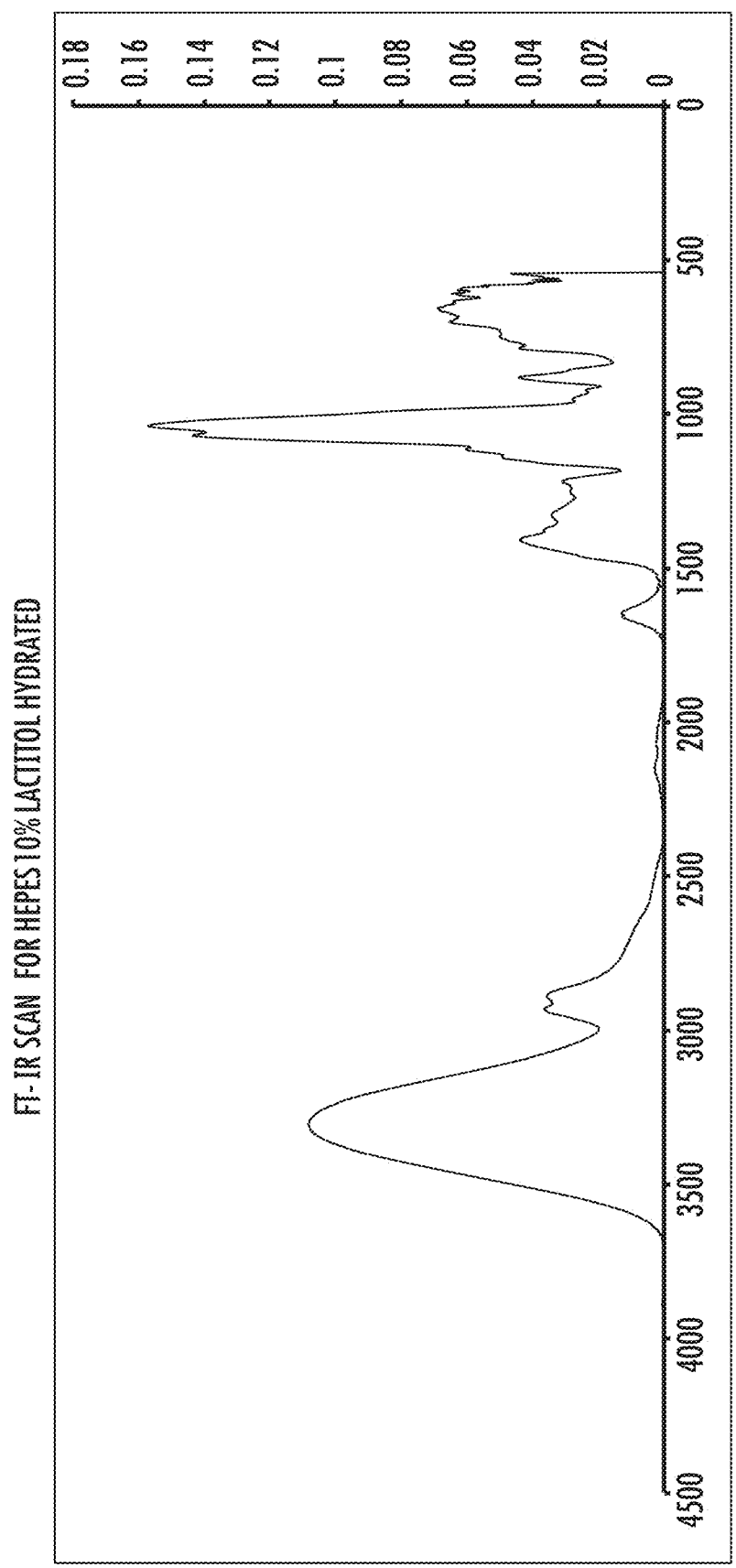
FIG. 7 shows FT-IR Scan for Hepes 10% Lactitol hydrated.
Figure 8:
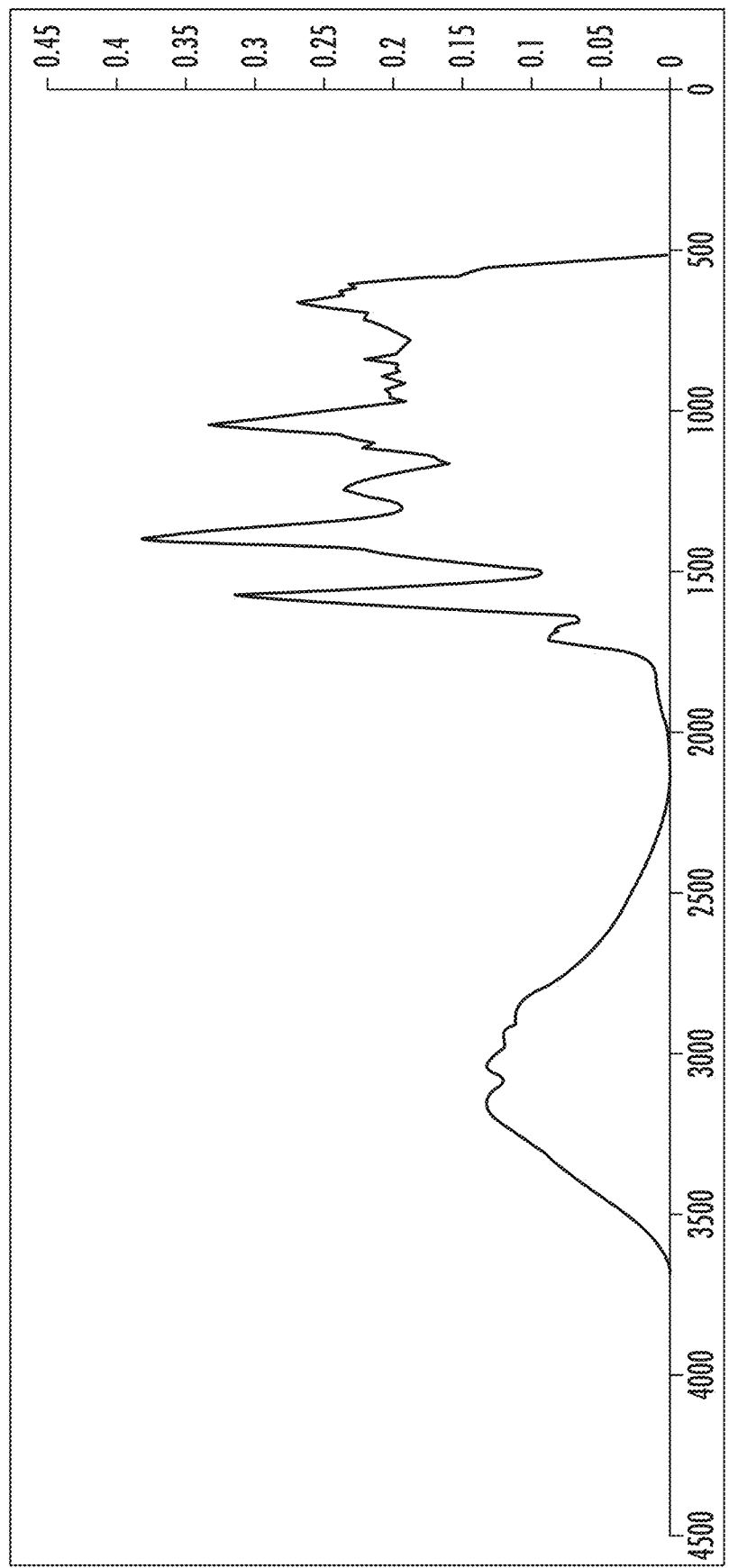
FIG. 8 shows FT-IR Scan for Hepes 10% Lactitol partially dehydrated.
Figure 9:
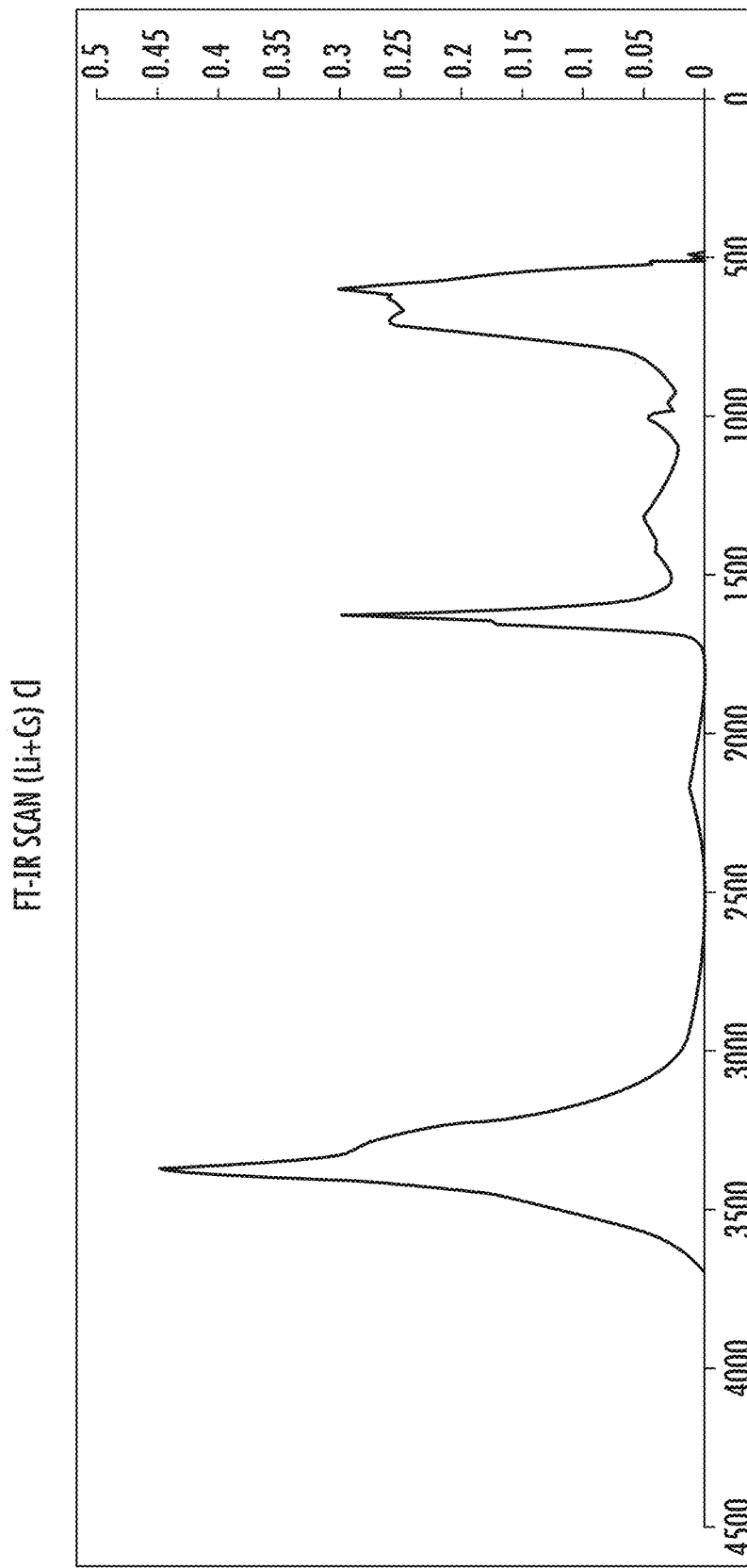
FIG. 9 shows FT-IR Scan (Li+ Cs) Cl.
Figure 10:
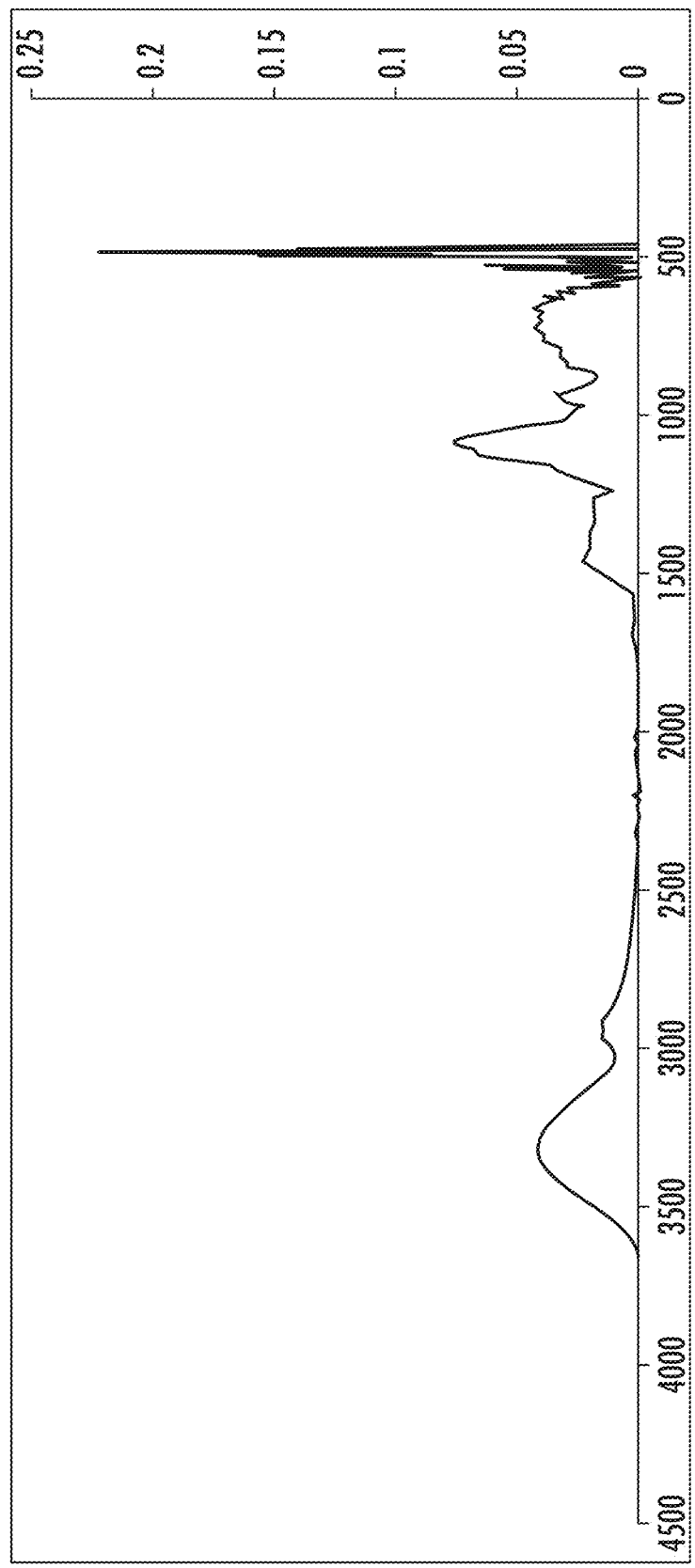
FIG. 10 shows FT-IR Scan for ASOR hydrated.

| Particle/Cargo | Formula | DSC Transitions[1], ° C., gt midpoints, et nadirs | Delta Cp (J/(g*° C.)) | FTIR spectrum, hydrated[3] (wavenumber, cm−1) | FTIR spectrum, dehydrated[3] (wavenumber, cm−1) |
|---|---|---|---|---|---|
| Milli-Q water | | ND | ND | FIG. 6 | ND |
| Hepes + 10% Lactitol diluent | | et's 301.1, 315.5, 335.3 | 10.828, 1.493, 5.175 | FIG. 7 | FIG. 8 |
| Cs-modified lithium | | ND | ND | FIG. 9 | ND |
| ASOR ligand | | ND | ND | FIG. 10 | ND |
| DMSO | | ND | ND | FIG. 11 | ND |
| NH4Oac | | ND | ND | FIG. 12 | ND |
| ASOR Erythritol nanoparticle | G | et's, 44.8, 145.6, 159.8, 183.0, 195.7, 288.7, 312.8 | 0.744, 0.422, 1.277, 0.173, 0.168, 0.279, 0.686 | FIG. 13 | FIG. 14 |
| ASOR Erythritol micelle[2] | G | ND | ND | ND | FIG. 15 |
| ASOR RISC RNAi F7 nanoparticle7 | B | et's, 40.0, 136.1, 150.2, 157.0, 167.6, 285.4, 289.0, 314.2 | 1.008, 1.185, 0.972, 0.190, 0.746, 0.029, 0.652, 5.185 | ND | FIG. 16 |
| ASOR RISC RNAi F7 micelle[2] | C | ND | ND | ND | FIG. 17 |
| ASOR RISC 2RF7 micelle[2] | Da | ND | ND | ND | FIG. 18 |
| ASOR RNAi F7 nanoparticle | E | et's, 41.9, 307.8, 329.4 | 2.383, 6.672, 1.400 | ND | FIG. 19 |
| ASOR RNAi F7 micelle[2] | E | ND | ND | ND | FIG. 20 |
| ASOR Cas9 F7 nanoparticle | Ha | et's, 46.5, 136.0, 243.3, 305.8 | 3.381, 0.447, 0.899, 1.183 | FIG. 21 | FIG. 22 |
| ASOR Cas9 F7 micelle[2] | Ha | ND | ND | ND | FIG. 23 |
| ASOR dCas9 F7 nanoparticle | I | et's, 48.2, 312.6, 329.8 | 0.680, 2.697, 0.494 | ND | FIG. 24 |
| ASOR dCas9 F7 micelle[2] | I | ND | ND | ND | FIG. 25 |

*fn[1] references paragraph [00249];
fn[2] references paragraph [00250]; and
fn[3] references paragraph [00251]

Referring to Table 5, Thermal transitions and transition energies are identified from thermograms generated by differential scanning calorimetry (DSC) on a STA 449 F3-Jupiter thermal analyzer. Suspensions are dried to produce powder for analysis, and about 1-2 mg were scanned at about 20° C./min from room temperature to about 400° C. in uncrimped aluminum pans. Abbreviations used here are: gt, glass transition; et, endotherm; vs. very small.

Ligand-coated micelles are micelles formulated according to respective formulation but do not undergo incubation in salt receiving solution.

The FTIR spectra are recorded from about 400 to 4000 $cm^{-1}$ using an Agilent Cary 670 spectrophotometer, equipped with a Pile MIRacle ATR accessory a mid-infrared source as the excitation source. Liquid samples are placed directly on the crystal, and the high pressure clamp is used for solid samples. Prior to analysis, the entire instrument is purged with dry, $CO_2$-free air for at least 30 minutes and until background scans indicated no or negligible change in atmospheric moisture or $CO_2$ levels. The ATR crystal and the high pressure clamp are both cleaned with mQ water (18Ω) between measurements and dried with a cotton cloth until the processed spectrum indicated that no residual sample remained on the crystal. The spectra were acquired in about 32 scans at a resolution of about 1 $cm^{-1}$ at ambient conditions. Abbreviations, v, very; s, small; md, moderate; str, strong; brd, broad.

In these analyses, DSC shows only endotherms in final lithium-treated particles supporting crystallinity for ASOR Cs-modified lithium polymorphs.

Compound differences upon supramolecular assemblies bearing diverse cargos are further investigated by FTIR spectroscopy.

FTIR of hydrated nanoparticle powders identify a peak attributable to the ASOR ligand at about 1035 (about 1010-1050) $cm^{-1}$. Upon partial dehydration, a peak attributable to the Cs-modified lithium is readily apparent at about 620-650 $cm^1$ while at the same time the ASOR ligand peak was greatly diminished. This broad doublet at about 655, 620 $cm^{-1}$ is not visible in powders from paired ligand-coated intermediates before lithium exposure. Generally, the spectral pattern of ASOR-liganded crystalline capsulesis similar despite diverse cargos. However, spectra from ASOR ligand-coated intermediates does show differences between diverse cargos that are not apparent in spectra from final product. An approximately about 875 $cm^{-1}$ peak attributable to the TM-diol surfactant along with the peak attributable to the ASOR ligand is dampened considerably coincident with the processes in effect in the crystallization step. Consistent with hypothesis of considerable surface rearrangement upon lithium exposure, a peak at about 1690 (about 1685-1715) $cm^{-1}$ attributable to carbonyl (C=O) stretching is also greatly decreased. Without wishing to be bound by theory, it is believed that the lithium ion is able to coordinate a water-stable bond between carboxyl anions, particularly carboxylate anions, to create a stabilizing network of bonds and thus innumerable unique supramolecular structures.

Significant changes in thermal transitions and IR spectra are important indicators of polymorphic change in crystalline compounds, pharmaceutical compounds, and nanoscale supramolecular assemblies.

Example 15—Non-Crystallized Particles for Short-Release Applications

Formula B (ASOR RISC RNAiF7) and Formula E (ASOR RNAi F7), are prepared as ASOR-coated micelles and ligand-coated micelles, terminating synthesis just before addition to the lithium receiving bath for crystallization and hardening (referred to herein as "non-crystallized nanoparticles"). 3D cultures of FL83B are treated at six dose levels of about 1 pmol, about 0.5 pmol, about 0.1 pmol, about 0.05 pmol and about 0.01 pmol for Formula B and about 5 nmol, about 2.5, about 1.25, about 0.75, about 0.5 and about 0.1 nmol for Formula E to show increased activity at lower doses than observed with fully crystallized particles. This example shows as one embodiment the instant non-crystallized nanoparticles are useful to deliver protein-substrate combinations in applications where a drug is desirably released faster than it is with a crystallized particle. In one embodiment, the applications for the instant non-crystallized nanoparticles are used over the short time course of a cell culture experiment.

Significant changes in thermal transitions and IR spectra are important indicators of polymorphic change in crystalline compounds, pharmaceutical compounds, and nanoscale supramolecular assemblies.

Example 16—Effective Formulation and Delivery of Protein Enzyme Therapies Comprising Protein-Protein Combinations Formula J (Tenfibgen Chymotrypsin-trypsin) is prepared as ASOR-coated micelles and ligand-coated micelles, terminating synthesis just before addition to the lithium receiving bath for crystallization and hardening. Formula K is prepared as a suspension of Tenfibgen crystalline nanoparticles containing erythritol for a comparator nanoparticle. Organ cultures of dermal explants representing normal and wound-activated conditions, eg. post-radiation, are treated at about 3 dose levels of Chymotrpsin-Trypsin; eg. about 1 ug, about 5 ug and about 10 ug among others by either intradermal injection of naked enzyme or by enzyme delivered topically as a non-ionic micelle, ligand-coated micelle or crystalline ligand-coated nanoparticle. Erythritol capsules are applied similarly as a comparator. Organ cultures are held either overnight for localization of Chymotrypsin (or Syrian Hamster IgG incorporated as capsule label) in tissue by microscopy or for about three days for examination of protease activity by immunohistochemistry and Massons Trichrome staining. More uniform action of the enzyme upon the tissue is observed to be facilitated by inventive formulations relative to injection of naked enzyme.

VIII. INCORPORATION BY REFERENCE

Any and all patents, patent applications, patent application publications and PCT publications, publications, including any and all references, articles, website articles and abstracts, referenced or identified herein, included their entire contents, are incorporated herein by reference in their entireties as if each has been fully set forth herein.

IX. EQUIVALENTS

Various modifications and variations of the described methods, compositions, processes and systems of the invention will be apparent to those of skill in the art without departing from the scope and spirit of the invention. Although the invention has been described in connection with specific exemplary preferred embodiments, it should be understood that the invention as claimed should not be unduly limited to such specific exemplary embodiments. Indeed, various modifications of the described modes for carrying out and/or practicing the invention are intended to be within the scope of the claims.

Having described our invention, we claim:

1. A composition comprising nanoparticles comprising a polynucleotide component, a protein component, a surfactant having a hydrophile-lipophile balance (HLB) value of less than 6.0 units, optionally a hydrophilic polymer, and optionally $Li^+$ and $Cs^+$, the polynucleotide component being a guide strand and wherein the guide strand is a member selected from the group consisting of ssRNA, siRNA, and miRNA, the protein component being a RISC-associated protein or a CRISPR-associated protein, wherein:
   a) the protein component and the polynucleotide component are capable of functioning together in a biologic system as a biologic agent;
   b) the protein component and the polynucleotide component form a complex;
   c) the complex and the surfactant form a surfactant micelle core;
   d) the optionally hydrophilic polymer, if present, forms a shell around the micelle core;
   e) the nanoparticles have an average diameter of less than about 50 nanometers; and
   f) the biologic agent is optionally a therapeutic agent.

2. The composition of claim 1 wherein the biologic agent is a RISC or a single-guide RNA (sgRNA)-Cas complex.

3. The composition of claim 1 wherein the biologic agent is a Triplex-forming peptide nucleic acid oligomer (PNA), or a structure-guided endonuclease gene editing technology (SGN).

4. The composition of claim 2 wherein the protein component is the RISC associated protein and the polynucleotide component is a guide strand and wherein the guide strand is a member selected from the group consisting of ssRNA, siRNA, and miRNA.

5. The composition of claim 4 wherein the RISC-associated protein is an argonaute protein.

6. The composition of claim 5 wherein the argonaute protein is AGO-2.

7. The composition of claim 1 wherein the protein component is the CRISPR associated protein and the polynucleotide component is sgRNA.

8. The composition of claim 7 wherein the CRISPR associated protein is Cas-9.

9. The composition of claim 7 wherein the CRISPR associated protein is dCas-9.

10. The composition of claim 1, further comprising a donor template DNA.

11. The composition of claim 1, wherein the polynucleotide component is configured to target the biologic agent to a gene that is expressed in muscle, lung, or liver.

12. A composition comprising nanoparticles comprising a first protein component, a second protein component different from the first, a surfactant having an HLB value of less than 6.0 units, optionally a hydrophilic polymer, and optionally Li+ and Cs+, the first and second protein components being selected from a RISC associated protein or a CRISPR associated protein, wherein:
   a) the first protein component and the second protein component form a complex;
   b) the complex and the surfactant form a surfactant micelle core;
   c) the optionally hydrophilic polymer, if present, forms a shell around the micelle core;
   d) the nanoparticles have an average diameter of less than about 50 nanometers; and
   e) the biologic agent is optionally a therapeutic agent.

13. The composition of claim 12, wherein the biologic agent is a RISC or a single-guide RNA (sgRNA)-Cas complex.

14. The composition of claim 12, wherein the protein component is the CRISPR associated protein and the polynucleotide component is sgRNA.

15. The composition of claim 13 wherein the protein component is the RISC associated protein and the polynucleotide component is a guide strand and wherein the guide strand is a member selected from the group consisting of ssRNA, siRNA, and miRNA.

16. The composition of claim 15 wherein the RISC-associated protein is an argonaute protein.

17. The composition of claim 16 wherein the argonaute protein is AGO-2.

18. The composition of claim 12 wherein the biologic agent is a Triplex-forming peptide nucleic acid oligomer (PNA), or a structure-guided endonuclease gene editing technology (SGN).

19. The composition of claim 14 wherein the CRISPR associated protein is Cas-9.

20. The composition of claim 14 wherein the CRISPR associated protein is dCas-9.

* * * * *